US010925881B2

(12) United States Patent
Landau et al.

(10) Patent No.: US 10,925,881 B2
(45) Date of Patent: Feb. 23, 2021

(54) TREATMENT OF CONDITIONS ASSOCIATED WITH HYPERINSULINAEMIA

(71) Applicant: Tensha Therapeutics, Inc., South San Francisco, CA (US)

(72) Inventors: Steven B. Landau, Wellesley, MA (US); Michael H. Kagey, Arlington, MA (US)

(73) Assignee: Tensha Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 15/121,964

(22) PCT Filed: Feb. 27, 2015

(86) PCT No.: PCT/US2015/018118
§ 371 (c)(1),
(2) Date: Aug. 26, 2016

(87) PCT Pub. No.: WO2015/131113
PCT Pub. Date: Sep. 3, 2015

(65) Prior Publication Data
US 2017/0209461 A1 Jul. 27, 2017

Related U.S. Application Data

(60) Provisional application No. 61/946,682, filed on Feb. 28, 2014, provisional application No. 62/019,777, filed on Jul. 1, 2014, provisional application No. 62/054,620, filed on Sep. 24, 2014.

(51) Int. Cl.
*A61P 29/00* (2006.01)
*A61K 31/5517* (2006.01)

(52) U.S. Cl.
CPC .................................. *A61K 31/5517* (2013.01)

(58) Field of Classification Search
None
See application file for complete search history.

(56) References Cited

U.S. PATENT DOCUMENTS

| | | | |
|---|---|---|---|
| 2,951,540 A | 9/1960 | Hawkins | |
| 3,681,343 A | 8/1972 | Hester, Jr. | |
| 3,709,898 A | 1/1973 | Hester, Jr. | |
| 3,812,259 A | 5/1974 | Collins | |
| 4,621,083 A | 11/1986 | Casals-Stenzel et al. | |
| 5,104,543 A | 4/1992 | Brandt et al. | |
| 5,593,988 A | 1/1997 | Tahara et al. | |
| 5,712,274 A | 1/1998 | Sueoka et al. | |
| 5,721,231 A | 2/1998 | Moriwaki et al. | |
| 5,753,649 A | 5/1998 | Tahara et al. | |
| 5,760,032 A | 6/1998 | Kitajima et al. | |
| 5,846,972 A | 12/1998 | Buckman et al. | |
| 5,854,238 A | 12/1998 | Kempen | |
| 6,312,215 B1 | 11/2001 | Walker | |
| 6,444,664 B1 | 9/2002 | Princen et al. | |
| 6,861,422 B2 | 3/2005 | Hoffmann et al. | |
| 7,015,213 B1 | 3/2006 | Bigg et al. | |
| 7,528,143 B2 | 5/2009 | Noronha et al. | |
| 7,528,153 B2 | 5/2009 | Aerts | |
| 7,589,167 B2 | 9/2009 | Zhou et al. | |
| 7,750,152 B2 | 7/2010 | Hoffman et al. | |
| 7,786,299 B2 | 8/2010 | Hoffmann et al. | |
| 7,816,530 B2 | 10/2010 | Grauert | |
| 7,825,246 B2 | 11/2010 | Noronha et al. | |
| 8,003,786 B2 | 8/2011 | Hoffmann et al. | |
| 8,044,042 B2 | 10/2011 | Adachi et al. | |
| 8,133,900 B2 | 3/2012 | Hood et al. | |
| 8,138,199 B2 | 3/2012 | Noronha et al. | |
| 8,338,464 B2 | 12/2012 | Melnick et al. | |
| 8,476,260 B2 | 7/2013 | Miyoshi et al. | |
| 8,604,042 B2 | 12/2013 | Noronha et al. | |
| 8,981,083 B2 * | 3/2015 | Bradner | C07D 495/14 540/560 |
| 9,301,962 B2 | 4/2016 | Bradner et al. | |
| 9,320,711 B2 | 4/2016 | Natoli et al. | |
| 9,320,741 B2 * | 4/2016 | Bradner | A61P 35/00 |
| 9,763,956 B2 | 9/2017 | Bernstein et al. | |
| 9,789,120 B2 | 10/2017 | Bradner et al. | |
| 9,815,849 B2 | 11/2017 | Bradner et al. | |
| 10,124,009 B2 * | 11/2018 | Landau | A61P 15/16 |
| 10,407,441 B2 * | 9/2019 | Bradner | A61P 35/00 |
| 2002/0032200 A1 | 3/2002 | Cai et al. | |
| 2002/0169158 A1 | 11/2002 | Hunt et al. | |
| 2003/0130268 A1 | 7/2003 | Sagara et al. | |
| 2003/0216758 A1 | 11/2003 | Signore | |
| 2004/0043378 A1 | 3/2004 | Zhou et al. | |

(Continued)

FOREIGN PATENT DOCUMENTS

| | | |
|---|---|---|
| CA | 2020806 A1 | 1/1991 |
| CA | 2710740 A1 | 7/2009 |

(Continued)

OTHER PUBLICATIONS

Diamanti-Kandarakis et al., "Therapeutic effects of metformin on insulin resistance and hyperandrogenism in polycystic ovary syndrome," European Journal of Endocrinology 1998; 138: pp. 269-274.*
Shanik et al., "Insulin Resistance and Hyperinsulinemia," Diabetes Care, (2008); 31(2): pp. S262-S268. (Year: 2008).*
González-Barrosa et al., "Mutations in UCP2 in Congenital Hyperinsulism Reveal a Role for Regulation of Insulin Secretion," PLoS One (2008); 3(1): pp. 1-8. (Year: 2008).*
Sawicki et al., "Normal Blood Pressure in Patients with Insulinoma Despite Hyperinsulinemia and Insulin Resistance," J. Am. Soc. Neprhol., 1992; 3:S64-S68. (Year: 1992).*
Final Rejection for U.S. Appl. No. 13/697,963, "Compositions and Methods for Modulating Metabolism," dated Aug. 21, 2015.

(Continued)

*Primary Examiner* — Layla Soroush
(74) *Attorney, Agent, or Firm* — . Foley Hoag LLP

(57) ABSTRACT

The present invention relates to treatment of a condition associated with hyperinsulinaemia using the compounds described herein.

16 Claims, 16 Drawing Sheets

(56) References Cited

U.S. PATENT DOCUMENTS

| | | |
|---|---|---|
| 2004/0176380 A1 | 9/2004 | Hoffmann et al. |
| 2006/0074088 A1 | 4/2006 | Munzert et al. |
| 2006/0142257 A1 | 6/2006 | Nieschlag et al. |
| 2006/0223055 A1 | 10/2006 | Howley et al. |
| 2007/0105839 A1 | 5/2007 | Imbach et al. |
| 2007/0111933 A1 | 5/2007 | Kopchick et al. |
| 2007/0179178 A1 | 8/2007 | Buettelmann et al. |
| 2007/0218135 A1 | 9/2007 | Mukharya et al. |
| 2007/0289310 A1 | 12/2007 | Dooley et al. |
| 2008/0004308 A1 | 1/2008 | Dhanak et al. |
| 2008/0081781 A1 | 4/2008 | Lippa et al. |
| 2008/0305113 A1 | 12/2008 | Kwon et al. |
| 2009/0012064 A1 | 1/2009 | Sagara et al. |
| 2009/0238828 A1 | 9/2009 | Munzert et al. |
| 2009/0280115 A1 | 11/2009 | Maier et al. |
| 2009/0281191 A1 | 11/2009 | Rangwala et al. |
| 2010/0041643 A1 | 2/2010 | Adachi et al. |
| 2010/0227838 A1 | 9/2010 | Shah et al. |
| 2010/0249412 A1 | 9/2010 | Linz et al. |
| 2010/0286127 A1 | 11/2010 | Miyoshi et al. |
| 2011/0028405 A1 | 2/2011 | Harrison et al. |
| 2011/0098288 A1 | 4/2011 | Major et al. |
| 2011/0143651 A1 | 6/2011 | Marocchi et al. |
| 2011/0172231 A1 | 7/2011 | Baenteli et al. |
| 2011/0201606 A1 | 8/2011 | Garcia-Echeverria et al. |
| 2011/0212077 A1 | 9/2011 | Noronha et al. |
| 2011/0245245 A1 | 10/2011 | Mortensen et al. |
| 2012/0014979 A1 | 1/2012 | Dent |
| 2012/0040961 A1 | 2/2012 | Gray et al. |
| 2012/0202798 A1 | 8/2012 | Sagara et al. |
| 2012/0244209 A1 | 9/2012 | Roth et al. |
| 2012/0329803 A1 | 12/2012 | Linz et al. |
| 2013/0184264 A1 | 7/2013 | Bradner et al. |
| 2013/0210813 A1 | 8/2013 | Bradner et al. |
| 2013/0245013 A1 | 9/2013 | Mohr et al. |
| 2013/0252331 A1 * | 9/2013 | Bradner ............... A61K 31/00 435/375 |
| 2013/0261109 A1 | 10/2013 | Miyoshi et al. |
| 2013/0274239 A1 | 10/2013 | Gangloff et al. |
| 2013/0280332 A1 | 10/2013 | Moss et al. |
| 2014/0011862 A1 | 1/2014 | Bradner et al. |
| 2014/0243322 A1 | 8/2014 | Arnold et al. |
| 2015/0054642 A1 | 2/2015 | Carruthers |
| 2015/0335656 A1 | 11/2015 | Miyoshi et al. |
| 2016/0033519 A1 | 2/2016 | Bradner et al. |
| 2016/0168154 A1 | 6/2016 | Marineau et al. |
| 2016/0231314 A1 | 8/2016 | Ryan et al. |
| 2016/0279141 A1 | 9/2016 | Bradner et al. |
| 2016/0332993 A1 | 11/2016 | Bradner et al. |
| 2016/0347749 A1 | 12/2016 | Bradner et al. |
| 2017/0008895 A1 | 1/2017 | Bradner et al. |
| 2017/0029437 A1 | 2/2017 | Bradner et al. |
| 2017/0209461 A1 | 7/2017 | Landau et al. |
| 2017/0333444 A1 | 11/2017 | Landau et al. |
| 2017/0360801 A1 | 12/2017 | Sotomayor et al. |
| 2018/0193350 A1 | 7/2018 | Landau et al. |
| 2018/0222917 A1 | 8/2018 | Bradner et al. |
| 2018/0237454 A1 | 8/2018 | Bradner et al. |

FOREIGN PATENT DOCUMENTS

| | | |
|---|---|---|
| CH | 622019 A5 | 3/1981 |
| CN | 1227555 A | 9/1999 |
| CN | 100348600 C | 11/2007 |
| CN | 101910182 A | 12/2010 |
| CN | 103037865 A | 4/2013 |
| DE | 3724164 A1 | 1/1988 |
| EP | 0 087 850 A1 | 9/1983 |
| EP | 0 368 175 A1 | 5/1990 |
| EP | 0 387 613 A1 | 9/1990 |
| EP | 0 934 940 A1 | 8/1999 |
| EP | 0 989 131 A1 | 3/2000 |
| EP | 1 297 836 A1 | 4/2003 |
| EP | 1 887 008 A1 | 2/2008 |
| EP | 2 239 264 A1 | 10/2010 |
| FR | 2329668 A1 | 5/1977 |
| JP | 1-299231 | 12/1989 |
| JP | 6-157316 | 6/1994 |
| JP | H10500998 A | 1/1998 |
| JP | 11-228576 | 8/1999 |
| JP | 11-512107 | 10/1999 |
| JP | 3001979 B2 | 1/2000 |
| JP | 3096299 B2 | 10/2000 |
| JP | 2006519236 A | 8/2006 |
| JP | 2008/156311 A | 7/2008 |
| JP | 2013510123 A | 3/2013 |
| JP | 2013/532130 A | 8/2013 |
| JP | 5913292 B2 | 4/2016 |
| JP | 61-87684 B2 | 8/2017 |
| KR | 10-2000-0016732 | 3/2000 |
| RU | 2294761 C2 | 3/2007 |
| TW | 201217382 A | 5/2012 |
| WO | WO-97/13537 A1 | 4/1997 |
| WO | WO-97/37705 A1 | 10/1997 |
| WO | WO-97/47622 A1 | 12/1997 |
| WO | WO-98/11111 A1 | 3/1998 |
| WO | WO-99/34850 A1 | 7/1999 |
| WO | WO-01/95912 A1 | 12/2001 |
| WO | WO-2006/129623 A1 | 12/2006 |
| WO | WO-2007/056117 A1 | 5/2007 |
| WO | WO-2007/095188 A2 | 8/2007 |
| WO | WO-2008/083056 A2 | 7/2008 |
| WO | WO-2008/137081 A1 | 11/2008 |
| WO | WO-2009/084693 A1 | 7/2009 |
| WO | WO-2010/015387 A1 | 2/2010 |
| WO | WO-2010/049466 A1 | 5/2010 |
| WO | WO-2011/054553 A1 | 5/2011 |
| WO | WO-2011/054841 A1 | 5/2011 |
| WO | WO-2011/054843 A1 | 5/2011 |
| WO | WO-2011/054844 A1 | 5/2011 |
| WO | WO-2011/054845 A1 | 5/2011 |
| WO | WO-2011/054846 A1 | 5/2011 |
| WO | WO-2011/054848 A1 | 5/2011 |
| WO | WO-2011/143657 A1 | 11/2011 |
| WO | WO-2011/143660 A2 | 11/2011 |
| WO | WO-2011/143669 A2 | 11/2011 |
| WO | WO 2011143651 A1 * | 11/2011 ............. A61K 31/00 |
| WO | WO-2011/161031 A1 | 12/2011 |
| WO | WO-2011/162845 A1 | 12/2011 |
| WO | WO-2012/050907 A2 | 4/2012 |
| WO | WO-2012/075383 A2 | 6/2012 |
| WO | WO-2012/075456 A1 | 6/2012 |
| WO | WO-2012095505 A1 | 7/2012 |
| WO | WO-2012/116170 A1 | 8/2012 |
| WO | WO-2012/118812 A2 | 9/2012 |
| WO | WO-2013/019710 A2 | 2/2013 |
| WO | WO-2013/030450 A1 | 3/2013 |
| WO | WO-2013/033268 A2 | 3/2013 |
| WO | WO-2013/033269 A1 | 3/2013 |
| WO | WO-2013/033270 A2 | 3/2013 |
| WO | WO-2013/033420 A1 | 3/2013 |
| WO | WO-2013/030150 A | 7/2013 |
| WO | WO-2013/097601 A1 | 7/2013 |
| WO | WO-2013/148197 A1 | 10/2013 |
| WO | WO-2013/192274 A2 | 12/2013 |
| WO | WO-2014/068402 A2 | 5/2014 |
| WO | WO-2014/071247 A1 | 5/2014 |
| WO | WO-2014/128070 A1 | 8/2014 |
| WO | WO-2014/128111 A1 | 8/2014 |
| WO | WO-2014/134583 A2 | 9/2014 |
| WO | WO-2014/144721 A2 | 9/2014 |
| WO | WO-2014/159392 A1 | 10/2014 |
| WO | WO-2014/193951 A1 | 12/2014 |
| WO | WO-2015/018521 A1 | 2/2015 |
| WO | WO-2015/018522 A1 | 2/2015 |
| WO | WO-2015/023938 A1 | 2/2015 |
| WO | WO-2015/054642 A2 | 4/2015 |
| WO | WO-2015/070020 A2 | 5/2015 |
| WO | WO-2015/081284 A1 | 6/2015 |
| WO | WO-2015/131113 A1 | 9/2015 |
| WO | WO-2016/069578 A1 | 5/2016 |

(56) References Cited

FOREIGN PATENT DOCUMENTS

WO  WO-2016/210275 A1  12/2016
WO  WO-2017/059319 A2  4/2017

OTHER PUBLICATIONS

Final Rejection for U.S. Appl. No. 13/697,963, "Compositions and Methods for Modulating Metabolism," dated Jan. 18, 2017.
Final Rejection for U.S. Appl. No. 13/934,843, "Compositions and Methods for Treating Leukemia," dated Oct. 30, 2015.
Non-Final Rejection for U.S. Appl. No. 13/697,963, "Compositions and Methods for Modulating Metabolism," dated May 31, 2016.
Non-Final Rejection for U.S. Appl. No. 13/934,843, "Compositions and Methods for Treating Leukemia," dated Jan. 25, 2017.
Non-Final Rejection for U.S. Appl. No. 14/977,343, "Male Contraceptive Compositions and Methods of Use," dated Aug. 24, 2016.
Non-Final Rejection for U.S. Appl. No. 15/034,922, "Combination Therapy for Cancer Using Bromodomain and Extra-Terminal (Bet) Protein Inhibitors," dated Mar. 8, 2018.
Non-Final Rejection for U.S. Appl. No. 15/061,576, "Compositions and Methods for Treating Neoplasia, Inflammatory Disease and Other Disorders," dated Aug. 2, 2017.
Notice of Allowance for U.S. Appl. No. 14/977,343, "Male Contraceptive Compositions and Methods of Use," dated Jun. 16, 2017.
Notice of Allowance for U.S. Appl. No. 13/698,006, "Male Contraceptive Compositions and Methods of Use," dated Sep. 3, 2015.
Notice of Allowance for U.S. Appl. No. 13/934,843 dated Jul. 13, 2017.
notice of Allowance for U.S. Appl. No. 14/977,343, "Male Contraceptive Compositions and Methods of Use," dated Feb. 13, 2017.
Notice of Allowance, U.S. Appl. No. 13/698,010, dated Aug. 21, 2014.
Notice of Allowance, U.S. Appl. No. 14/502,840, dated Dec. 4, 2015.
Office Action, U.S. Appl. No. 13/697,963, dated Nov. 21, 2014.
Office Action, U.S. Appl. No. 13/698,006, dated Apr. 10, 2014.
Office Action, U.S. Appl. No. 13/698,006, dated Oct. 23, 2014.
Office Action, U.S. Appl. No. 13/698,006, dated Sep. 26, 2013.
Office Action, U.S. Appl. No. 13/934,843, dated Mar. 23, 2015.
Office Action, U.S. Appl. No. 15/522,222, dated Mar. 2, 2018.
Requirement for Restriction/Election for U.S. Appl. No. 13/697,963, "Compositions and Methods for Modulating Metabolism," dated Mar. 20, 2014.
Requirement for Restriction/Election for U.S. Appl. No. 13/934,843, "Compositions and Methods for Treating Leukemia," dated Jul. 1, 2014.
Requirement for Restriction/Election for U.S. Appl. No. 15/034,922, "Combination Therapy for Cancer Using Bromodomain and Extra-Terminal (BET) Protein Inhibitors," dated Apr. 21, 2017.
Requirement for Restriction/Election for U.S. Appl. No. 15/061,576, "Compositions and Methods for Treating Neoplasia, Inflammatory Disease and Other Disorders," dated Feb. 15, 2017.
Abbate, et al., "Structure of the papillomavirus DNA-tethering complex E2:Brd4 and a peptide that ablates HPV chromosomal association," Mol Cell, 24(6): 877-889, (2006).
Acosta et al., "Amifostine Impairs p53-mediated Apoptosis of Human Myeloid Leukemia Cells," Molecular Cancer Therapeutics, 2: 893-900 (2003).
Anders et al., "Genome-wide Localization of Small Molecules," Nat Biotechnol, 32(1): 92-96 (2014).
Arango, et al., "Reversible Azoospermia in a Patient Treated with Triazolam," Eur J Contracept Reprod Health Care, 1(3): 293-294 (1996).
Bartholomeeusen et al., "Bromodomain and Extra-terminal (BET) Bromodomain Inhibition Activate Transcription via Transient Release of Positive Transcription Elongation Factor b (P-TEFb) from 7SK Small Nuclear Ribonucleoprotein," J Biol Chem, 287(43): 36609-36619 (2012).

Baud et al., "Chemical Biology. A Bump-and-hole Approach to Engineer Controlled Selectivity of BET Bromodomain Chemical Probes," Science, 346(6209): 638-641 (2014).
Berge et al., "Pharmaceutical Salts," J Pharm Sci, 66(1): 1-19 (1977).
Berkovits, et al., "The First Bromodomain of the Testis-Specific Double Bromodomain Protein Brdt is Required for Chromocenter Organization That is Modulated by Genetic Background," Dev Biol, 360(2): 358-368 (2011).
Berkovits, et al., "The Role of the Double Bromodomain-Containing BET Genes During Mammalian Spermatogenesis," Curr Top Dev Biol, 102: 293-326 (2013).
Buchdunger, et al., "Inhibition of the Abl Protein-Tyrosine Kinase In Vitro and In Vivo by a 2-Phenylaminopyrimidine Derivative," Cancer Res, 56(1): 100-104 (1996).
Buchdunger, et al., "Selective inhibition of the platelet-derived growth factor signal transduction pathway by a protein-tyrosine kinase inhibitor of the 2-phenylaminopyrimidine class," Proc Natl Acad Sci, 92(7): 2558-2562 (1995).
Bullock, et al., "Structural basis of Inhibitor Specificity of the Human Protooncogene Proviral Insertion site in Moloney Murine lLeukemia virus (PIM-1) kinase," J Med Chem, 48(24): 7604-7614 (2005).
Cellai, et al., "Mechanistic Insight Into WEB-2170-induced Apoptosis in Human Acute Myelogenous Leukemia Cells: the Crucial Role of PTEN," Exp Hematol, 37(10): 1176-1185 (2009).
Cellai, et al., "Specific PAF Antagonist WEB-2086 Induces Terminal Differentiation of Murine and Human Leukemia Cells," FASEB, 16(7): 733-735 (2002).
Chaidos et al., "Protent Antimyeloma Activity of the Novel Bromodomain Inhibitors I-BET151 and I-BET762," Blood, 123(5): 697-705 (2014).
Cheng et al., "Adjudin Disrupts Spermatogenesis via the Action of Some Unlikely Partners: Eps8, Arp2/3 complex, drebrin E, PAR6 and 14-3-3," Spermatogenesis, 1(4): 291-297 (2011).
Chesi et al., "Drug Response in a Genetically Engineered Mouse Model of Multiple Myeloma is Predictive of Clinical Efficacy," Blood, 120(2): 376-385 (2012).
Choi et al., "Brain Penetrant LRRK2 Inhibitor," ACS Med Chem Lett, 3(8): 658-662 (2012).
Cole, "Chemical probes for histone-modifying enzymes," Nat Chem Biol, 4: 590-597 (2008).
Crawford, et al., "Bromodomain 4 activation predicts breast cancer survival," Proc Natl Acad Sci, 105(17): 6380-6385 (2008).
Dawson et al., "Inhibition of BET Recruitment to Chromatin as an Effective Treatment for MLL-fusion Leukaemia," Nature, 478(7370): 529-533 (2011).
Delbroek et al., "Development of an Enzyme-linked Immunosorbent Assay for Detection of Cellular and in Vivo LRRK2 S935 Phosphorylation," J Pharm Biomed Anal, 76: 49-58 (2013).
Delmore et al., "BET Bromodomain Inhibition as a Terapeutic Strategy to Target c-Myc," cell, 146(6): 904-917 (2011).
Deng et al., "Structural Determinants for ERK5 (MAPK7) and Leucine Rich Repeat Kinase 2 Activities of Benzo[e]pyrimido-[5,4-b]diazepine-6(11H)-ones," Eur J Med Chem, 70: 758-767 (2013).
Denis, et al., "An Emerging Role for Bromodomain-Containing Proteins in Chromatin Regulation and Transcriptional Control of Adipogenesis," FEBS Lett, 584(15): 3260-3268 (2010).
Dey, et al., "Brd4 Marks Select Genes of Mitotic Chromatin and Directs Postmitotic Transcription," Mol Biol Cell, 20(23): 4899-4909 (2009).
Druker, et al., "Effects of a selective inhibitor of the Abl Tyrosine kinase on the Growth of BuAbl positive cells," Nat Med, 2(5): 561-566 (1996).
Druker, et al., "Efficacy and safety of a specific inhibitor of the BCR-ABL tyrosine kinase in chronic myeloid leukemia," N Engl J Med, 344: 1031-1037 (2001).
Elkins et al., "X-ray Crystal Structure of ERK5 (MAPK7) in Complex with a Specific Inhibitor," J Med Chem, 56(11): 4413-4421 (2013).
Examination Report, AU Application No. 2011252808, dated Aug. 5, 2013.

(56) References Cited

OTHER PUBLICATIONS

Extended European Search Report for European Patent Application No. 14860080.2 dated May 3, 2017.
Fedorov, et al., "A Systematic Interaction Map of Validated Kinase Inhibitors with Ser/Thr kinases," Proc Natl Acad Sci, 104(51): 20523-20528 (2007).
Filippakopoulos et al., "Targeting Bromodomains: Epigenetic Readers of Lysine Acetylation," Nat Rev Drug Discov, 13(5): 337-356 (2014).
Filippakopoulos, et al., "Selective Inhibition of BET Bromodomains," Nature, 468(7327): 1067-1073 (2010).
French, "Demystified Molecular pathology of NUT Midline Carcinomas," J Clin Pathol, 63: 492-496 (2010).
French, et al. "BRD4-NUT Fusion Oncogene: a Novel Mechanism in Aggressive Carcinoma," Cancer Res, 63(2): 304-307 (2003).
French, et al., "BRD-NUT Oncoproteins: a Family of Closely Related Nuclear Proteins that Block Epithelial Differentiation and Maintain the Growth of Carcinoma Cells," Oncogene, 27: 2237-2242 (2008).
French, et al., "BRD4 Bromodomain Gene Rearrangement in Aggressive Carcinoma with Translocation t(15;19)," Am J Pathol, 159(6): 1987-1992 (2001).
Genbank Submission; NH/NCBI, Accession No. H86170. Hillier et al., Nov. 21, 1995. 2 pages.
Genbank Submission; NH/NCBI, Accession No. NP_004597. Herzfeld et al., Aug. 26, 2016. 5 pages.
Genbank Submission; NH/NCBI, Accession No. NP_005095. Xiao et al., Oct. 6, 2016. 4 pages.
Genbank Submission; NH/NCBI, Accession No. NP_009168. DiBernardo et al., Sep. 28, 2008. 2 pages.
Genbank Submission; NH/NCBI, Accession No. NP_031397. Shao et al., Jan. 4, 2017. 4 pages.
Genbank Submission; NH/NCBI, Accession No. NP_060404. Bezrookove et al., Oct. 7, 2016. 5 pges.
Genbank Submission; NH/NCBI, Accession No. NP_612411. Saare et al., Aug. 25, 2016. 2 pages.
Genbank Submission; NH/NCBI, Accession No. NP_872579. Lee et al., Oct. 6, 2016. 4 pages.
Greenwald, et al., "Eµ-BRD2 Transgenic Mice Develop B-Cell Lymphoma and Leukemia," Blood, 103(4): 1475-1484 (2004).
Haack, et al., "Diagnosis of NUT Midline Carcinoma Using a NUT-specific Monoclonal Antibody," Am J Surg Pathol, 33(7): 984-991 (2009).
He et al., "The Histone Methyltransferase Ezh2 is a Crucial Epigenetic Regulator of Allogeneic T-cell Responses Mediating Graft-versus-host Disease," Blood, 122(25): 119-128 (2013).
Hedrington et al., "Effects of Antecedent GABAA Activation with Alprazolam on Counterregulatory Responses to Hypoglycemia in Healthy Humans," Diabetes, 59(4): 1074-1081 (2010).
Houzelstein et al., "Growth and Early Postimplantation Defects in Mice Deficient for the Bromodomain-containing Protein Brd4," Mol Cell Biol, 22(11): 3794-3802 (2002).
Hsu et al., "Metabolic Syndrome, Hyperinsulinemia and Cancer," The American Journal of Clinical Nutrition, 86(3): 867S-871S (2007).
Hu, et al., "Adjudin Targeting Rabbit Germ Cell Adhesion as a Male Contraceptive: A Pharmacokinetics Study," J Androl, 30(1): 87-93 (2009).
Huang, et al., "Brd4 Coactivates Transcriptional Activation of NF-κB via Specific Binding to Acetylated RelA," Mol Cell Biol, 29(5): 1375-1387 (2009).
International Preliminary Report for International Application No. PCT/US14/64549 dated May 10, 2016.
International Preliminary Report on Patentability for International Application No. PCT/US2015/018118 dated Sep. 6, 2016.
International Preliminary Report on Patentability for International Application No. PCT/US2015/057538 dated May 2, 2017.
International Preliminary Report on Patentability for International Application No. PCT/US2016/039270 dated Dec. 26, 2017.
International Preliminary Report on Patentability for PCT/US2014/023386, dated Sep. 24, 2015.
International Preliminary Report on Patentability for PCT/US2014/48230, dated Feb. 4, 2016.
International Preliminary Report on Patentability for PCT/US2015/044180, dated Feb. 23, 2017.
International Preliminary Report on Patentability for PCT/US2015/044303, dated Feb. 23, 2017.
International Preliminary Report on Patentability for PCT/US2015/14039, dated Aug. 11, 2016.
International Preliminary Report on Patentability for PCT/US2015/14044, dated Aug. 11, 2016.
International Preliminary Report on Patentability for PCT/US2015/14109, dated Aug. 11, 2016.
International Preliminary Report on Patentability for PCT/US2015/14120, dated Aug. 11, 2016.
International Search Report and Written Opinion for International Application No. PCT/US14/64549 dated Mar. 11, 2015.
International Search Report and Written Opinion for International Application No. PCT/US2015/018118 dated May 19, 2015.
International Search Report and Written Opinion for International Application No. PCT/US2015/057538 dated Jan. 21, 2016.
International Search Report and Written Opinion for International Application No. PCT/US2016/039270 dated Oct. 18, 2016.
International Search Report and Written Opinion for PCT/US2014/023386, dated Jul. 9, 2014.
International Search Report and Written Opinion for PCT/US2014/14120, dated Apr. 23, 2015.
International Search Report and Written Opinion for PCT/US2014/48230, dated Jan. 30, 2015.
International Search Report and Written Opinion for PCT/US2015/044180, dated Nov. 5, 2015.
International Search Report and Written Opinion for PCT/US2015/044303, dated Dec. 31, 2015.
International Search Report and Written Opinion for PCT/US2015/059551, dated Jan. 13, 2016.
International Search Report and Written Opinion for PCT/US2015/059622, dated Mar. 30, 2016.
International Search Report and Written Opinion for PCT/US2015/14039, dated Apr. 23, 2015.
International Search Report and Written Opinion for PCT/US2015/14044, dated Apr. 23, 2015.
International Search Report and Written Opinion for PCT/US2015/14109, dated Jul. 6, 2015.
International Search Report and Written Opinion for PCT/US2016/051017, dated Jan. 10, 2017.
International Search Report and Written Opinion for PCT/US2016/051107, dated Nov. 22, 2016.
Kadota, et al. "Identification of Novel Gene Amplifications in Breast Cancer and Coexistence of Gene Amplification With an Activating Mutation of PIK3CA," Cancer Res, 69(18): 7357-7365 (2009).
Kavanagh et al., "The Development of CNS-active LRRK2 Inhibitors Using Property-directed Optimisation," Bioorg Med Chem Lett, 23(13): 3690-3696 (2013).
Kim, et al., "Berberine Improves Lipid Dysregulation in Obesity by Controlling Central and Peripheral AMPK Activity," Am J Physiol Endocrinol Metab, 296(4): E812-E819 (2009).
Konze et al., "An Orally Bioavailable Chemical Probe of the Lysine Methyltransferases EZH2 and EZH1," ACS Chem Biol, 8(6): 1324-1334 (2013).
Krueger et al., "The Mechanism of Release of P-TEFb and HEXIM1 from the 7SK snRNP by Viral and Cellular Activators Includes a Conformational change in 7SK," PLoS One, 5(8): e12335 (2010).
Lawless, et al., "Histone Deacetylase Inhibitors Target Diabetes via Chromatin Remodeling or as Chemical Chaperones?" Curr Diabetes Rev, 5(3): 201-209 (2009).
Le Coutre, et al., "In vivo eradication of human BCR/ABL-positive leukemia cells with an ABL kinase inhibitor," J Natl Cancer Inst, 91(2): 163-168 (1999).
Lee et al., "Synergistic Effect of JG1 and Rapamycin for Treatment of Human Osteosarcoma," Int J Cancer, 136(9): 2055-2064 (2014).

(56) References Cited

OTHER PUBLICATIONS

Lee, et al., "Berberine, a Natural Plant Product, Activates AMP-Activated Protein Kinase with Beneficial Metabolic Effects in Diabetic and Insulin-Resistant States," Diabetes, 55(8): 2256-2264 (2006).
Lotti et al., "Ultrasound of the Male Genital Tract in Relation to Male Reproductive Health," Hum Reprod Update, 21(1): 56-83 (2015).
Marushige, "Activation of Chromatin by Acetylation of Histone Side Chains," Proc Natl Acad Sci, 73(11): 3937-3941 (1976).
Matzuk, et al., "Small-Molecule Inhibition of BRDT for Male Contraception," Cell, 150(4): 673-684 (2012).
McKeown et al., "Biased Multicomponent Reactions to Develop Novel Bromodomain Inhibitors," J Med Chem, 57(21): 9019-9027 (2014).
Meguro, et al., "Heterocycles. VI.1) Synthesis of 4H-s-Triazolo[4,3-α][1,4]benzodiazepines, Novel Tricyclic Psychosedatives," Chem Pharm Bull, 21(11): 2382-2390 (1973).
Meng-er, et al., "Use of All-Trans Retinoic Acid in the Treatment of Acute Promyelocytic Leukemia," Blood, 72(2): 567-572 (1988).
Mertz et al., "Targeting MYC Dependence in Cancer by Inhibiting Bet Bromodomains," PNAS, 108(40): 16669-16674 (2011).
Mochizuki, et al., "The Bromodomain Protein Brd4 Stimulates G1 Gene Transcription and Promotes Progression to S Phase," J Biol Chem, 283(14): 9040-9048 (2008).
Moros et al., "Synergistic Anti-tumor Activity of Lenalidomide with the BET Bromodomain Inhibitor CPI203 in Bortezomib-resistant Mantle Cell Lymphoma," Leukemia 28(10): 2049-2059 (2014).
Niesen, et al., "The use of Differential Scanning Fluorimetry to Detect Ligand Interactions that Promote Protein Stability," Nat Protoc, 2(9): 2212-2221 (2007).
Nishimura et al., "Fertility and Reproduction Studies of Apafant (WEB 2086 BS) in Rats Dosed Orally," Oyo Yakuri/Pharmacometrics, 52(3/4): 185-200 (1996).
Notification Concerning Transmittal of International Preliminary Report on Patentability, International Application No. PCT/US2011/036647, Titled: "Compositions and Methods of Modulating Metabolism", dated Nov. 29, 2012.
Notification Concerning Transmittal of International Preliminary Report on Patentability, International Application No. PCT/US2011/036667, Titled: "Male Contraceptive Compositions and Methods of Use", dated Nov. 29, 2012.
Notification Concerning Transmittal of International Preliminary Report on Patentability, International Application No. PCT/US2011/036672, Titled: "Compositions and Methods for Treating Leukemia", dated Nov. 29, 2012.
Notification Concerning Transmittal of International Preliminary Report on Patentability, International Application No. PCT/US2011/036701, Titled: "Compositions and Methods for Treating Neoplasia, Inflammatory Disease and Other Disorders", dated Nov. 29, 2012.
Notification of Transmittal of the International Search Report and the Written Opinion of the International Searching Authority, International Application No. PCT/US11/36647, Titled: "Compositions and Methods of Modulating Metabolism", dated Aug. 17, 2011.
Notification of Transmittal of the International Search Report and the Written Opinion of the International Searching Authority, International Application No. PCT/US11/36667, Titled: "Male Contraceptive Compositions and Methods of Use", dated Aug. 15, 2011.
Notification of Transmittal of the International Search Report and the Written Opinion of the International Searching Authority, International Application No. PCT/US11/36672, Titled: "Compositions and Methods for Treating Leukemia", dated Jan. 27, 2012.
Notification of Transmittal of the International Search Report and the Written Opinion of the International Searching Authority, International Application No. PCT/US11/36701, Titled: "Compositions and Methods for Treating Neoplasia, Inflammatory Disease and Other Disorders", dated Feb. 1, 2012.
Owen, et al., "The Structural Basis for the Recognition of Acetylated Histone R4 by the Bromodomain of Histone Acetyltransferase Gcn5p," The EMBO Journal, 19(22): 6141-6149 (2000).

Patani, et al., "Bioisosterism: A Rational Approach in Drug Design," Chem Rev, 96(8): 3147-3176 (1996).
Phelps, et al., "Clinical Response and Pharmacokinetics from a Phase 1 Study of an Active Dosing Schedule of Flavopiridol in Relapsed Chronic Lymphocytic Leukemia," Blood, 113(12): 2637-2645 (2009).
Preisler, et al., "Assessment of c-myc Expression in Individual Leukemic Cells," Leuk Res, 12(6): 507-516 (1988).
Ptashne, "Binding Reactions: Epigenetic Switches, Signal Transduction and Cancer," Curr Biol, 19(6): R234-R241 (2009).
PubChem CID 5325760. Published Jan. 25, 2006.
PubChem CID-55504609. Created Jan. 25, 2012.
PubChem CID-56267130. Created Jan. 25, 2012.
PubChem SID 225027960. Available date/deposit date: Feb. 2, 2015.
PubChem SID 235048169. Feb. 13, 2015.
PubChem SID 235671906. Feb. 13, 2015.
Quinn, et al., "A homogeneous method for investigation of methylation-dependent protein-protein interactions in epigenetics," Nucleic Acids Res, 38(2): e11(1-10) (2010).
Rahl, et al., "c-Myc Regulates Transcriptional Pause Release," Cell, 141(3): 432-445 (2010).
Rhein et al., "CD11b is a Therapy Resistance and Minimal Residual Disease-Specific Marker in Precursor B-cell Acute Lymphoblastic Leukemia," Blood, 115(18): 3763-3771 (2010).
Roberts et al., "A Bead-Based Proximity Assay for BRD4 Ligand Discovery," Curr Protoc Chem Biol, 7(4): 263-278 (2015).
Santillan, et al., "Bromodomain and Histone Acetyltransferase Domain Specificities Control Mixed Lineage Leukemia Phenotype," Cancer Res, 66(20): 10032-10039 (2006).
Schindler, et al. "Structural mechanism for STI-571 Inhibition of Abelson Tyrosine kinase. Science," 289(5486): 1938-1942 (2000).
Schreiber, et al., "Signaling Network Model of Chromatin," Cell, 111(6): 771-778 (2002).
Schroder et al., "Two-pronged Binding with Bromodomain-containing Protein 4 Liberates Positive Transcription Elongation Factor B from Inactive Ribonucleoprotein Complexes," J Biol Chem, 287(2): 1090-1099 (2012).
Seyrig, et al., "Effects of a Chronic Administration of Two Benzodiazepines on Food Intake in Rats Given a Highly Palatable Diet," Pharmacology Biochemistry & Behavior, 25(4): 913-918 (1986).
Shang, et al., "The First Bromodomain of Brdt, a Testis-Specific Member of the BET Sub-Family of Double-Bromodomain-Containing Proteins, is Essential for Male Germ Cell Differentiation," Development, 134: 3507-3515 (2007).
Smith et al., "The Bromodomain: A New Target in Emerging Epigenetic Medicine," ACS Chem Biol, 11(3): 598-608 (2016).
Souers et al., "ABT-199, a Potent and Selective BCL-2 Inhibitor, Achieves Antitumor Activity While Sparing Platelets," Nature Medicine, 19(2): 202-210 (2013).
Tanaka et al., "Inhibitors of Emerging Epigenetic Targets for Cancer Therapy: A Patient Review (2010-2014)," Pharm Pat Anal, 4(4): 261-284 (2015).
Taskinen, et al., "A High Tumor-Associated Macrophage Content Predicts Favorable Outcome in Follicular Lymphoma Patients Treated with Rituximab and Cyclophosphamide-Doxorubicin-Vincristine-Prednisone," Clin Cancer Res, 13(19): 5784-5785 (2007).
Tse et al., "ABT-263: A Potent and Orally Bioavaliable Bcl-2 Family Inhibitor," Cancer Res, 68(9): 3421-3428 (2008).
Verma et al., "Identification of Potent, Selective, Cell-Active Inhibitors of the Histone Lysine Methyltransferase EZH2," ACS Med Chem Lett, 3(12): 1091-1096 (2012).
Vollmuth, et al., "Structures of the dual bromodomains of the P-TEFb-activating protein Brd4 at atomic resolution," J Biol Chem, 284(52): 36547-36556 (2009).
VonVoigtlander, et al., "Alprazolam: Review of Pharmacological, Pharmacokinetic and Clinical Data," Drug Dev Res, 6(1): 1-12 (1985).
Wang et al., "Activation of SOX2 Expression BRD4-NUT Oncogenic Fusion Drives Neoplastic Transformation in NUT Midline Carcinoma," Cancer Research, 74(12): 3332-3343 (2014).

(56) References Cited

OTHER PUBLICATIONS

Wang, et al., "A Seamless Trespass: Germ Cell Migration Across the Seminiferous Epithelium During Spermatogenesis," J Cell Biol, 178(4): 549-556 (2007).

Wang, et al., "Brd2 Disruption in Mice Causes Severe Obesity Without Type 2 Diabetes," Biochem J, 425(1): 71-83 (2010).

Wass et al., "Crizotinib in ALK-Positive Diffuse Large B-Cell Lymphoma: A Case Report," Blood, 120(21): 4862 (2012).

Wehner et al., "Effects of Natlizumab, an Alpha4 Integrin Inhibitor, on Fertility in Male and Female Guinea Pigs," Birth Defects Res B Dev Reprod Toxicol, 86(2): 108-116 (2009).

Yang, "Multisite Protein Modification and Intramolecular Signaling," Oncogene, 24: 1653-1662 (2005).

Yang, et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo," Blood, 110(6): 2034-2040 (2007).

Yang, et al., "Brd4 recruits P-TEFb to chromosomes at late mitosis to promote G1 gene expression and cell cycle progression," Mol Cell Biol, 28(3): 967-976 (2008).

Yang, et al., "Recruitment of P-TEFb for Stimulation of Transcriptional Elongation by the Bromodomain Protein Brd4," Mol Cell, 16(4): 535-545 (2005).

You, et al., "Kaposi's sarcoma-associated herpesvirus latency-associated nuclear antigen interacts with bromodomain protein Brd4 on host mitotic chromosomes," J Virol, 80(18): 8909-8919 (2006).

You, et al., "Regulation of Aurora B Expression by the Bromodomain Protein Brd4," Mol Cell Biol, 29: 5094-5103 (2009).

Zeng, et al., "Bromodomain: an Acetyl-lysine Binding Domain," FEBS Lett, 513(1): 124-128 (2002).

Zhang, et al., "Down-Regulation of NF-κB Transcriptional Activity in HIV-Associated Kidney Disease by BRD4 Inhibition," J Biol Chem, 287(34): 28840-28851 (2012).

Zhang, et al., "Down-Regulation of NF-κB Transcriptional Activity in HIV-Associated Kidney Disease by BRD4 Inhibition," J Biol Chem, 287(46): 38956 (2012).

Zhao, et al., "Research Development on Fusion Protein Transcription Factor siRNA Specifically Targeting Leukemia," Sciencepaper Online: 1-6 and J Med Res, 39(2): 6-9 (2010) (English-language translation entitled "Progress of Research on siRNA that Targets Leukemia Specific Transcription Regulation Factor Fusion Proteins," 1-10).

Zuber, et al., "RNAi Screen Identifies Brd4 as a Therapeutic Target in Acute Myeloid Leukaemia," Nature, 478(7370): 524-528 (2011), with "Supplementary Information" from www.nature.com/nature/journal/v478/n7370/extref/nature10334-s1.pdf, pp. 1-33.

Zuercher et al., "Identification and Structure-activity Relationship of Phenolic Acyl Hydrazones as Selective Agonists for the Estrogen-related Orphan Nuclear Receptors ERRbeta and ERRgamma," J Med Chem, 48(9): 107-109 (2005).

Dittmann et al., "The Commonly Used PI3-Kinase Probe LY294002 Is an Inhibitor of BET Bromodomains," ACS Chem Biol, 9(2):495-502 (2014).

International Preliminary Report on Patentability for International Application No. PCT/US2016/054924 dated Apr. 3, 2018.

International Search Report and Written Opinion for International Application No. PCT/US2016/054924 dated Sep. 5, 2017.

Lee et al., "Synergistic effect of JQ1 and rapamycin for treatment of human osteosarcoma," Int J Cancer, 136(9):2055-2064 (2014).

Loven et al., "Selective Inhibition of Tumor Oncogenes by Disruption of Super-Enhancers," Cell 153: 320-334 (2013).

Moros et al., "Synergistic antitumor activity of lenalidomide with the BET bromodomain inhibitor CPI203 in bortezomib-resistant mantle cell lymphoma," Leukemia, 28: 2049-2059 (2014).

Notice of Allowance for U.S. Appl. No. 15/886,559, "Compositions and Methods for Treating Neoplasia, Inflammatory Disease and Other Disorders," dated Apr. 23, 2019.

Belkina et al., "BET Protein Function Is Required for Inflammation: Brd2 Genetic Disruption and BET Inhibitor JQ1 Impair Mouse Macrophage Inflammatory Responses," J Immunol 190:3670-3678 (2013).

Bendas et al., "Cancer Cell Adhesion and Metastasis: Selectins, Integrins, and the Inhibitory Potential of Heparins," International Journal of Cell Biology, 2012:1-10 (2012).

Braun et al., "Preclinical Study of the Bromodomain Inhibitor OTX015 in Acute Myeloid (AML) and Lymphoid (ALL) Leukemias," Blood 122:4218 (2013).

Laubli et al., "L-Selectin Facilitation of Metastasis Involves Temporal Induction of Fut7-Dependent Ligands at Sites of Tumor Cell Arrest," Cancer Res 66(3):1536-1542 (2006).

Novus Biologicals, "CD11 b Expression, Leukocyte Adhesion and the Innate Immune System," Nobusbio.com, (2011).

Oltersdorf et al., "An inhibitor of Bcl-2 family proteins induces regression of solid tumours," Nature, 435(7042):677-681 (2005).

Trudel et al., "Preclinical studies of the pan-Bcl inhibitor obatoclax (GX015-070) in multiple myeloma," Blood, 109(12):5430-5438 (2007).

Vandenberg et al., "ABT-199, a new Bcl-2-specific BH3 mimetic, has in vivo efficacy against aggressive Myc-driven mouse lymphomas without provoking thrombocytopenia," Blood, 121(12):2285-2288 (2013).

\* cited by examiner

TREATMENT OF CONDITIONS ASSOCIATED WITH HYPERINSULINAEMIA

RELATED APPLICATION(S)

This application is the U.S. National Stage of International Application No. PCT/US2015/018118, filed on Feb. 27, 2015, which designates the U.S., published in English, and claims the benefit of U.S. Provisional Application No. 61/946,682, filed on Feb. 28, 2014, 62/019,777, filed on Jul. 1, 2014 and 62/054,620, filed on Sep. 24, 2014. The entire teachings of the above applications are incorporated herein by reference.

BACKGROUND OF THE INVENTION

Hyperinsulinaemia is characterized by levels of insulin circulating in the blood that are in excess of those expected relative to the level of glucose. Hyperinsulinaemia is a result of unregulated insulin secretion by beta cells of the pancreas despite low blood glucose levels. Hyperinsulinaemia is associated with a variety of conditions such as insulinoma, congenital hyperinsulism, polycystic ovary syndrome (PCOS), Beckwith-Wiedemann syndrome and can occur in patients following gastric bypass surgery. As a result of hyperinsulinaemia, patients suffer from uncontrollable hypoglycemia which causes serious symptoms including headache, dizziness, lethargy, diplopia, blurred vision, unconsciousness, and in cases of severe hypoglycemia seizures, coma and permanent neurological damage.

For example, insulinomas are rare pancreatic tumors derived from the insulin producing beta cells of the pancreas. Unlike beta cells that secrete insulin in response to increases in blood glucose, the secretion of insulin by insulinomas is not properly regulated by glucose and the insulinomas continue to secrete insulin causing glucose levels to fall below normal levels. As a result, patients suffer from uncontrollable hypoglycemia causing the above listed symptoms.

Presently, the most effective treatment option for insulinomas involves surgery or medications, such as diazoxide and somatostatin, which can be utilized to lower insulin levels in patients. Available treatments for other conditions associated with hyperinsulinaemia are similarly limited. As such, effective therapies are limited.

SUMMARY OF THE INVENTION

As described below, the present invention features methods for treating a condition associated with hyperinsulinaemia.

A first embodiment of the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by Structural Formula I:

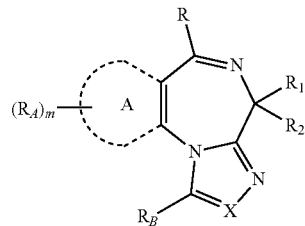

or a pharmaceutically acceptable salt thereof, wherein:

X is N or $CR_3$;

$R_3$ is selected from the group consisting of: H, —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl is optionally and independently substituted with 1 to 4 substituents;

$R_B$ is H, —($C_1$-$C_4$)alkyl, —($C_1$-$C_4$)alkylene-O—($C_1$-$C_4$)alkyl, or —COO—$R_4$, wherein each —($C_1$-$C_4$)alkyl and —($C_1$-$C_4$)alkylene-O—($C_1$-$C_4$)alkyl is optionally substituted with 1 to 4 substituents independently selected from the group consisting of —F, —Cl, —Br, —OH, and —$NR_5R_6$;

ring A is —($C_6$-$C_{10}$)aryl or —($C_5$-$C_{10}$)heteroaryl;

each $R_A$ is independently H, —($C_1$-$C_4$)alkyl, —($C_3$-$C_8$)cycloalkyl, —($C_5$-$C_7$) heterocycloalkyl, —($C_6$-$C_{10}$)aryl, or —($C_5$-$C_{10}$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl is optionally and independently substituted with 1 to 4 substituents; or any two $R_A$ together with the atoms to which each is bound form a fused aryl or heteroaryl group;

R is —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_{10}$)heteroaryl, wherein each is optionally and independently substituted with 1 to 4 substituents;

$R_1$ is —$(CH_2)_n$-L, in which n is 0-3 and L is H, —C(O)O—$R_9$, —CO—$N(R_9R_{10})$, —$NR_9R_{10}$, —$N(R_{10})C(O)OR_9$, or —$N(R_{10})C(O)R_9$;

$R_2$ is H, D, halogen, or —($C_1$-$C_4$)alkyl;

$R_4$, $R_5$, and $R_6$ are each independently selected from the group consisting of: H, —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl is optionally and independently substituted with 1 to 4 substituents;

$R_9$ is selected from the group consisting of: H, —($C_1$-$C_6$)alkyl, —($C_0$-$C_6$)alkylene-cycloalkyl, —($C_0$-$C_6$)alkylene-heterocycloalkyl, —($C_0$-$C_6$)alkylene-aryl, —($C_0$-$C_6$)alkylene-heteroaryl, and —N=$CR_{11}R_{12}$, wherein each —($C_1$-$C_6$)alkyl and —($C_0$-$C_6$)alkylene- is optionally and independently substituted with 1 to 4 substituents and each -cycloalkyl, -heterocycloalkyl, -aryl, and -heteroaryl is optionally and independently substituted with 1 to 4 substituents;

$R_{10}$ is selected from the group consisting of: H, —($C_1$-$C_6$)alkyl, —($C_0$-$C_6$)alkylene-cycloalkyl, —($C_0$-$C_6$)alkylene-heterocycloalkyl, —($C_0$-$C_6$)alkylene-aryl; and —($C_0$-$C_6$)alkylene-heteroaryl, wherein each —($C_1$-$C_6$)alkyl and —($C_0$-$C_6$)alkylene- is optionally and independently substituted with 1 to 4 substituents and each -cycloalkyl, -heterocycloalkyl, -aryl, and -heteroaryl is optionally and independently substituted with 1 to 4 substituents;

$R_9$ and $R_{10}$ are taken together with the nitrogen atom to which they are bound form a 4-10-membered ring;

$R_{11}$ is H, —$(C_1$-$C_4)$alkyl, or —$(C_1$-$C_4)$alkylene-O—$(C_1$-$C_4)$alkyl, wherein each —$(C_1$-$C_4)$alkyl, and —$(C_1$-$C_4)$alkylene-O—$(C_1$-$C_4)$alkyl is optionally and independently substituted with 1 to 3 substituents selected from the group consisting of: —F, —Cl, —Br, and —OH;

$R_{12}$ is H, —$(C_1$-$C_4)$alkyl, —$(C_3$-$C_8)$cycloalkyl, —$(C_5$-$C_7)$heterocycloalkyl, —$(C_6$-$C_{10})$aryl, or —$(C_5$-$C_7)$heteroaryl, wherein each —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heieroaryl is optionally and independently substituted with 1 to 4 substituents; and m is 0, 1, 2, or 3.

In a particular embodiment, the condition associated with hyperinsulinaemia is an insulinoma.

In another embodiment, the condition associated with hyperinsulinaemia is congenital hyperinsulism.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Definitions

Figure 1:
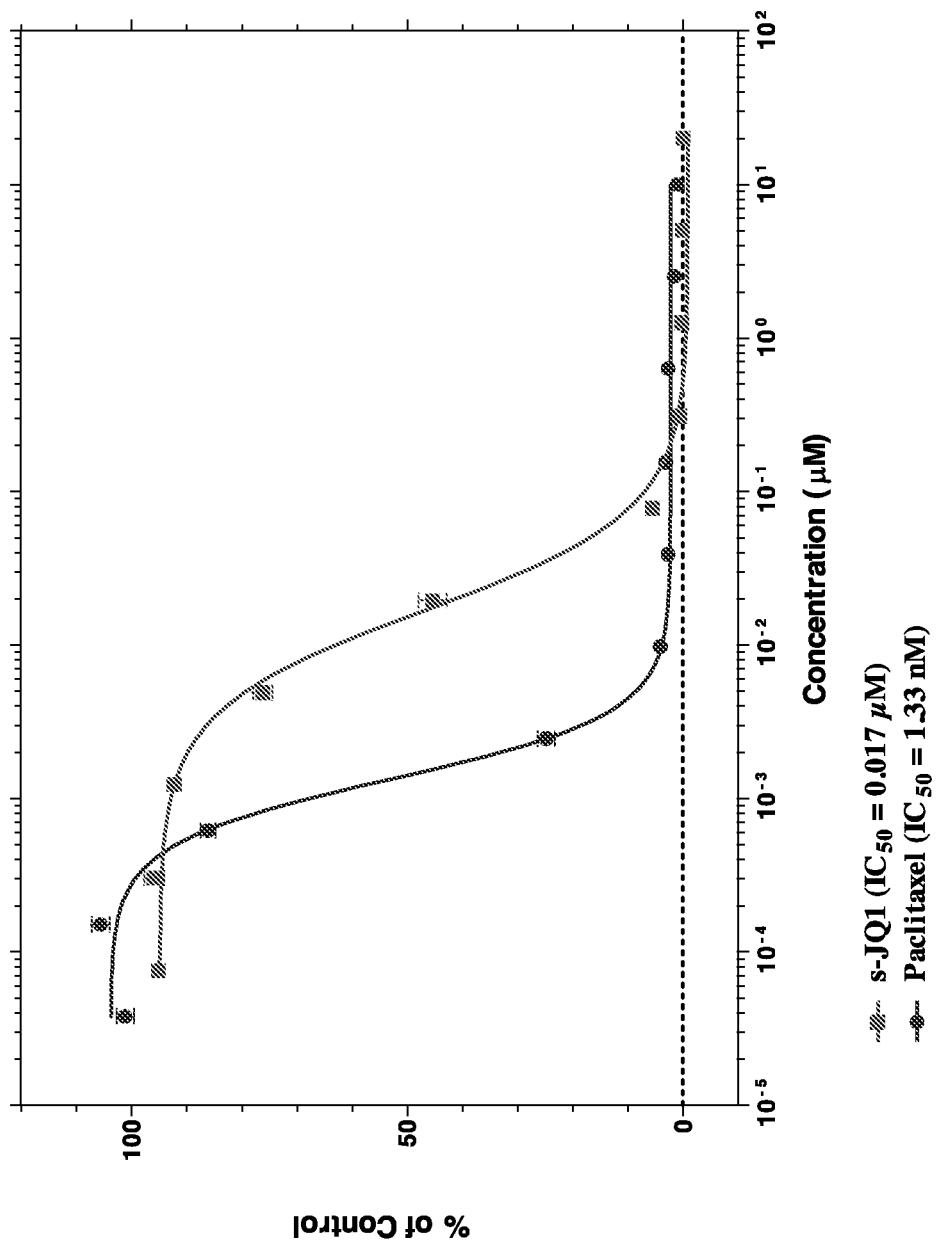
FIG. 1 is a graph showing cell viability of the rat insulinoma cell line, RIN-14B, when treated with varying concentrations of (S)-JQ1 or Paclitaxel.
Figure 2:
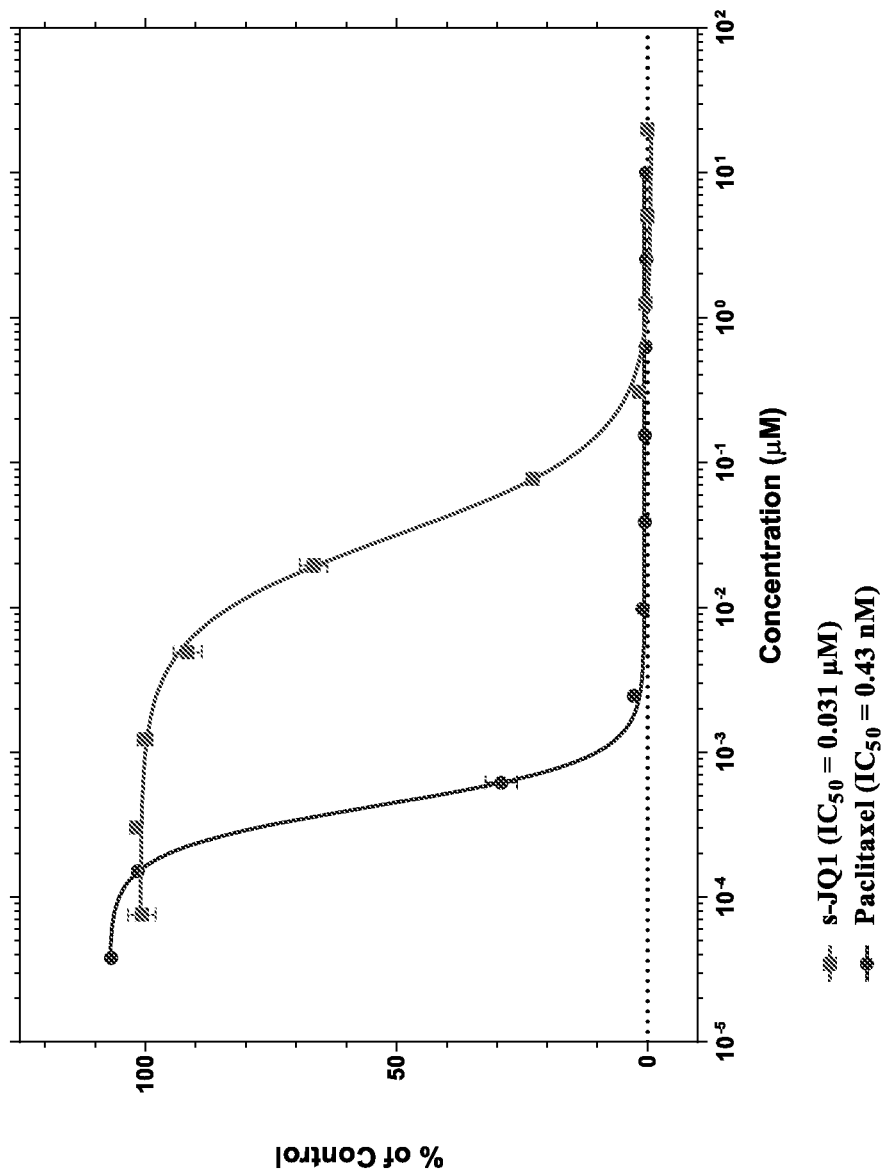
FIG. 2 is a graph showing cell viability of the rat insulinoma cell line, RIN-m5F, when treated with varying concentrations of (S)-JQ1 or Paclitaxel.
Figure 3:
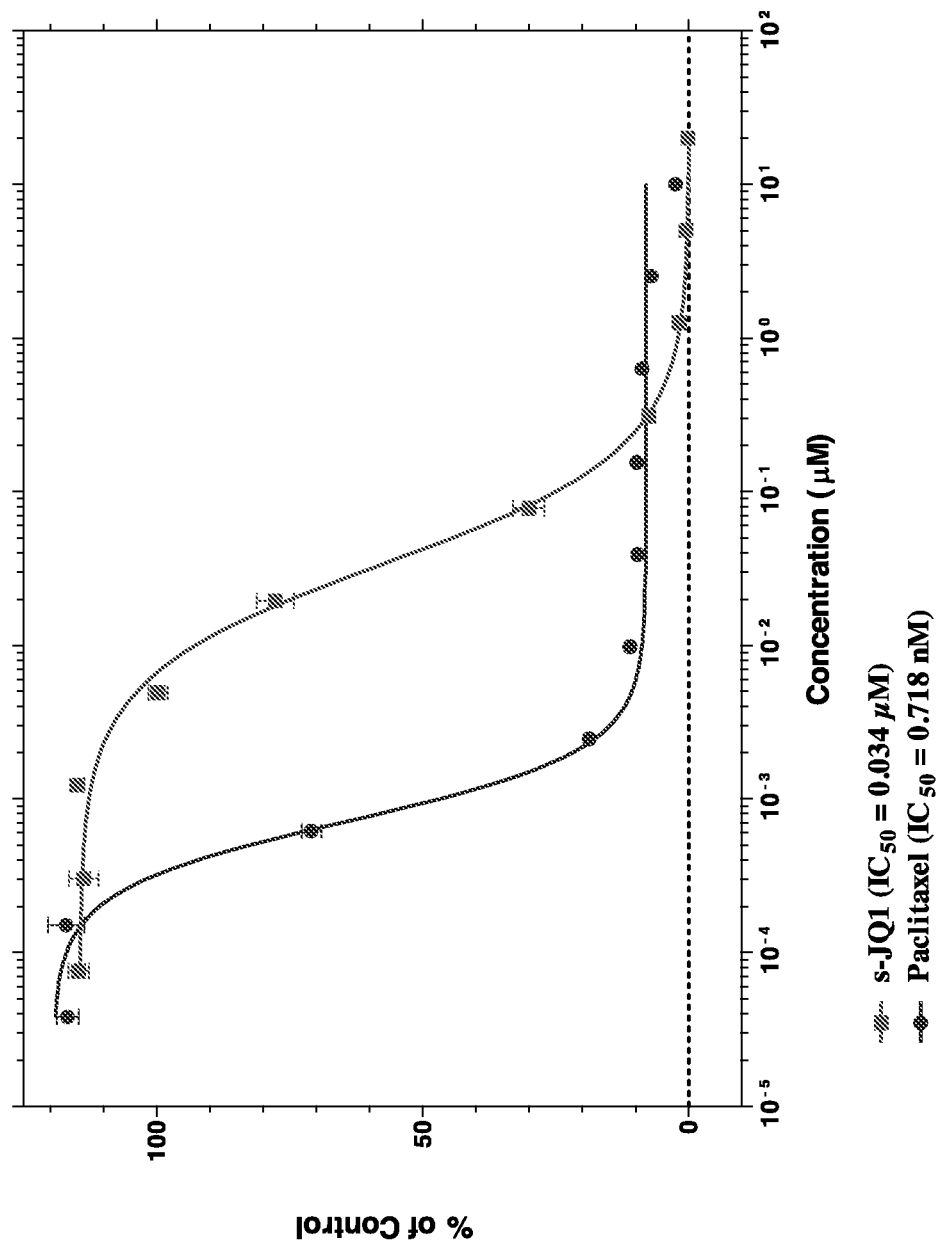
FIG. 3 is a graph showing cell viability of the rat insulinoma cell line, RIN-m, when treated with varying concentrations of (S)-JQ1 or Paclitaxel.
Figure 4:
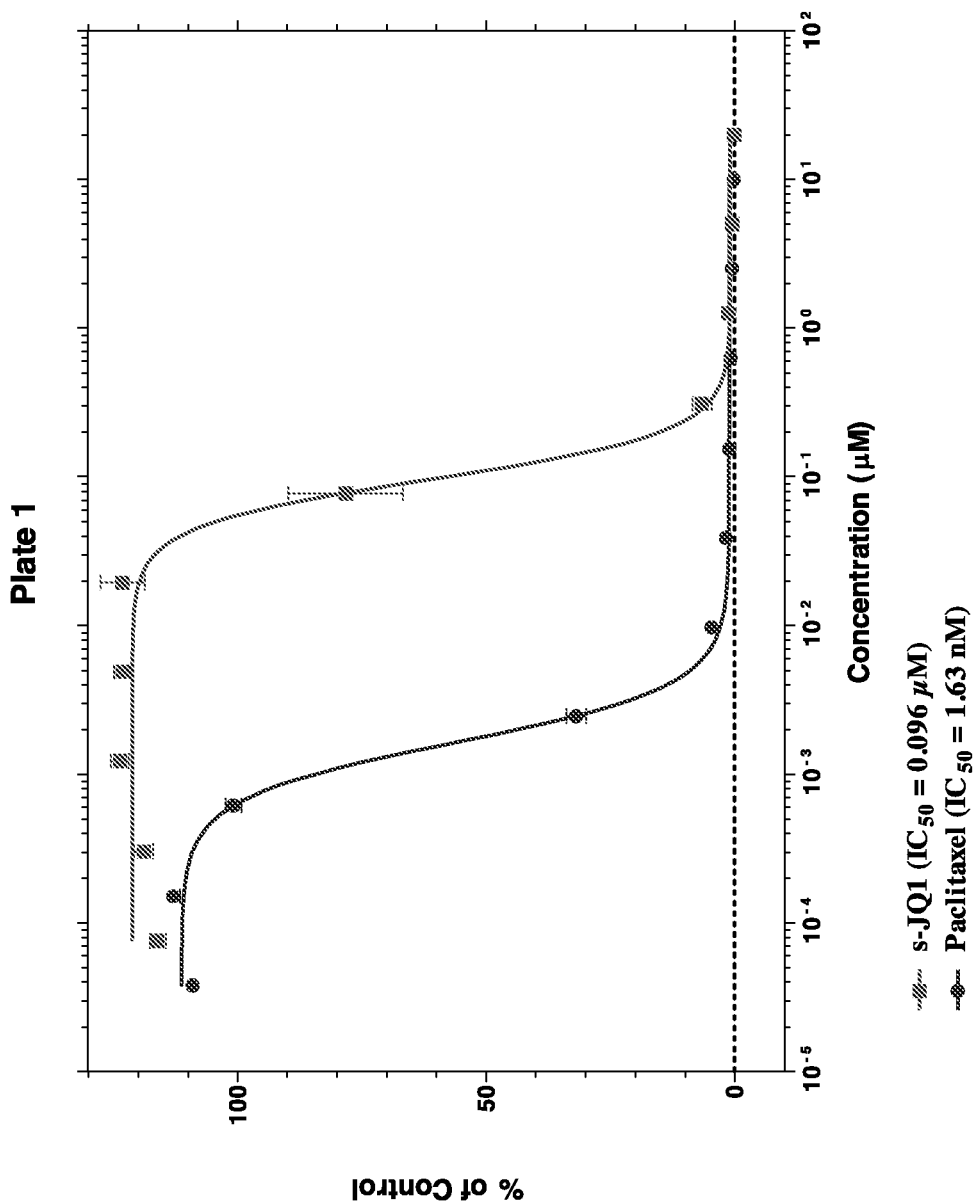
FIG. 4 is a graph showing cell viability of the rat insulinoma cell line, RIN-5F, when treated with varying concentrations of (S)-JQ1 or Paclitaxel.
Figure 5:
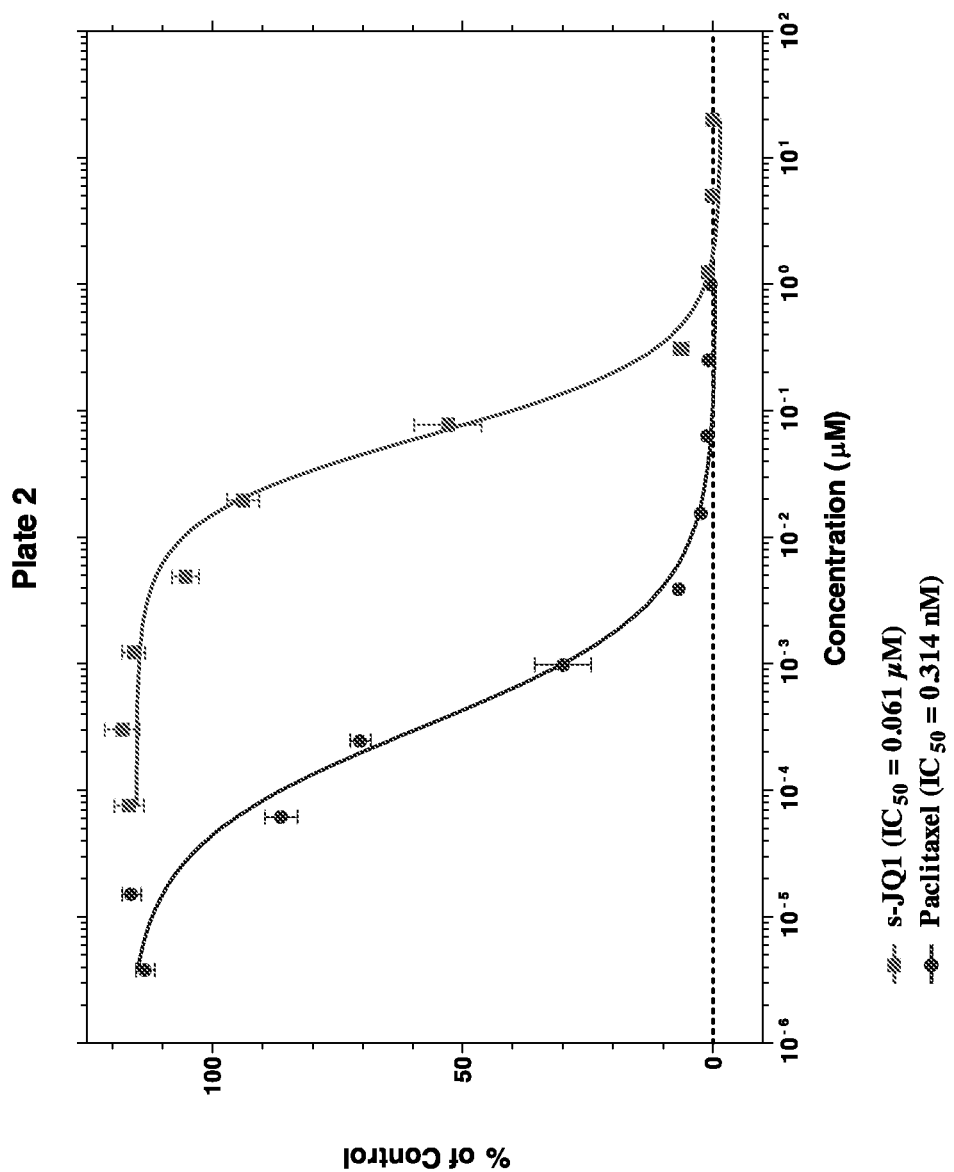
FIG. 5 is a graph showing cell viability of the rat insulinoma cell line, RIN-5F, when treated with varying concentrations of (S)-JQ1 or Paclitaxel.

"Alkyl" means an optionally substituted saturated aliphatic branched or straight-chain monovalent hydrocarbon radical having the specified number of carbon atoms. Thus, "$(C_1$-$C_6)$ alkyl" means a radical having from 1-6 carbon atoms in a linear or branched arrangement. "$(C_1$-$C_6)$alkyl" includes methyl, ethyl, propyl, iso-propyl (or i-propyl), butyl, sec-butyl, tert-butyl, pentyl, hexyl and the like.

"Alkylene" means an optionally substituted saturated aliphatic branched or straight-chain divalent hydrocarbon radical having the specified number of carbon atoms. Thus, "$(C_1$-$C_6)$alkylene" means a divalent saturated aliphatic radical having from 1-6 carbon atoms in a linear arrangement, e.g., —$[(CH_2)_n]$—, where n is an integer from 1 to 6, "$(C_1$-$C_6)$alkylene" includes methylene, ethylene, propylene, butylene, pentylene and hexylene. Alternatively, "$(C_1$-$C_6)$ alkylene" means a divalent saturated radical having from 1-6 carbon atoms in a branched arrangement, for example: —$[(CH_2CH_2CH_2CH_2CH(CH_3)]$—, —$[(CH_2CH_2CH_2CH_2C(CH_3)_2]$—, —$[(CH_2C(CH_3)_2CH(CH_3))]$—, and the like. A specific branched $C_3$-alkylene is

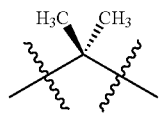

and a specific $C_4$-alkylene is

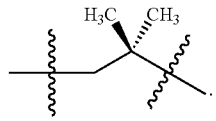

Each alkyl or alkylene in Structural Formulas (I-IX) can be optionally and independently substituted with one or more substituents.

"Aryl" or "aromatic" means an aromatic monocyclic or polycyclic (e.g. bicyclic or tricyclic) carbon-containing ring system. In one embodiment, "aryl" is a 6-12 membered monocyclic or bicyclic system. Aryl systems include, but are not limited to, phenyl, naphthalenyl, fluorenyl, indenyl, azulenyl, and anthracenyl.

"Cycloalkyl" means a saturated aliphatic cyclic hydrocarbon ring. "Cycloalkyl" includes 3- to 12-membered saturated aliphatic cyclic hydrocarbon rings. Thus, "$(C_3-C_7)$cycloalkyl" means a hydrocarbon radical of a 3- to 7-membered saturated aliphatic cyclic hydrocarbon ring. A $(C_3-C_7)$cycloalkyl includes, but is not limited to cyclopropyl, cyclobutyl, cyclopentyl, cyclohexyl and cycloheptyl.

A cycloalkyl moiety can be monocyclic, fused bicyclic, bridged bicyclic, spiro bicyclic, or polycyclic. For example, monocyclic $(C_3-C_8)$cycloalkyl means a radical having from 3 to 8 carbon atoms arranged in a monocyclic ring. Monocyclic $(C_3-C_8)$cycloalkyl includes, but is not limited to, cyclopropyl, cyclobutyl, cyclopentyl, cyclohexyl, cycloheptyl and cyclooctane.

Monocyclic ring systems have a single ring structure. They include saturated or unsaturated aliphatic cyclic hydrocarbon rings (e.g., cycloalkyl, cycloalkenyl, or cycloalkynyl) or aromatic hydrocarbon rings (e.g., aryl) having the specified number of carbon atoms. The monocyclic ring system can optionally contain 1 to 5 heteroatoms in the ring structure wherein each heteroatom is independently selected from the group consisting O, N and S (e.g., heterocycloalkyl, heterocycloalkenyl, heterocycloalkynyl or heteroaryl). When the heteroatom is N, it can be optionally substituted with alkyl, cycloalkyl, alkylene-cycloalkyl, heterocycloalkyl, alkylene-heterocycloalkyl, aryl, alkylene-aryl, heteroaryl, alkylene-heteroaryl, each of which can be optionally substituted with one or more halogen, =O, hydroxy, alkoxy, haloalkyl, alkyl, etc. When the heteroatom is S, it can be optionally mono- or di-oxygenated (i.e., —S(O)— or —S(O)$_2$—). Examples of monocyclic ring systems include, but are not limited to, cyclopropyl, cyclobutyl, cyclopentyl, cyclohexyl, cycloheptyl, cyclooctane, azetidine, pyrrolidine, piperidine, piperazine, azepane hexahydropyrimidine, tetrahydrofuran, tetrahydropyran, oxepane, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine, tetrahydro-2H-1,2-thiazine 1,1-dioxide, and isothiazolidine 1,1-dioxide, tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one.

Bicyclic ring systems have two rings that have at least one ring atom in common. Bicyclic ring systems include fused, bridged and spiro ring systems. The two rings can both be aliphatic (e.g., cycloalkyl, cycloalkene, cycloalkyne, or heterocycloalkyl), both be aromatic (e.g., aryl or heteroaryl), or a combination thereof. The bicyclic ring systems can optionally contain 1 to 5 heteroatoms in the ring structure wherein each heteroatom is independently selected from the group consisting O, N and S. When the heteroatom is N, it can be substituted with H, alkyl, cycloalkyl, alkylene-cycloalkyl, heterocycloalkyl, alkylene-heterocycloalkyl, aryl, alkylene-aryl, heteroaryl, alkylene-heteroaryl, each of which can be optionally substituted with one or more halogen, =O, hydroxy, alkoxy, haloalkyl, alkyl, etc. When the heteroatom is S, it can be optionally mono- or di-oxygenated (i.e. —S(O)— or —S(O)$_2$—).

A fused bicyclic ring system has two rings which have two adjacent ring atoms in common. The two rings can both be aliphatic (e.g., cycloalkyl, cycloalkene, cycloalkyne, or heterocycloalkyl), both be aromatic (e.g., aryl or heteroaryl), or a combination thereof. For example, the first ring can be cycloalkyl or heterocycloalkyl, and the second ring can be a cycloalkyl, cycloalkene, cycloalkyne, aryl, heteroaryl or a heterocycloalkyl. For example, the second ring can be a $(C_3-C_6)$cycloalkyl, such as cyclopropyl, cyclobutyl, cyclopentyl and cyclohexyl. Alternatively, the second ring can be an aryl ring (e.g., phenyl). Examples of fused bicyclic ring systems include, but are not limited to, 6,7,8,9-tetrahydro-5H-benzo[7]annulene, 2,3-dihydro-1H-indene, octahydro-1H-indene, tetrahydronaphthalene, decahydronaphthalene, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, 3-azabicyclo[3.2.0]heptane, 5,6,7,8-tetrahydroquinoline and 5,6,7,8-tetrahydroisoquinoline, and 2,3,4,5-tetrahydrobenzo[b]oxepine.

A spiro bicyclic ring system has two rings which have only one ring atom in common. The two rings can both be aliphatic (e.g., cycloalkyl, cycloalkene, cycloalkyne, or heterocycloalkyl), both be aromatic (e.g., aryl or heteroaryl), or a combination thereof. For example, the first ring can be a cycloalkyl or a heterocycloalkyl and the second ring can be a cycloalkyl, a cycloalkene, a cycloalkyne, an aryl, a heteroaryl, or a heterocycloalkyl. Examples of spiral bicyclic ring systems include, but are not limited to, spiro[2.2]pentane, spiro[2.3]hexane, spiro[3.3]heptane, spiro[2.4]heptane, spiro[3.4]octane, spiro[2.5]octane, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane, and 3,9-diazaspiro[5.5]undecane.

A bridged bicyclic ring system has two rings which have three or more adjacent ring atoms in common. The two rings can both be aliphatic (e.g., cycloalkyl, cycloalkene, cycloalkyne, or heterocycloalkyl), both be aromatic (e.g., aryl or heteroaryl), or a combination thereof. For example, the first ring can be a cycloalkyl or a heterocycloalkyl and the other ring is a cycloalkyl, a cycloalkene, a cycloalkyne, an aryl, a heteroaryl or a heterocycloalkyl. Examples of bridged bicyclic ring systems include, but are not limited to, bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane bicyclo[3.3.3]undecane, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane, and 2-oxabicyclo[2.2.2]octane.

Polycyclic ring systems have more than two rings (e.g., three rings resulting in a tricyclic ring system) and adjacent rings have at least one ring atom in common. Polycyclic ring systems include fused, bridged and Spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common. Examples of polycyclic ring systems include, but are not limited to, tricyclo[3.3.1.0$^{3,7}$]nonane (noradamantane), tricyclo[3.3.1.1$^{3,7}$]decane (adamantane) and 2,3-dihydro-1H-phenalene.

"Cycloalkene" means an aliphatic cyclic hydrocarbon ring having one or more double bonds in the ring. "Cycloalkene" includes 3- to 12-membered unsaturated aliphatic cyclic hydrocarbon rings. Thus, "$(C_3-C_7)$cycloalkene" means a hydrocarbon radical of a 3- to 7-membered unsaturated aliphatic cyclic hydrocarbon ring. A $(C_3-C_7)$ cycloalkene includes, but is not limited to cyclopropenyl, cyclobutenyl, cyclopentenyl, cyclohexenyl and cycloheptenyl.

A cycloalkene moiety can be monocyclic, fused bicyclic, bridged bicyclic, spiro bicyclic, or polycyclic. For example, monocyclic $(C_3-C_8)$cycloalkene means a radical having from 3 to 8 carbon atoms arranged in a monocyclic ring. Monocyclic $(C_3-C_8)$cycloalkene includes, but is not limited to, cyclopropenyl, cyclobutenyl, cyclopentenyl, cyclohexenyl and cycloheptenyl.

"Cycloalkyne" means an aliphatic cyclic hydrocarbon ring having one or more triple bonds in the ring. "Cycloalkyne" includes 3- to 12-membered unsaturated aliphatic cyclic hydrocarbon rings. Thus, "$(C_3-C_7)$cycloalkyne" means a hydrocarbon radical of a 3- to 7-membered unsaturated aliphatic cyclic hydrocarbon ring. A $(C_3-C_7)$ cycloalkyne includes, but is not limited to cyclopropynyl, cyclobutynyl, cyclopentynyl, cyclohexynyl and cycloheptynyl.

A cycloalkyne moiety can be monocyclic, fused bicyclic, bridged bicyclic, spiro bicyclic, or polycyclic. For example, monocyclic $(C_3-C_8)$cycloalkyne means a radical having from 3 to 8 carbon atoms arranged in a monocyclic ring. Monocyclic $(C_3-C_8)$cycloalkyne includes, but is not limited to, cyclopropynyl, cyclobutynyl, cyclopentynyl, cyclohexynyl, and cycloheptynyl.

"Hetero" refers to the replacement of at least one carbon atom member in a ring system with at least one heteroatom selected from N, S, and O. "Hetero" also refers to the replacement of at least one carbon atom member in an acyclic system. A hetero ring system or a hetero acyclic system may have 1, 2, 3, 4 or 5 carbon atoms members replaced by a heteroatom.

"Heterocycloalkyl" means a cyclic 4- to 12-membered saturated aliphatic ring containing 1, 2, 3, 4 or 5 heteroatoms independently selected from N, O or S. When one heteroatom is S, it can be optionally mono- or di-oxygenated (i.e. —S(O)— or —S(O)$_2$—). When one heteroatom is N, it can be optionally substituted with alkyl, cycloalkyl, alkylene-cycloalkyl, heterocycloalkyl, alkylene-heterocycloalkyl, aryl, alkylene-aryl, heteroaryl, alkylene-heteroaryl, each of which can be optionally substituted with one or more halogen, =O, hydroxy, alkoxy, haloalkyl, alkyl, etc.

A heterocycloalkyl moiety can be monocyclic, fused bicyclic, bridged bicyclic, spiro bicyclic, or polycyclic. For example, monocyclic $(C_3-C_8)$ heterocycloalkyl means a 3- to 8 membered saturated aliphatic ring containing 1, 2, 3, 4, or 5 heteroatoms independently selected from N, O or S arranged in a monocyclic ring. Examples of monocyclic heterocycloalkyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

"Heteroaryl" or "heteroaromatic ring" means a 5- to 12-membered monovalent heteroaromatic monocyclic or bicyclic ring radical. A heteroaryl contains 1, 2, 3, 4, or 5 heteroatoms independently selected from N, O, and S. Heteroaryls include, but are not limited to furan, oxazole, thiophene, 1,2,3-triazole, 1,2,4-triazine, 1,2,4-triazole, 1,2,5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole. Bicyclic heteroaryl rings include, but are not limited to, bicyclo[4.4.0] and bicyclo[4.3.0] fused ring systems such as indolizine, indole, isoindole, indazole, benzimidazole, benzothiazole, purine, quinoline, isoquinoline, cinnoline, phthalazine, quinazoline, quinoxaline, benzofuran, 1,8-naphthyridine, and pteridine.

In a particular embodiment, each cycloalkyl, cycloalkene, cycloalkyne, cycloheterocycloalkyl, aryl and heteroaryl is optionally and independently substituted with 1 to 4. Exemplary substituents include, but are not limited to, halo, —$(C_1-C_4)$alkyl, —OH, =O, —O—$(C_1-C_4)$alkyl, —$(C_1-C_4)$alkylene-O—$(C_1-C_4)$alkyl, halo-substituted- $(C_1-C_4)$alkyl, halo-substituted-O—$(C_1-C_4)$alkyl, and —C(O)—$(C_1-C_4)$alkyl.

"Halogen," as used herein, refers to fluorine, chlorine, bromine, or iodine.

"Alkoxy" means an alkyl radical attached through an oxygen linking atom. "$(C_1-C_6)$alkoxy" includes methoxy, ethoxy, propoxy, butoxy, pentoxy and hexoxy.

Haloalkyl and halocycloalkyl include mono, poly, and perhalo-substituted alkyl or cycloalkyl groups where each halogen is independently selected from fluorine, chlorine, and bromine.

"Halogen" and "halo" are interchangeably used herein and each refers to fluorine, chlorine, bromine, or iodine.

"Fluoro" means —F.

As used herein, fluoro-substituted $(C_1-C_4)$alkyl means a $(C_1-C_4)$alkyl substituted with one or more —F groups. Examples of fluoro-substituted-$(C_1-C_4)$alkyl include, but are not limited to, —CF$_3$, —CH$_2$CF$_3$, —CH$_2$CF$_2$H, —CH$_2$CH$_2$F and —CH$_2$CH$_2$CF$_3$.

"Naturally occurring amino acid side chain moiety" refers to any amino acid side chain moiety present in a natural amino acid.

Values and Alternative Values for Variables

The present invention is directed to method of treating a condition associated with hyperinsulinaemia (e.g., insulinoma, congenital insulism, polycystic ovary syndrome (PCOS), Beckwith-Wiedemann syndrome and in patients following gastric bypass surgery) in a subject in need thereof, comprising administering to the subject an effective amount of a compound represented by Formulas (I-IX) or a pharmaceutically acceptable salt thereof. In a particular embodiment, the condition associated with hyperinsulinaemia is an insulinoma. In a specific embodiment, the condition associated with hyperinsulinaemia is congenital hyperinsulinism.

Values and alternative values for the variables in Formulas (I-IX) or an enantiomer, a diastereomer, a tautomer, or a pharmaceutically acceptable salt thereof and for each of the embodiments described herein are provided in the following paragraphs. It is understood that the invention encompasses all combinations of the substituent variables (i.e., $R_1$, $R_2$, $R_3$, etc.) defined herein.

X is N or CR$_3$;

$R_3$ is selected from the group consisting of: H, —$(C_1-C_4)$ alkyl, —$(C_3-C_8)$cycloalkyl, —$(C_5-C_7)$heterocycloalkyl, —$(C_6-C_{10})$aryl, and —$(C_5-C_{10})$heteroaryl, wherein each —$(C_1-C_4)$alkyl, —$(C_3-C_8)$cycloalkyl, —$(C_5-C_7)$heterocycloalkyl, —$(C_6-C_{10})$aryl, and —$(C_5-C_{10})$heteroaryl is optionally substituted with 1 to 4 substituents independently selected from —F, —Cl, —Br, —OH, =O, —S(O)—, —S(O)$_2$—, —$(C_1-C_4)$alkyl, —O—$(C_1-C_4)$alkyl, —$(C_1-C_4)$ alkylene-O—$(C_1-C_4)$alkyl, halo-substituted-$(C_1-C_4)$alkyl, halo-substituted-O—($C_1$-$C_4$)alkyl, —C(O)—($C_1$-$C_4$)alkyl, and —C(O)-(fluoro-substituted-($C_1$-$C_4$)alkyl).

Alternatively, $R_3$ is selected from the group consisting of: H and —($C_1$-$C_4$)alkyl. Further, $R_3$ is selected from the group consisting of: H, methyl, ethyl, propyl, butyl, sec-butyl and tert-butyl. Specifically, $R_3$ is H or methyl.

$R_B$ is H, —($C_1$-$C_4$)alkyl, —($C_1$-$C_4$)alkylene-O—($C_1$-$C_4$)alkyl, or —COO—$R_4$, wherein each —($C_1$-$C_4$)alkyl and —($C_1$-$C_4$)alkylene-O—($C_1$-$C_4$)alkyl is optionally substituted with 1 to 4 substituents independently selected from the group consisting of —F, —Cl, —Br, —OH, and —$NR_5R_6$;

Alternatively, $R_B$ is H, —($C_1$-$C_4$)alkyl, or —($C_1$-$C_4$)alkylene-O—($C_1$-$C_4$)alkyl, wherein each is optionally substituted with 1 to 4 substituents independently selected from the group consisting of —F, —Cl, —Br, —OH, and —$NR_5R_6$.

Further, $R_B$ is H, methyl, ethyl, propyl, butyl, sec-butyl, tert-butyl, —COOH, —COOMe, —COOEt, —COOCH$_2$OC(O)CH$_3$, trifluoromethyl, —CF$_2$—CF$_3$, methoxymethyl, methoxyethyl, methoxypropyl, ethoxymethyl, ethoxyethyl, methoxytrifluoromethyl, —CH$_2$—O—CF$_2$—CF$_3$, hydroxymethyl, hydroxyethyl, —CH$_2$—NH$_2$, —(CH$_2$)$_2$—NH$_2$, —CH$_2$—NHCH$_3$, or —(CH$_2$)$_2$—NHCH$_3$. In another alternative, $R_B$ is H, methyl, ethyl, trifluoromethyl, methoxymethyl, ethoxymethyl, hydroxymethyl, hydroxyethyl, —CH$_2$—NH$_2$, or —(CH$_2$)$_2$—NH$_2$.

Specifically, $R_B$ is H, methyl, ethyl, trifluoromethyl, methoxymethyl, ethoxymethyl, hydroxymethyl, or —CH$_2$—NH$_2$. Alternatively, $R_B$ is H.

Ring A is —($C_6$-$C_{10}$)aryl or —($C_5$-$C_{10}$)heteroaryl. Alternatively, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

Alternatively, ring A is 5- or 6-membered aryl or heteroaryl. Ring A is thiofuranyl, phenyl, pyridyl, furanyl, indolyl, pyrimidinyl, pyridizinyl, pyrazinyl, imidazolyl, oxazolyl, thienyl, thiazolyl, triazolyl, isoxazolyl, pyrrolyl, or pyrazolyl. Further, ring A is phenyl or thienyl. Specifically, ring A is thienyl.

Each $R_A$ is independently H, —($C_1$-$C_4$)alkyl, —($C_3$-$C_8$)cycloalkyl, —($C_5$-$C_7$) heterocycloalkyl, —($C_6$-$C_{10}$)aryl, or —($C_5$-$C_{10}$)heteroaryl, wherein each —($C_1$-$C_4$)alkyl, —($C_3$-$C_8$)cycloalkyl, —($C_5$-$C_7$) heterocycloalkyl, —($C_6$-$C_{10}$)aryl, and —($C_5$-$C_{10}$)heteroaryl is optionally substituted with 1 to 4 substituents independently selected from —F, —Cl, —Br, —OH, =O, —S(O)—, —S(O)$_2$—, —($C_1$-$C_4$)alkyl, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, and —C(O)-(fluoro-substituted-($C_1$-$C_4$)alkyl); or any two $R_A$ together with the atoms to which each is bound form a fused aryl or heteroaryl group.

Alternatively, each $R_A$ is independently H or —($C_1$-$C_4$) alkyl. Each $R_A$ is independently H, methyl, ethyl, propyl, butyl, sec-butyl, or tert-butyl. Specifically, each $R_A$ is independently H or methyl.

Alternatively, any two $R_A$ together with the atoms to which each is bound form a fused aryl or heteroaryl group. Further, any two $R_A$ together with the atoms to which each is bound form a fused aryl.

R is —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_{10}$)heteroaryl, wherein each is optionally substituted with 1 to 4 substituents independently selected from the group consisting of: —F, —Cl, —Br, —OH, —($C_1$-$C_4$)alkyl, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_2$-$C_4$)alkyl, —C(O)—($C_1$-$C_4$)alkyl, —C(O)-(fluoro-substituted-($C_1$-$C_4$)alkyl), —S(O)$_o$—($C_1$-$C_4$)alkyl, —$NR_7R_8$ and CN.

Alternatively, R is —($C_6$-$C_{10}$)aryl, or —($C_5$-$C_{10}$)heteroaryl, wherein each is optionally substituted with 1 to 4 substituents independently selected from the group consisting of: —F, —Cl, —Br, —OH, —($C_1$-$C_4$)alkyl, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, —C(O)-(fluoro-substituted-($C_1$-$C_4$)alkyl), —S(O)$_o$—($C_1$-$C_4$)alkyl, —$NR_7R_8$ and CN.

R is phenyl or pyridinyl, wherein each is optionally substituted with 1 to 4 substituents independently selected from the group consisting of: —F, —Cl, —Br, —OH, —($C_1$-$C_4$)alkyl, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, —C(O)-(fluoro-substituted-($C_1$-$C_4$)alkyl), —S(O)$_o$—($C_1$-$C_4$)alkyl, —$NR_7R_8$ and CN.

Further, R is phenyl or pyridinyl wherein each is optionally substituted with 1 to 4 substituents independently selected from the group consisting of: —F, —Cl, —Br, —OH, -methyl, ethyl, propyl, butyl, sec-butyl, tert-butyl, —COOH, —COOMe, —COOEt, —COOCH$_2$OC(O)CH$_3$, trifluoromethyl, —CF$_2$—CF$_3$, methoxymethyl, methoxyethyl, methoxypropyl, ethoxymethyl, ethoxyethyl, methoxytrifluoromethyl, —CH$_2$—O—CF$_2$—CF$_3$, hydroxymethyl, hydroxyethyl, —CH$_2$—NH$_2$, —(CH$_2$)$_2$—NH$_2$, —CH$_2$—NHCH$_3$, —(CH$_2$)$_2$—NHCH$_3$ and CN. Alternatively, R is phenyl or pyridinyl wherein each is optionally substituted with 1 to 4 substituents independently selected from the group consisting of: —F, —Cl, —Br, -and OH.

R is phenyl optionally substituted with 1 to 4 substituents independently selected from the group consisting of: —F, —Cl, —Br, -and OH. Alternatively, R is phenyl optionally substituted with 1 to 3 substituents independently selected from the group consisting of: —F, —Cl, —Br, -and OH. Further, R is phenyl optionally substituted with a substituent independently selected from the group consisting of: —F, —Cl, —Br, -and OH. Specifically, R is p-Cl-phenyl, o-Cl-phenyl, m-Cl-phenyl, p-F-phenyl, o-F-phenyl, m-F-phenyl or pyridinyl.

$R_1$ is —(CH$_2$)$_n$-L, in which n is 0-3 and L is H, —C(O)O—$R_9$, —CO—N($R_9R_{10}$), —$NR_9R_{10}$, —N($R_{10}$)C(O)O$R_9$, or —N($R_{10}$)C(O)$R_9$.

Alternatively, $R_1$ is —(CH$_2$)$_n$-L, in which n is 0-3, and L is —C(O)O—$R_9$. $R_1$ is —(CH$_2$)$_n$-L, in which n is 1-3, and L is —C(O)O—$R_9$. Further, $R_1$ is —(CH$_2$)$_n$-L, in which n is 1-2, and L is —C(O)O—$R_9$. Alternatively, $R_1$ is —(CH$_2$)$_n$-L, in which n is 1, and L is —C(O)O—$R_9$.

Further, $R_1$ is —(CH$_2$)$_n$-L, in which n is 0-3, and L is —CO—N($R_9R_{10}$). $R_1$ is —(CH$_2$)$_n$-L, in which n is 1-3, and L is —CO—N($R_9R_{10}$). $R_1$ is —(CH$_2$)$_n$-L, in which n is 1-2, and L is —CO—N($R_9R_{10}$). Alternatively, $R_1$ is —(CH$_2$)$_n$-L, in which n is 1, and L is —CO—N($R_9R_{10}$).

In another alternative, $R_1$ is —(CH$_2$)$_n$-L, in which n is 0-3, and L is —$NR_9R_{10}$. $R_1$ is —(CH$_2$)$_n$-L, in which n is 1-3, and L is —$NR_9R_{10}$. Further, $R_1$ is —(CH$_2$)$_n$-L, in which n is 1-2, and L is —$NR_9R_{10}$. Alternatively, $R_1$ is —(CH$_2$)$_n$-L, in which n is 1, and L is —$NR_9R_{10}$.

$R_1$ is —(CH$_2$)$_n$-L, in which n is 0-3, and L is —N($R_{10}$)C(O)O$R_9$. Alternatively, $R_1$ is —(CH$_2$)$_n$-L, in which n is 1-3, and L is —N($R_{10}$)C(O)O$R_9$. Further, $R_1$ is —(CH$_2$)$_n$-L, in which n is 1-2, and L is —N($R_{10}$)C(O)O$R_9$. Alternatively, $R_1$ is —(CH$_2$)$_n$-L, in which n is 1, and L is —N($R_{10}$)C(O)O$R_9$.

Further, $R_1$ is —(CH$_2$)$_n$-L, in which n is 0-3, and L is —N($R_{10}$)C(O)$R_9$. Alternatively, $R_1$ is —(CH$_2$)$_n$-L, in which n is 1-3, and L is —N($R_{10}$)C(O)$R_9$. Further, $R_1$ is —(CH$_2$)$_n$-L, in which n is 1-2, and L is —N($R_{10}$)C(O)$R_9$. Alternatively, $R_1$ is —(CH$_2$)$_n$-L, in which n is 1, and L is —N($R_{10}$)C(O)$R_9$.

Alternatively, $R_1$ is —(CH$_2$)$_n$-L, in which n is 0-3 and L is H. $R_1$ is methyl, ethyl, propyl, iso-propyl. Specifically, $R_1$ is methyl.

$R_2$ is H, D, halogen, or —(C$_1$-C$_4$)alkyl. Alternatively, $R_2$ is H or —(C$_1$-C$_4$)alkyl. Further, $R_2$ is H, methyl, ethyl, propyl, iso-propyl, butyl, sec-butyl or tert-butyl. Specifically, $R_2$ is H or methyl.

$R_4$ is selected from the group consisting of: H, —(C$_1$-C$_4$)alkyl, —(C$_3$-C$_8$)cycloalkyl, —(C$_5$-C$_7$)heterocycloalkyl, —(C$_6$-C$_{10}$)aryl, and —(C$_5$-C$_7$)heteroaryl, wherein each —(C$_1$-C$_4$)alkyl, —(C$_3$-C$_8$)cycloalkyl, —(C$_5$-C$_7$)heterocycloalkyl, —(C$_6$-C$_{10}$)aryl, and —(C$_5$-C$_7$)heteroaryl is optionally substituted with 1 to 4 substituents independently selected from the group consisting of: —F, —Cl, —Br, —OH, —(C$_1$-C$_4$)alkyl, —O—(C$_1$-C$_4$)alkyl, —(C$_1$-C$_4$)alkylene-O—(C$_1$-C$_4$)alkyl, halo-substituted-(C$_1$-C$_4$)alkyl, halo-substituted-O—(C$_1$-C$_4$)alkyl, —C(O)—(C$_1$-C$_4$)alkyl, and —C(O)-(fluoro-substituted-(C$_1$-C$_4$)alkyl).

Alternatively, $R_4$ is selected from the group consisting of: H and —(C$_1$-C$_4$)alkyl, wherein each —(C$_1$-C$_4$)alkyl is optionally substituted with 1 to 4 substituents independently selected from the group consisting of: —F, —Cl, —Br, —OH, —(C$_1$-C$_4$)alkyl, —O—(C$_1$-C$_4$)alkyl, —(C$_1$-C$_4$)alkylene-O—(C$_1$-C$_4$)alkyl, halo-substituted-(C$_1$-C$_4$)alkyl, halo-substituted-O—(C$_1$-C$_4$)alkyl, —C(O)—(C$_1$-C$_4$)alkyl, and —C(O)-(fluoro-substituted-(C$_1$-C$_4$)alkyl).

$R_4$ is selected from the group consisting of: H and —(C$_1$-C$_4$)alkyl, wherein each —(C$_1$-C$_4$)alkyl is optionally substituted with 1 to 4 substituents independently selected from the group consisting of: —F, —Cl, —Br, and —OH. In another alternative, $R_4$ is selected from the group consisting of: H, methyl, ethyl, propyl, iso-propyl, butyl, sec-butyl, tert-butyl, trifluoromethyl, —CF$_2$—CF$_3$, hydroxymethyl, and hydroxyethyl. Alternatively, $R_4$ is selected from the group consisting of: H, methyl, ethyl, tert-butyl, and trifluoromethyl.

$R_5$ is selected from the group consisting of: H, —(C$_1$-C$_4$)alkyl, —(C$_3$-C$_8$)cycloalkyl, —(C$_5$-C$_7$)heterocycloalkyl, —(C$_6$-C$_{10}$)aryl, and —(C$_5$-C$_7$)heteroaryl, wherein each —(C$_1$-C$_4$)alkyl, —(C$_3$-C$_8$)cycloalkyl, —(C$_5$-C$_7$)heterocycloalkyl, —(C$_6$-C$_{10}$)aryl, and —(C$_5$-C$_7$)heteroaryl is optionally substituted with 1 to 4 substituents independently selected from the group consisting of: —F, —Cl, —Br, —OH, —(C$_1$-C$_4$)alkyl, —O—(C$_1$-C$_4$)alkyl, —(C$_1$-C$_4$)alkylene-O—(C$_1$-C$_4$)alkyl, halo-substituted-(C$_1$-C$_4$)alkyl, halo-substituted-O—(C$_1$-C$_4$)alkyl, —C(O)—(C$_1$-C$_4$)alkyl, and —C(O)-(fluoro-substituted-(C$_1$-C$_4$)alkyl).

Alternatively, $R_5$ is selected from the group consisting of: H, —(C$_1$-C$_4$)alkyl, and —(C$_3$-C$_8$)cycloalkyl, wherein each —(C$_1$-C$_4$)alkyl and —(C$_3$-C$_8$)cycloalkyl is optionally substituted with 1 to 4 substituents independently selected from the group consisting of: —F, —Cl, —Br, —OH, —O—(C$_1$-C$_4$)alkyl, —(C$_1$-C$_4$)alkylene-O—(C$_1$-C$_4$)alkyl, halo-substituted-(C$_1$-C$_4$)alkyl, halo-substituted-O—(C$_1$-C$_4$)alkyl, —C(O)—(C$_1$-C$_4$)alkyl, and —C(O)-(fluoro-substituted-(C$_1$-C$_4$)alkyl).

Further, $R_5$ is selected from the group consisting of: H, —(C$_1$-C$_4$)alkyl, and —(C$_3$-C$_8$)cycloalkyl, wherein each —(C$_1$-C$_4$)alkyl and —(C$_3$-C$_8$)cycloalkyl is optionally substituted with 1 to 4 substituents independently selected from the group consisting of: —F, —Cl, —OH, —O—(C$_1$-C$_4$)alkyl, and halo-substituted-(C$_1$-C$_4$)alkyl. In another alternative, $R_5$ is selected from the group consisting of: H, methyl, ethyl, propyl, iso-propyl, butyl, tert-butyl, methoxy, hydroxyl, cyclobutyl, cyclopentyl, and cyclohexyl.

$R_6$ is selected from the group consisting of: H, —(C$_1$-C$_4$)alkyl, —(C$_3$-C$_8$)cycloalkyl, —(C$_5$-C$_7$)heterocycloalkyl, —(C$_6$-C$_{10}$)aryl, and —(C$_5$-C$_7$)heteroaryl, wherein each —(C$_1$-C$_4$)alkyl, —(C$_3$-C$_8$)cycloalkyl, —(C$_5$-C$_7$)heterocycloalkyl, —(C$_6$-C$_{10}$)aryl, and —(C$_5$-C$_7$)heteroaryl is optionally substituted with 1 to 4 substituents independently selected from the group consisting of: —F, —Cl, —Br, —OH, —(C$_1$-C$_4$)alkyl, —O—(C$_1$-C$_4$)alkyl, —(C$_1$-C$_4$)alkylene-O—(C$_1$-C$_4$)alkyl, halo-substituted-(C$_1$-C$_4$)alkyl, halo-substituted-O—(C$_1$-C$_4$)alkyl, —C(O)—(C$_1$-C$_4$)alkyl, and —C(O)-(fluoro-substituted-(C$_1$-C$_4$)alkyl).

Alternatively, $R_6$ is selected from the group consisting of: H, —(C$_1$-C$_4$)alkyl, and —(C$_3$-C$_8$)cycloalkyl, wherein each —(C$_1$-C$_4$)alkyl and —(C$_3$-C$_8$)cycloalkyl is optionally substituted with 1 to 4 substituents independently selected from the group consisting of: —F, —Cl, —Br, —OH, —(C$_1$-C$_4$)alkyl, —O—(C$_1$-C$_4$)alkyl, —(C$_1$-C$_4$)alkylene-O—(C$_1$-C$_4$)alkyl, halo-substituted-(C$_1$-C$_4$)alkyl, halo-substituted-O—(C$_1$-C$_4$)alkyl, —C(O)—(C$_1$-C$_4$)alkyl, and —C(O)-(fluoro-substituted-(C$_1$-C$_4$)alkyl).

Further, $R_6$ is selected from the group consisting of: H, —(C$_1$-C$_4$)alkyl, and —(C$_3$-C$_8$)cycloalkyl, wherein each —(C$_1$-C$_4$)alkyl and —(C$_3$-C$_8$)cycloalkyl is optionally substituted with 1 to 4 substituents independently selected from the group consisting of: —F, —Cl, —OH, —O—(C$_1$-C$_4$)alkyl, and halo-substituted-(C$_1$-C$_4$)alkyl. In another alternative, $R_6$ is selected from the group consisting of: H, methyl, ethyl, propyl, iso-propyl, butyl, tert-butyl, methoxy, hydroxyl, cyclobutyl, cyclopentyl, and cyclohexyl.

$R_7$ is selected from the group consisting of: H, —(C$_1$-C$_4$)alkyl, —(C$_3$-C$_8$)cycloalkyl, —(C$_5$-C$_7$)heterocycloalkyl, —(C$_6$-C$_{10}$)aryl, and —(C$_5$-C$_7$)heteroaryl, wherein each —(C$_1$-C$_4$)alkyl, —(C$_3$-C$_8$)cycloalkyl, —(C$_5$-C$_7$)heterocycloalkyl, —(C$_6$-C$_{10}$)aryl, and —(C$_5$-C$_7$)heteroaryl is optionally substituted with 1 to 4 substituents independently selected from the group consisting of: —F, —Cl, —Br, —OH, —(C$_1$-C$_4$)alkyl, —O—(C$_1$-C$_4$)alkyl, —(C$_1$-C$_4$)alkylene-O—(C$_1$-C$_4$)alkyl, halo-substituted-(C$_1$-C$_4$)alkyl, halo-substituted-O—(C$_1$-C$_4$)alkyl, —C(O)—(C$_1$-C$_4$)alkyl, and —C(O)-(fluoro-substituted-(C$_1$-C$_4$)alkyl).

Alternatively, $R_7$ is selected from the group consisting of: H, —(C$_1$-C$_4$)alkyl, and —(C$_3$-C$_8$)cycloalkyl wherein each —(C$_1$-C$_4$)alkyl and —(C$_3$-C$_8$)cycloalkyl is optionally substituted with 1 to 4 substituents independently selected from the group consisting of: —F, —Cl, —Br, —OH, —(C$_1$-C$_4$)alkyl, —O—(C$_1$-C$_4$)alkyl, —(C$_1$-C$_4$)alkylene-O—(C$_1$-C$_4$)alkyl, halo-substituted-(C$_1$-C$_4$)alkyl, halo-substituted-O—(C$_1$-C$_4$)alkyl, —C(O)—(C$_1$-C$_4$)alkyl, and —C(O)-(fluoro-substituted-(C$_1$-C$_4$)alkyl).

Further, $R_7$ is selected from the group consisting of: H, —(C$_1$-C$_4$)alkyl, and —(C$_3$-C$_8$)cycloalkyl, wherein each —(C$_1$-C$_4$)alkyl, and —(C$_3$-C$_8$)cycloalkyl is optionally substituted with 1 to 4 substituents independently selected from the group consisting of: —F, —Cl, —OH, —O—(C$_1$-C$_4$)alkyl, and halo-substituted-(C$_1$-C$_4$)alkyl. In another alternative, $R_7$ is selected from the group consisting of: H, methyl, ethyl, propyl, iso-propyl, butyl, tert-butyl, methoxy, hydroxyl, cyclobutyl, cyclopentyl, and cyclohexyl.

$R_8$ is selected from the group consisting of: H, —(C$_1$-C$_4$)alkyl, —(C$_3$-C$_8$)cycloalkyl, —(C$_5$-C$_7$)heterocycloalkyl, —($C_6$-$C_{10}$)aryl, and —($C_5$-$C_7$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl is optionally substituted with 1 to 4 substituents independently selected from the group consisting of: —F, —Cl, —Br, —OH, —($C_1$-$C_4$)alkyl, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, and —C(O)-(fluoro-substituted-($C_1$-$C_4$)alkyl).

Alternatively, $R_8$ is selected from the group consisting of: H, —($C_1$-$C_4$)alkyl, and —($C_3$-$C_8$)cycloalkyl wherein each —($C_1$-$C_4$)alkyl and —($C_3$-$C_8$)cycloalkyl is optionally substituted with 1 to 4 substituents independently selected from the group consisting of: —F, —Cl, —Br, —OH, —($C_1$-$C_4$)alkyl, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, and —C(O)-(fluoro-substituted-($C_1$-$C_4$)alkyl).

Further, $R_8$ is selected from the group consisting of: H, —($C_1$-$C_4$)alkyl, and —($C_3$-$C_8$)cycloalkyl, wherein each —($C_1$-$C_4$)alkyl, and —($C_3$-$C_8$)cycloalkyl is optionally substituted with 1 to 4 substituents independently selected from the group consisting of: —F, —Cl, —OH, —O—($C_1$-$C_4$)alkyl, and halo-substituted-($C_1$-$C_4$)alkyl. In another alternative, $R_8$ is selected from the group consisting of: H, methyl, ethyl, propyl, iso-propyl, butyl, tert-butyl, methoxy, hydroxyl, cyclobutyl, cyclopentyl, and cyclohexyl.

$R_9$ is selected from the group consisting of: H, —($C_1$-$C_6$)alkyl, —($C_0$-$C_6$)alkylene-cycloalkyl, —($C_0$-$C_6$)alkylene-heterocycloalkyl, —($C_0$-$C_6$)alkylene-aryl, —($C_0$-$C_6$)alkylene-heteroaryl, and —N=$CR_{11}R_{12}$, wherein each —($C_1$-$C_6$)alkyl, —($C_0$-$C_6$)alkylene-, -cycloalkyl, -heterocycloalkyl, -aryl, and -heteroaryl is optionally substituted with 1 to 4 substituents independently selected from the group consisting of: —F, —Cl, —Br, —OH, =O, —B(OH)$_2$, —($C_1$-$C_4$)alkyl, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, —C(O)-(fluoro-substituted-($C_1$-$C_4$)alkyl), —S(O)$_p$—($C_1$-$C_4$)alkyl, —$NR_{13}R_{14}$, and CN.

Alternatively, $R_9$ is selected from the group consisting of: H, —($C_1$-$C_6$)alkyl, —($C_0$-$C_6$)alkylene-heterocycloalkyl, —($C_0$-$C_6$)alkylene-aryl, and —($C_0$-$C_6$)alkylene-heteroaryl, wherein each —($C_1$-$C_6$)alkyl, —($C_0$-$C_6$)alkylene-, -heterocycloalkyl, -aryl, and -heteroaryl is optionally substituted with 1 to 4 substituents independently selected from the group consisting of: —F, —Cl, —Br, —OH, =O, —B(OH)$_2$, —($C_1$-$C_4$)alkyl, halo-substituted-($C_1$-$C_4$)alkyl, —C(O)—($C_1$-$C_4$)alkyl, and —C(O)-(fluoro-substituted-($C_1$-$C_4$)alkyl). Further, $R_9$ is selected from the group consisting of: H, —($C_1$-$C_4$)alkyl, —($C_1$-$C_3$)alkylene-heterocycloalkyl, —($C_1$-$C_3$)alkylene-aryl, and —($C_1$-$C_3$)alkylene-heteroaryl, wherein each —($C_1$-$C_4$)alkyl, —($C_1$-$C_3$)alkylene-, -heterocycloalkyl, -aryl, and -heteroaryl is optionally substituted with 1 to 3 substituents independently selected from the group consisting of —F, —Cl, —Br, —OH, =O, —B(OH)$_2$, —($C_1$-$C_4$)alkyl, halo-substituted-($C_1$-$C_4$)alkyl, —C(O)—($C_1$-$C_4$)alkyl, and —C(O)-(fluoro-substituted-($C_1$-$C_4$)alkyl).

Further, $R_9$ is selected from the group consisting of: H, methyl, ethyl, propyl, i-propyl, butyl, sec-butyl, t-butyl, and trifluoromethyl. Alternatively, $R_9$ is selected from the group consisting of —($C_1$-$C_3$)alkylene-morpholine, —($C_1$-$C_3$)alkylene-piperazine, —($C_1$-$C_3$)alkylene-phenyl, —($C_1$-$C_3$)alkylene-pyridyl, —($C_1$-$C_3$)alkylene-imidazolyl, —($C_1$-$C_3$)alkylene-azetidine, —($C_1$-$C_3$)alkylene-furanyl, —($C_1$-$C_3$)alkylene-pyrazinyl, —($C_1$-$C_3$)alkylene-oxazolyl, —($C_1$-$C_3$)alkylene-thienyl, —($C_1$-$C_3$)alkylene-thiazolyl, —($C_1$-$C_3$)alkylene-triazolyl, and —($C_1$-$C_3$)alkylene-isoxazolyl, wherein each —($C_1$-$C_3$)alkylene-, -morpholine, -piperazine, -phenyl, -pyridyl, and -imidazolyl is optionally substituted with 1 to 4 substituents independently selected from the group consisting of: —F, —Cl, OH, =O, —B(OH)$_2$, —($C_1$-$C_4$)alkyl, —C(O)—($C_1$-$C_4$)alkyl, and halo-substituted-($C_1$-$C_4$)alkyl.

In another alternative, $R_9$ is selected from the group consisting of —($C_1$-$C_3$)alkylene-morpholine, —($C_1$-$C_3$)alkylene-piperazine, —($C_1$-$C_3$)alkylene-phenyl, —($C_1$-$C_3$)alkylene-pyridyl, and —($C_1$-$C_3$)alkylene-imidazolyl, wherein each —($C_1$-$C_3$)alkylene-, -morpholine, -piperazine, -phenyl, -pyridyl, and -imidazolyl is optionally substituted with 1 to 4 substituents independently selected from the group consisting of: —F, —Cl, OH, =O, —B(OH)$_2$, —($C_1$-$C_4$)alkyl, —C(O)—($C_1$-$C_4$)alkyl, and halo-substituted-($C_1$-$C_4$)alkyl. Further, $R_9$ is selected from the group consisting of —($C_1$-$C_3$)alkylene-morpholine, —($C_1$-$C_3$)alkylene-piperazine, —($C_1$-$C_3$)alkylene-phenyl, —($C_1$-$C_3$)alkylene-pyridyl, and —($C_1$-$C_3$)alkylene-imidazolyl, wherein each —($C_1$-$C_3$)alkylene-, -morpholine, -piperazine, -phenyl, -pyridyl, and -imidazolyl is optionally substituted with 1 to 4 substituents independently selected from the group consisting of —B(OH)$_2$, and —($C_1$-$C_4$)alkyl.

Alternatively, $R_9$ is —N=$CR_{11}R_{12}$.

$R_{10}$ is selected from the group consisting of: H, —($C_1$-$C_6$)alkyl, —($C_0$-$C_6$)alkylene-cycloalkyl, —($C_0$-$C_6$)alkylene-heterocycloalkyl, —($C_0$-$C_6$)alkylene-aryl; and —($C_0$-$C_6$)alkylene-heteroaryl, wherein each —($C_1$-$C_6$)alkyl, —($C_0$-$C_6$)alkylene-, -cycloalkyl, -heterocycloalkyl, -aryl, and -heteroaryl is optionally substituted with 1 to 4 substituents independently selected from the group consisting of: —F, —Cl, —Br, —OH, =O, —B(OH)$_2$, ($C_1$-$C_4$) alkyl, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, —C(O)-(fluoro-substituted-($C_1$-$C_4$)alkyl), —S(O)$_q$—($C_1$-$C_4$)alkyl, —$NR_{15}R_{16}$ and CN.

Alternatively, $R_{10}$ is selected from the group consisting of: H, —($C_1$-$C_6$)alkyl, and —($C_1$-$C_6$)alkylene-heterocycloalkyl, wherein each —($C_1$-$C_6$)alkyl, —($C_1$-$C_6$)alkylene-, and -heterocycloalkyl is optionally substituted with 1 to 4 substituents independently selected from the group consisting of: —F, —Cl, —Br, —OH, =O, —B(OH)$_2$, —($C_1$-$C_4$) alkyl, —O—($C_1$-$C_4$)alkyl, —($C_1$-$C_4$)alkylene-O—($C_1$-$C_4$) alkyl, halo-substituted-($C_1$-$C_4$)alkyl, halo-substituted-O—($C_1$-$C_4$)alkyl, —C(O)—($C_1$-$C_4$)alkyl, —C(O)-(fluoro-substituted-($C_1$-$C_4$)alkyl), —S(O)$_q$—($C_1$-$C_4$)alkyl, —$NR_{15}R_{16}$ and CN.

Further, $R_{10}$ is selected from the group consisting of: H, —($C_1$-$C_6$)alkyl, and —($C_1$-$C_3$)alkylene-heterocycloalkyl, wherein each —($C_1$-$C_6$)alkyl, —($C_1$-$C_6$)alkylene-, and -heterocycloalkyl is optionally substituted with 1 to 3 substituents independently selected from the group consisting of: —F, —Cl, —Br, —OH, =O, —B(OH)$_2$, —($C_1$-$C_4$)alkyl, halo-substituted-($C_1$-$C_4$)alkyl, —C(O)—($C_1$-$C_4$)alkyl, and —C(O)-(fluoro-substituted-($C_1$-$C_4$)alkyl). Alternatively, Further, $R_{10}$ is selected from the group consisting of: H, methyl, ethyl, propyl, iso-propyl, butyl, sec-butyl, tert-butyl, trifluoromethyl, —($C_1$-$C_3$)alkylene-morpholine, —($C_1$-$C_3$)alkylene-piperazine, —($C_1$-$C_3$)alkylene-phenyl, —($C_1$-$C_3$)alkylene-pyridyl, and —($C_1$-$C_3$)alkylene-imidazolyl, wherein each —($C_1$-$C_3$)alkylene-, -morpholine, -piperazine, -phenyl, -pyridyl, and -imidazolyl is optionally substituted with 1 to 4 substituents independently selected from the group consisting of —B(OH)$_2$, and —($C_1$-$C_4$)alkyl.

$R_9$ and $R_{10}$ are taken together with the nitrogen atom to which they are bound form a 4-10-membered ring. Alternatively, $R_9$ and $R_{10}$ are taken together with the nitrogen atom to which they are bound form a 4-6-membered ring. Further, $R_9$ and $R_{10}$ are taken together with the nitrogen atom to which they are bound form a 4-6-membered ring cycloalkyl or heterocycloalkyl.

$R_{11}$ is H, —$(C_1$-$C_4)$alkyl, or —$(C_1$-$C_4)$alkylene-O—$(C_1$-$C_4)$alkyl, wherein each —$(C_1$-$C_4)$alkyl and —$(C_1$-$C_4)$alkylene-O—$(C_1$-$C_4)$alkyl is optionally substituted with 1 to 3 substituents independently selected from the group consisting of: —F, —Cl, —Br, and —OH. Alternatively, $R_{11}$ is H or —$(C_1$-$C_4)$alkyl optionally substituted with 1 to 3 substituents independently selected from the group consisting of: —F, —Cl, —Br, and —OH. Further, $R_{11}$ is H, methyl, ethyl, propyl, butyl, or trifluoromethyl. Specifically, $R_{11}$ is H or methyl.

$R_{12}$ is H, —$(C_1$-$C_4)$alkyl, —$(C_3$-$C_8)$cycloalkyl, —$(C_5$-$C_7)$heterocycloalkyl, —$(C_6$-$C_{10})$aryl, or —$(C_5$-$C_7)$heteroaryl, wherein each —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heteroaryl is optionally substituted with 1 to 4 substituents independently selected from the group consisting of: —F, —Cl, —Br, —OH, =O, —B(OH)$_2$, $(C_1$-$C_4)$alkyl, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, —C(O)-(fluoro-substituted-$(C_1$-$C_4)$alkyl), —S(O)$_r$—$(C_1$-$C_4)$alkyl, —S(O)$_2$—Na, and CN.

Alternatively, $R_{12}$ is H, —$(C_3$-$C_8)$cycloalkyl, —$(C_5$-$C_7)$heterocycloalkyl, —$(C_6$-$C_{10})$aryl, or —$(C_5$-$C_7)$heteroaryl, wherein each —$(C_3$-$C_8)$cycloalkyl, —$(C_5$-$C_7)$heterocycloalkyl, —$(C_6$-$C_{10})$aryl, and —$(C_5$-$C_7)$heteroaryl is optionally substituted with 1 to 4 substituents independently selected from the group consisting of: —F, —Cl, —Br, —OH, =O, —B(OH)$_2$, $(C_1$-$C_4)$alkyl, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, —C(O)-(fluoro-substituted-$(C_1$-$C_4)$alkyl), —S(O)$_r$—$(C_1$-$C_4)$alkyl, —S(O)$_2$—Na, and CN. Further, $R_{12}$ is H, —$(C_6$-$C_{10})$aryl, or —$(C_5$-$C_7)$heteroaryl, wherein each —$(C_6$-$C_{10})$aryl and —$(C_5$-$C_7)$heteroaryl is optionally substituted with 1 to 4 substituents independently selected from the group consisting of: —F, —Cl, —Br, —OH, =O, —B(OH)$_2$, $(C_1$-$C_4)$alkyl, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, —C(O)-(fluoro-substituted-$(C_1$-$C_4)$alkyl), —S(O)$_r$—$(C_1$-$C_4)$alkyl, —S(O)$_2$—Na, and CN.

In another alternative, $R_{12}$ is H, thiofuranyl, phenyl, naphthyl, biphenyl, tetrahydronaphthyl, indanyl, pyridyl, imidazolyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl, wherein each is optionally substituted with 1 to 4 substituents independently selected from the group consisting of: —F, —Cl, —Br, —OH, =O, —B(OH)$_2$, $(C_1$-$C_4)$alkyl, —O—$(C_1$-$C_4)$alkyl, —S(O)$_r$—$(C_1$-$C_4)$alkyl, —S(O)$_2$—Na, and CN. Alternatively, $R_{12}$ is H, phenyl, imidazolyl, furanyl, or indolyl, wherein each phenyl, imidazolyl, furanyl, or indolyl is optionally substituted with 1 to 4 substituents independently selected from the group consisting of: —F, —OH, methyl, —S(O)$_2$—Na, or —B(OH)$_2$, $R_{13}$ is selected from the group consisting of: H, —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heteroaryl, wherein each —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heteroaryl is optionally substituted with 1 to 4 substituents independently selected from the group consisting of: —F, —Cl, —Br, —OH, —$(C_1$-$C_4)$alkyl, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, and —C(O)-(fluoro-substituted-$(C_1$-$C_4)$alkyl).

Alternatively, $R_{13}$ is selected from the group consisting of: H, —$(C_1$-$C_4)$alkyl, and —$(C_3$-$C_8)$cycloalkyl, wherein each —$(C_1$-$C_4)$alkyl and —$(C_3$-$C_8)$cycloalkyl is optionally substituted with 1 to 4 substituents independently selected from the group consisting of: —F, —Cl, —Br, —OH, —$(C_1$-$C_4)$alkyl, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, and —C(O)-(fluoro-substituted-$(C_1$-$C_4)$alkyl).

Further, $R_{13}$ is selected from the group consisting of: H, —$(C_1$-$C_4)$alkyl, and —$(C_3$-$C_8)$cycloalkyl, wherein each —$(C_1$-$C_4)$alkyl and —$(C_3$-$C_8)$cycloalkyl is optionally substituted with 1 to 4 substituents independently selected from the group consisting of: —F, —Cl, —OH, —O—$(C_1$-$C_4)$ alkyl, and halo-substituted-$(C_1$-$C_4)$alkyl. In another alternative, $R_{13}$ is selected from the group consisting of: H, methyl, ethyl, propyl, iso-propyl, butyl, tert-butyl, methoxy, hydroxyl, cyclobutyl, cyclopentyl, and cyclohexyl.

$R_{14}$ is selected from the group consisting of: H, —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heteroaryl, wherein each —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heteroaryl is optionally substituted with 1 to 4 substituents independently selected from the group consisting of: —F, —Cl, —Br, —OH, —$(C_1$-$C_4)$alkyl, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, and —C(O)-(fluoro-substituted-$(C_1$-$C_4)$alkyl).

Alternatively, $R_{14}$ is selected from the group consisting of: H, —$(C_1$-$C_4)$alkyl, and —$(C_3$-$C_8)$cycloalkyl, wherein each —$(C_1$-$C_4)$alkyl and —$(C_3$-$C_8)$cycloalkyl is optionally substituted with 1 to 4 substituents independently selected from the group consisting of: —F, —Cl, —Br, —OH, —$(C_1$-$C_4)$alkyl, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, and —C(O)-(fluoro-substituted-$(C_1$-$C_4)$alkyl).

Further, $R_{14}$ is selected from the group consisting of: H, —$(C_1$-$C_4)$alkyl, and —$(C_3$-$C_8)$cycloalkyl, wherein each —$(C_1$-$C_4)$alkyl and —$(C_3$-$C_8)$cycloalkyl is optionally substituted with 1 to 4 substituents independently selected from the group consisting of: —F, —Cl, —OH, —O—$(C_1$-$C_4)$ alkyl, and halo-substituted-$(C_1$-$C_4)$alkyl. In another alternative, $R_{14}$ is selected from the group consisting of: H, methyl, ethyl, propyl, iso-propyl, butyl, tert-butyl, methoxy, hydroxyl, cyclobutyl, cyclopentyl, and cyclohexyl.

$R_{15}$ is selected from the group consisting of: H, —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heteroaryl, wherein each —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heteroaryl is optionally substituted with 1 to 4 substituents independently selected from the group consisting of: —F, —Cl, —Br, —OH, —$(C_1$-$C_4)$alkyl, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, and —C(O)-(fluoro-substituted-$(C_1$-$C_4)$alkyl).

Alternatively, $R_{15}$ is selected from the group consisting of: H, —$(C_1$-$C_4)$alkyl, and —$(C_3$-$C_8)$cycloalkyl, wherein each —(C₁-C₄)alkyl and —(C₃-C₈)cycloalkyl is optionally substituted with 1 to 4 substituents independently selected from the group consisting of: —F, —Cl, —Br, —OH, —(C₁-C₄)alkyl, —O—(C₁-C₄)alkyl, —(C₁-C₄)alkylene-O—(C₁-C₄)alkyl, halo-substituted-(C₁-C₄)alkyl, halo-substituted-O—(C₁-C₄)alkyl, —C(O)—(C₁-C₄)alkyl, and —C(O)-(fluoro-substituted-(C₁-C₄)alkyl).

Further, $R_{15}$ is selected from the group consisting of: H, —(C₁-C₄)alkyl, and —(C₃-C₈)cycloalkyl, wherein each —(C₁-C₄)alkyl and —(C₃-C₈)cycloalkyl is optionally substituted with 1 to 4 substituents independently selected from the group consisting of: —F, —Cl, —OH, —O—(C₁-C₄)alkyl, and halo-substituted-(C₁-C₄)alkyl. In another alternative, $R_{15}$ is selected from the group consisting of: H, methyl, ethyl, propyl, iso-propyl, butyl, tert-butyl, methoxy, hydroxyl, cyclobutyl, cyclopentyl, and cyclohexyl.

$R_{16}$ is selected from the group consisting of: H, —(C₁-C₄)alkyl, —(C₃-C₈)cycloalkyl, —(C₅-C₇)heterocycloalkyl, —(C₆-C₁₀)aryl, and —(C₅-C₇)heteroaryl, wherein each —(C₁-C₄)alkyl, —(C₃-C₈)cycloalkyl, —(C₅-C₇)heterocycloalkyl, —(C₆-C₁₀)aryl, and —(C₅-C₇)heteroaryl is optionally substituted with 1 to 4 substituents independently selected from the group consisting of: —F, —Cl, —Br, —OH, —(C₁-C₄)alkyl, —O—(C₁-C₄)alkyl, —(C₁-C₄)alkylene-O—(C₁-C₄)alkyl, halo-substituted-(C₁-C₄)alkyl, halo-substituted-O—(C₁-C₄)alkyl, —C(O)—(C₁-C₄)alkyl, and —C(O)-(fluoro-substituted-(C₁-C₄)alkyl).

Alternatively, $R_{16}$ is selected from the group consisting of: H, —(C₁-C₄)alkyl, and —(C₃-C₈)cycloalkyl, wherein each —(C₁-C₄)alkyl and —(C₃-C₈)cycloalkyl is optionally substituted with 1 to 4 substituents independently selected from the group consisting of: —F, —Cl, —Br, —OH, —(C₁-C₄)alkyl, —O—(C₁-C₄)alkyl, —(C₁-C₄)alkylene-O—(C₁-C₄)alkyl, halo-substituted-(C₁-C₄)alkyl, halo-substituted-O—(C₁-C₄)alkyl, —C(O)—(C₁-C₄)alkyl, and —C(O)-(fluoro-substituted-(C₁-C₄)alkyl).

Further, $R_{16}$ is selected from the group consisting of: H, —(C₁-C₄)alkyl, and —(C₃-C₈)cycloalkyl, wherein each —(C₁-C₄)alkyl and —(C₃-C₈)cycloalkyl is optionally substituted with 1 to 4 substituents independently selected from the group consisting of: —F, —Cl, —OH, —O—(C₁-C₄)alkyl, and halo-substituted-(C₁-C₄)alkyl. In another alternative, $R_{16}$ is selected from the group consisting of: H, methyl, ethyl, propyl, iso-propyl, butyl, tert-butyl, methoxy, hydroxyl, cyclobutyl, cyclopentyl, and cyclohexyl.

$R_C$ is selected from the group consisting of: —F, —Cl, —Br, —OH, —(C₁-C₄)alkyl, —O—(C₁-C₄)alkyl, —(C₁-C₄)alkylene-O—(C₁-C₄)alkyl, halo-substituted-(C₁-C₄)alkyl, halo-substituted-O—(C₁-C₄)alkyl, —C(O)—(C₁-C₄)alkyl, —C(O)-(fluoro-substituted-(C₁-C₄)alkyl), —S(O)ₒ—(C₁-C₄)alkyl, —NR₇R₈ and CN.

Alternatively $R_C$ is selected from the group consisting of: —F, —Cl, —Br, —OH, and —O—(C₁-C₄)alkyl. In another alternative, $R_C$ is selected from the group consisting of F, —Cl, —Br, —OH, methoxy, and ethoxy.

m is 0, 1, 2, or 3. Alternatively, m is 1 or 2.
o is 1 or 2.
p is 1 or 2.
q is 1 or 2.
r is 1 or 2.

A first embodiment of the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by Structural Formula I:

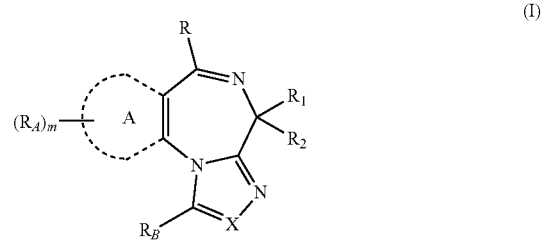

or a pharmaceutically acceptable salt thereof, wherein:
X is N or CR₃;
$R_3$ is selected from the group consisting of: H, —(C₁-C₄)alkyl, —(C₃-C₈)cycloalkyl, —(C₅-C₇)heterocycloalkyl, —(C₆-C₁₀)aryl, and —(C₅-C₁₀)heteroaryl, wherein each —(C₁-C₄)alkyl, —(C₃-C₈)cycloalkyl, —(C₅-C₇)heterocycloalkyl, —(C₆-C₁₀)aryl, and —(C₅-C₁₀)heteroaryl is optionally and independently substituted with 1 to 4 substituents;
$R_B$ is H, —(C₁-C₄)alkyl, —(C₁-C₄)alkylene-O—(C₁-C₄)alkyl, or —COO—R₄, wherein each —(C₁-C₄)alkyl and —(C₁-C₄)alkylene-O—(C₁-C₄)alkyl is optionally substituted with 1 to 4 substituents independently selected from the group consisting of —F, —Cl, —Br, —OH, and —NR₅R₆;
ring A is —(C₆-C₁₀)aryl or —(C₅-C₁₀)heteroaryl;
each $R_4$ is independently H, —(C₁-C₄)alkyl, —(C₃-C₈)cycloalkyl, —(C₅-C₇)heterocycloalkyl, —(C₆-C₁₀)aryl, or —(C₅-C₁₀)heteroaryl, wherein each —(C₁-C₄)alkyl, —(C₃-C₈)cycloalkyl, —(C₅-C₇)heterocycloalkyl, —(C₆-C₁₀)aryl, and —(C₅-C₁₀)heteroaryl is optionally and independently substituted with 1 to 4 substituents; or any two $R_4$ together with the atoms to which each is bound form a fused aryl or heteroaryl group;
R is —(C₁-C₄)alkyl, —(C₃-C₈)cycloalkyl, —(C₅-C₇)heterocycloalkyl, —(C₆-C₁₀)aryl, or —(C₅-C₁₀)heteroaryl, wherein each is optionally and independently substituted with 1 to 4 substituents;
$R_1$ is —(CH₂)ₙ-L, in which n is 0-3 and L is H, —C(O)O—R₉, —CO—N(R₉R₁₀), —NR₉R₁₀, —N(R₁₀)C(O)OR₉, or —N(R₁₀)C(O)R₉;
$R_2$ is H, D, halogen, or —(C₁-C₄)alkyl;
$R_4$, $R_5$, and $R_6$ are each independently selected from the group consisting of: H, —(C₁-C₄)alkyl, —(C₃-C₈)cycloalkyl, —(C₅-C₇)heterocycloalkyl, —(C₆-C₁₀)aryl, and —(C₅-C₇)heteroaryl, wherein each —(C₁-C₄)alkyl, —(C₃-C₈)cycloalkyl, —(C₅-C₇)heterocycloalkyl, —(C₆-C₁₀)aryl, and —(C₅-C₇)heteroaryl is optionally and independently substituted with 1 to 4 substituents;
$R_9$ is selected from the group consisting of: H, —(C₁-C₆)alkyl, —(C₀-C₆)alkylene-cycloalkyl, —(C₀-C₆)alkylene-heterocycloalkyl, —(C₀-C₆)alkylene-aryl, —(C₀-C₆)alkylene-heteroaryl, and —N=CR₁₁R₁₂, wherein each —(C₁-C₆)alkyl and —(C₀-C₆)alkylene- is optionally and independently substituted with 1 to 4 substituents and each -cycloalkyl, -heterocycloalkyl, -aryl, and -heteroaryl is optionally and independently substituted with 1 to 4 substituents;
$R_{10}$ is selected from the group consisting of: H, —(C₁-C₆)alkyl, —(C₀-C₆)alkylene-cycloalkyl, —(C₀-C₆)alkylene-heterocycloalkyl, —(C₀-C₆)alkylene-aryl; and —($C_0$-$C_6$)alkylene-heteroaryl, wherein each —($C_1$-$C_6$)alkyl and —($C_0$-$C_6$)alkylene- is optionally and independently substituted with 1 to 4 substituents and each -cycloalkyl, -heterocycloalkyl, -aryl, and -heteroaryl is optionally and independently substituted with 1 to 4 substituents;

$R_9$ and $R_{10}$ are taken together with the nitrogen atom to which they are bound form a 4-10-membered ring;

$R_{11}$ is H, —($C_1$-$C_4$)alkyl, or —($C_1$-$C_4$)alkylene-O—($C_1$-$C_4$)alkyl, wherein each —($C_1$-$C_4$)alkyl and —($C_1$-$C_4$)alkylene-O—($C_1$-$C_4$)alkyl is optionally and independently substituted with 1 to 3 substituents selected from the group consisting of: —F, —Cl, —Br, and —OH;

$R_{12}$ is H, —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_7$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl is optionally and independently substituted with 1 to 4 substituents; and m is 0, 1, 2, or 3.

In a particular embodiment, the condition associated with hyperinsulinaemia is an insulinoma.

In a specific embodiment, the condition associated with hyperinsulinaemia is congenital hyperinsulinism.

In a first aspect of the first embodiment or the particular or specific embodiment thereof: X is N.

In a second aspect of first embodiment or the particular or specific embodiment thereof: $R_B$ is H or —($C_1$-$C_4$)alkyl.

In a third aspect of the first embodiment or the particular or specific embodiment thereof: ring A is 5- or 6-membered aryl or heteroaryl.

In a fourth aspect of the first embodiment or the particular or specific embodiment thereof: ring A is phenyl or thienyl.

In a fifth aspect of the first embodiment or the particular or specific embodiment thereof: R is —($C_6$-$C_{10}$)aryl or —($C_5$-$C_{10}$)heteroaryl optionally substituted with 1 to 4 substituents independently selected from the group consisting of: —F, —Cl, and —Br.

In a fifth aspect of the first embodiment or the particular or specific embodiment thereof: L is H, —COO—$R_9$, or —CO—N($R_9R_{10}$).

In a sixth aspect of the first embodiment or the particular or specific embodiment thereof: each $R_9$ is independently selected from the group consisting of —($C_1$-$C_6$)alkyl, —($C_0$-$C_6$)alkylene-heterocycloalkyl, —($C_0$-$C_6$)alkylene-aryl, and —($C_0$-$C_6$)alkylene-heteroaryl and each —($C_1$-$C_6$)alkyl, -heterocycloalkyl, -aryl, and -heteroaryl is optionally substituted with 1 to 4 substituents independently selected from the group consisting of —F, —Cl, —Br, and —($C_1$-$C_6$)alkyl.

In a seventh aspect of the first embodiment or the particular or specific embodiment thereof: each $R_{10}$ is independently selected from the group consisting of: H and —($C_1$-$C_6$)alkyl.

In an eighth aspect of the first embodiment or the particular or specific embodiment thereof: wherein $R_2$ is selected from the group consisting of: H and methyl.

In a ninth aspect of the first embodiment or the particular or specific embodiment thereof: $R_A$ is independently H or —($C_1$-$C_4$)alkyl, or any two $R_A$ together with the atoms to which each is attached, can form a fused aryl.

In a tenth aspect of the first embodiment or the particular or specific embodiment thereof: m is 2 and and at least one $R_A$ is methyl.

In an eleventh aspect of the first embodiment or the particular or specific embodiment thereof: m is 2 and each $R_A$ is methyl.

In a second embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by Structural Formula II:

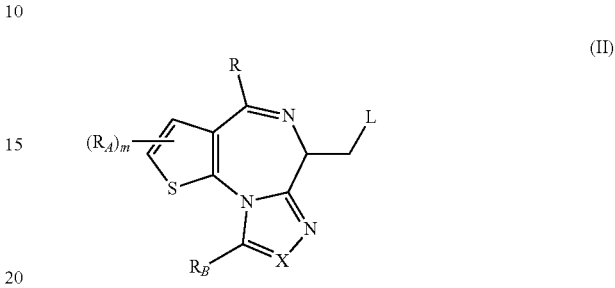

or a pharmaceutically acceptable salt thereof, wherein:

X is N or $CR_3$;

$R_3$ is selected from the group consisting of: H, —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl is optionally and independently substituted with 1 to 4 substituents;

$R_B$ is H, —($C_1$-$C_4$)alkyl, —($C_1$-$C_4$)alkylene-O—($C_1$-$C_4$)alkyl, or —COO—$R_4$, wherein each —($C_1$-$C_4$)alkyl and —($C_1$-$C_4$)alkylene-O—($C_1$-$C_4$)alkyl is optionally substituted with 1 to 4 substituents independently selected from the group consisting of —F, —Cl, —Br, —OH, and —$NR_5R_6$;

each $R_A$ is independently H, —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_{10}$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl is optionally and independently substituted with 1 to 4 substituents; or any two $R_A$ together with the atoms to which each is bound form a fused aryl or heteroaryl group;

R is —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_{10}$)heteroaryl, wherein each is optionally and independently substituted with 1 to 4 substituents;

L is H, —C(O)O—$R_9$, —CO—N($R_9R_{10}$), —$NR_9R_{10}$, —N($R_{10}$)C(O)O$R_9$, or —N($R_{10}$)C(O)$R_9$;

$R_4$, $R_5$, and $R_6$ are each independently selected from the group consisting of: H, —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl is optionally and independently substituted with 1 to 4 substituents;

$R_9$ is selected from the group consisting of: H, —($C_1$-$C_6$)alkyl, —($C_0$-$C_6$)alkylene-cycloalkyl, —($C_0$-$C_6$)alkylene-heterocycloalkyl, —($C_0$-$C_6$)alkylene-aryl, —($C_0$-$C_6$)alkylene-heteroaryl, and —N=$CR_{11}R_{12}$, wherein each —($C_1$-$C_6$)alkyl and —($C_0$-$C_6$)alkylene- is optionally and independently substituted with 1 to 4 substituents and each -cycloalkyl, -heterocycloalkyl, -aryl, and -heteroaryl is optionally and independently substituted with 1 to 4 substituents;

$R_{10}$ is selected from the group consisting of: H, —($C_1$-$C_6$)alkyl, —($C_0$-$C_6$)alkylene-cycloalkyl, —($C_0$-$C_6$)alkylene-heterocycloalkyl, —($C_0$-$C_6$)alkylene-aryl; and —($C_0$-$C_6$)alkylene-heteroaryl, wherein each —($C_1$-$C_6$)alkyl and —($C_0$-$C_6$)alkylene- is optionally and independently substituted with 1 to 4 substituents and each -cycloalkyl, -heterocycloalkyl, -aryl, and -heteroaryl is optionally and independently substituted with 1 to 4 substituents;

$R_9$ and $R_{10}$ are taken together with the nitrogen atom to which they are bound form a 4-10-membered ring;

$R_{11}$ is H, —($C_1$-$C_4$)alkyl, or —($C_1$-$C_4$)alkylene-O—($C_1$-$C_4$)alkyl, wherein each —($C_1$-$C_4$)alkyl and —($C_1$-$C_4$)alkylene-O—($C_1$-$C_4$)alkyl is optionally substituted with 1 to 3 substituents selected from the group consisting of: —F, —Cl, —Br, and —OH;

$R_{12}$ is H, —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_7$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl is optionally and independently substituted with 1 to 4 substituents; and m is 0, 1, 2, or 3.

In a particular embodiment, the condition associated with hyperinsulinaemia is an insulinoma.

In a specific embodiment, the condition associated with hyperinsulinaemia is congenital hyperinsulinism.

In a first aspect of the second embodiment or the particular or specific embodiment thereof: X is N.

In a second aspect of the second embodiment or the particular or specific embodiment thereof: $R_B$ is selected from the group consisting of: H, —($C_1$-$C_4$) alkyl, and —($C_1$-$C_4$)alkylene-O—($C_1$-$C_4$)alkyl, and each —($C_1$-$C_4$) alkyl and —($C_1$-$C_4$)alkylene-O—($C_1$-$C_4$)alkyl is optionally substituted with 1 to 4 substituents independently selected from the group consisting of: —F, —Cl, —Br, and —OH.

In a third aspect of the second embodiment or the particular or specific embodiment thereof: $R_B$ is methyl, ethyl, hydroxy methyl, methoxymethyl, or trifluoromethyl.

In a fourth aspect of the second embodiment or the particular or specific embodiment thereof: R is —($C_6$-$C_{10}$) aryl, or —($C_5$-$C_{10}$)heteroaryl optionally substituted with a substituent selected from the group consisting of: —F, —Cl, and —Br.

In a fifth aspect of the second embodiment or the particular or specific embodiment thereof: R is phenyl or pyridyl optionally substituted with a substituent selected from the group consisting of: —F, —Cl, and —Br.

In a sixth aspect of the second embodiment or the particular or specific embodiment thereof: R is p-Cl-phenyl, o-Cl-phenyl, m-Cl-phenyl, p-F-phenyl, o-F-phenyl, m-F-phenyl or pyridinyl.

In a seventh aspect of the second embodiment or the particular or specific embodiment thereof: L is —CO—N ($R_9R_{10}$), $R_9$ is —($C_0$-$C_6$)alkylene-heterocycloalkyl, —($C_0$-$C_6$) alkylene-aryl, or —($C_0$-$C_6$)alkylene-heteroaryl, wherein each -heterocycloalkyl, -aryl, and -heteroaryl is optionally and independently substituted with 1 to 4 ($C_1$-$C_4$)alkyl, and $R_{10}$ is H or —($C_1$-$C_6$)alkyl.

In an eighth aspect of the second embodiment or the particular or specific embodiment thereof: L is —COO—$R_9$ and $R_9$ is independently selected from the group consisting of: —($C_1$-$C_6$)alkyl, —($C_0$-$C_6$)alkylene -heterocycloalkyl, —($C_0$-$C_6$)alkylene-aryl, and —($C_0$-$C_6$)alkylene-heteroaryl, wherein each —($C_1$-$C_6$)alkyl, -heterocycloalkyl, -aryl, and -heteroaryl is optionally substituted with 1 to 4 substituents independently selected from the group consisting of: —F, —Cl, —Br, and —($C_1$-$C_6$)alkyl.

In a ninth aspect of the second embodiment or the particular or specific embodiment thereof: L is —COO—$R_9$, and $R_9$ is selected from the group consisting of: methyl, ethyl, propyl, i-propyl, butyl, sec-butyl, t-butyl, and trifluoromethyl.

In a tenth aspect of the second embodiment or the particular or specific embodiment thereof: each $R_A$ is independently H or —($C_1$-$C_4$)alkyl, or any two $R_A$ together with the atoms to which each is attached, can form a fused aryl.

In an eleventh aspect of the second embodiment or the particular or specific embodiment thereof: m is 2, and at least one occurrence of $R_A$ is methyl.

In a twelfth aspect of the second embodiment or the particular or specific embodiment thereof: m is 2 and each $R_A$ is methyl.

In a third embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by Structural Formula III:

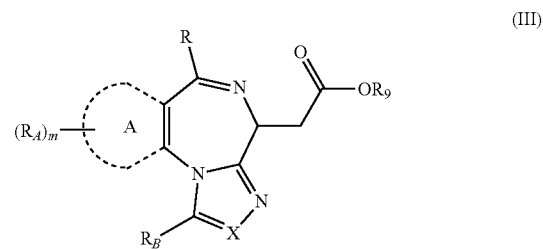

(III)

or a pharmaceutically acceptable salt thereof, wherein:

X is N or $CR_3$;

$R_3$ is selected from the group consisting of: H, —($C_1$-$C_4$) alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl is optionally and independently substituted with 1 to 4 substituents;

$R_B$ is H, —($C_1$-$C_4$)alkyl, —($C_1$-$C_4$)alkylene-O—($C_1$-$C_4$) alkyl, or —COO—$R_4$, wherein each —($C_1$-$C_4$)alkyl and —($C_1$-$C_4$)alkylene-O—($C_1$-$C_4$)alkyl is optionally substituted with 1 to 4 substituents independently selected from the group consisting of —F, —Cl, —Br, —OH, and —$NR_5R_6$;

ring A is —($C_6$-$C_{10}$)aryl or —($C_5$-$C_{10}$)heteroaryl;

each $R_A$ is independently H, —($C_1$-$C_4$)alkyl, —($C_3$-$C_8$) cycloalkyl, —($C_5$-$C_7$) heterocycloalkyl, —($C_6$-$C_{10}$)aryl, or —($C_5$-$C_{10}$)heteroaryl, wherein each —($C_1$-$C_4$)alkyl, —($C_3$-$C_8$)cycloalkyl, —($C_5$-$C_7$) heterocycloalkyl, —($C_6$-$C_{10}$)aryl, and —($C_5$-$C_{10}$)heteroaryl is optionally and independently substituted with 1 to 4 substituents; or any two $R_A$ together with the atoms to which each is bound form a fused aryl or heteroaryl group;

R is —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_{10}$)heteroaryl, wherein each is optionally and independently substituted with 1 to 4 substituents;

$R_4$, $R_5$, and $R_6$ are each independently selected from the group consisting of: H, —($C_1$-$C_4$)alkyl, —($C_3$-$C_8$)cycloalkyl, —($C_5$-$C_7$)heterocycloalkyl, —($C_6$-$C_{10}$)aryl, and —($C_5$-

$C_7$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl is optionally and independently substituted with 1 to 4 substituents;

$R_9$ is selected from the group consisting of: H, —($C_1$-$C_6$) alkyl, —($C_0$-$C_6$)alkylene-cycloalkyl, —($C_0$-$C_6$)alkylene-heterocycloalkyl, —($C_0$-$C_6$)alkylene-aryl, and —($C_0$-$C_6$)alkylene-heteroaryl, wherein each —($C_1$-$C_6$)alkyl and —($C_0$-$C_6$)alkylene- is optionally and independently substituted with 1 to 4 substituents and each -cycloalkyl, -heterocycloalkyl, -aryl, and -heteroaryl is optionally and independently substituted with 1 to 4 substituents; and m is 0, 1, 2, or 3.

In a particular embodiment, the condition associated with hyperinsulinaemia is an insulinoma.

In a specific embodiment, the condition associated with hyperinsulinaemia is congenital hyperinsulinism.

In a first aspect of the third embodiment or the particular or specific embodiment thereof: X is N.

In a second aspect of the third embodiment or the particular or specific embodiment thereof: $R_B$ is selected from the group consisting of: H, —($C_1$-$C_4$) alkyl, and —($C_1$-$C_4$) alkylene-O—($C_1$-$C_4$)alkyl, and each —($C_1$-$C_4$) alkyl and —($C_1$-$C_4$)alkylene-O—($C_1$-$C_4$)alkyl is optionally substituted with 1 to 4 substituents independently selected from the group consisting of —F, —Cl, —Br, and —OH.

In a third aspect of the third embodiment or the particular or specific embodiment thereof: $R_B$ is methyl, ethyl, hydroxy methyl, methoxymethyl, or trifluoromethyl.

In a fourth aspect of the third embodiment or the particular or specific embodiment thereof: ring A is 5- or 6-membered aryl or heteroaryl.

In a fifth aspect of the third embodiment or the particular or specific embodiment thereof: ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In a sixth aspect of the third embodiment or the particular or specific embodiment thereof: ring A is phenyl or thienyl.

In a seventh aspect of the third embodiment or the particular or specific embodiment thereof: R is —($C_6$-$C_{10}$) aryl or —($C_5$-$C_{10}$)heteroaryl optionally substituted with a substituent selected from the group consisting of: —F, —Cl, and —Br.

In an eighth aspect of the third embodiment or the particular or specific embodiment thereof: R is phenyl or pyridyl optionally substituted with 1-4 substituents independently selected from the group consisting of: —F, —Cl, and —Br.

In a ninth aspect of the third embodiment or the particular or specific embodiment thereof: R is p-Cl-phenyl, o-Cl-phenyl, m-Cl-phenyl, p-F-phenyl, o-F-phenyl, m-F-phenyl or pyridinyl.

In a tenth aspect of the third embodiment or the particular or specific embodiment thereof: each $R_A$ is independently H or —($C_1$-$C_4$)alkyl, or any two $R_A$ together with the atoms to which each is attached, can form a fused aryl.

In an eleventh aspect of the third embodiment or the particular or specific embodiment thereof: m is 2, and at least one occurrence of $R_A$ is methyl.

In a twelfth aspect of the third embodiment or the particular or specific embodiment thereof: m is 2 and each $R_A$ is methyl.

In a thirteenth aspect of the third embodiment or the particular or specific embodiment thereof: $R_9$ is independently selected from the group consisting of —($C_1$-$C_6$)alkyl, —($C_0$-$C_6$)alkylene-heterocycloalkyl, —($C_0$-$C_6$)alkylene-aryl, and —($C_0$-$C_6$)alkylene-heteroaryl and each —($C_1$-$C_6$) alkyl, -heterocycloalkyl, -aryl, and -heteroaryl is optionally substituted with 1 to 4 substituents independently selected from the group consisting of —F, —Cl, —Br, and —($C_1$-$C_6$)alkyl.

In a fourteenth aspect of the third embodiment or the particular or specific embodiment thereof: $R_9$ is selected from the group consisting of: methyl, ethyl, propyl, i-propyl, butyl, sec-butyl, t-butyl, and trifluoromethyl.

In a fourth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by Structural Formula IV:

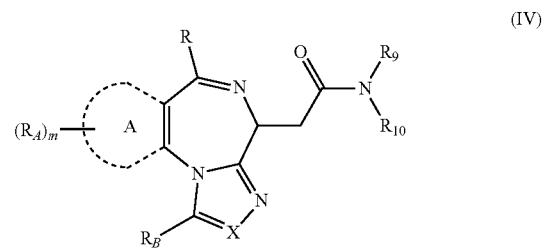

(IV)

or a pharmaceutically acceptable salt thereof, wherein:

X is N or $CR_3$;

$R_3$ is selected from the group consisting of: H, —($C_1$-$C_4$) alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_{10}$)heteroaryl is optionally and independently substituted with 1 to 4 substituents;

$R_B$ is H, —($C_1$-$C_4$)alkyl, —($C_1$-$C_4$)alkylene-O—($C_1$-$C_4$) alkyl, or —COO—$R_4$, wherein each —($C_1$-$C_4$)alkyl and —($C_1$-$C_4$)alkylene-O—($C_1$-$C_4$)alkyl is optionally substituted with 1 to 4 substituents independently selected from the group consisting of —F, —Cl, —Br, —OH, and —$NR_5R_6$;

ring A is aryl or heteroaryl;

each $R_A$ is independently H, —($C_1$-$C_4$)alkyl, —($C_3$-$C_8$) cycloalkyl, —($C_5$-$C_7$) heterocycloalkyl, —($C_6$-$C_{10}$)aryl, or —($C_5$-$C_{10}$)heteroaryl, wherein each —($C_1$-$C_4$)alkyl, —($C_3$-$C_8$)cycloalkyl, —($C_5$-$C_7$) heterocycloalkyl, —($C_6$-$C_{10}$)aryl, and —($C_5$-$C_{10}$)heteroaryl is optionally and independently substituted with 1 to 4 substituents; or any two $R_A$ together with the atoms to which each is bound form a fused aryl or heteroaryl group;

R is —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_{10}$)heteroaryl, wherein each is optionally and independently substituted with 1 to 4 substituents;

$R_4$, $R_5$, and $R_6$ are each independently selected from the group consisting of: H, —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl is optionally and independently substituted with 1 to 4 substituents;

$R_9$ is selected from the group consisting of: H, —($C_1$-$C_6$) alkyl, —($C_0$-$C_6$)alkylene-cycloalkyl, —($C_0$-$C_6$)alkylene-heterocycloalkyl, —($C_0$-$C_6$)alkylene-aryl, —($C_0$-$C_6$)alkylene-heteroaryl, and —N=$CR_{11}R_{12}$, wherein each —($C_1$-$C_6$)alkyl and —($C_0$-$C_6$)alkylene- is optionally and independently substituted with 1 to 4 substituents and each -cycloalkyl, -heterocycloalkyl, -aryl, and -heteroaryl is optionally and independently substituted with 1 to 4 substituents;

$R_{10}$ is selected from the group consisting of: H, —($C_1$-$C_6$)alkyl, —($C_0$-$C_6$)alkylene-cycloalkyl, —($C_0$-$C_6$)alkylene-heterocycloalkyl, —($C_0$-$C_6$)alkylene-aryl; and —($C_0$-$C_6$)alkylene-heteroaryl, wherein each —($C_1$-$C_6$)alkyl and —($C_0$-$C_6$)alkylene- is optionally and independently substituted with 1 to 4 substituents and each -cycloalkyl, -heterocycloalkyl, -aryl, and -heteroaryl is optionally and independently substituted with 1 to 4 substituents;

$R_9$ and $R_{10}$ are taken together with the nitrogen atom to which they are bound form a 4-10-membered ring;

$R_{11}$ is H, —($C_1$-$C_4$)alkyl, or —($C_1$-$C_4$)alkylene-O—($C_1$-$C_4$)alkyl, wherein each —($C_1$-$C_4$)alkyl and —($C_1$-$C_4$)alkylene-O—($C_1$-$C_4$)alkyl is optionally substituted with 1 to 3 substituents selected from the group consisting of: —F, —Cl, —Br, and —OH;

$R_{12}$ is H, —($C_1$-$C_4$)alkyl, —($C_3$-$C_8$)cycloalkyl, —($C_5$-$C_7$)heterocycloalkyl, —($C_6$-$C_{10}$)aryl, or —($C_5$-$C_7$)heteroaryl, wherein each —($C_1$-$C_4$)alkyl, —($C_3$-$C_8$)cycloalkyl, —($C_5$-$C_7$)heterocycloalkyl, —($C_6$-$C_{10}$)aryl, and —($C_5$-$C_7$)heteroaryl is optionally and independently substituted with 1 to 4 substituents; and m is 0, 1, 2, or 3.

In a particular embodiment, the condition associated with hyperinsulinaemia is an insulinoma.

In a specific embodiment, the condition associated with hyperinsulinaemia is congenital hyperinsulinism.

In a first aspect of the fourth embodiment or the particular or specific embodiment thereof: X is N.

In a second aspect of the fourth embodiment or the particular or specific embodiment thereof: $R_B$ is selected from the group consisting of: H, —($C_1$-$C_4$) alkyl, and —($C_1$-$C_4$)alkylene-O—($C_1$-$C_4$)alkyl, and each —($C_1$-$C_4$) alkyl and —($C_1$-$C_4$)alkylene-O—($C_1$-$C_4$)alkyl is optionally substituted with 1 to 4 substituents independently selected from the group consisting of —F, —Cl, —Br, and —OH.

In a third aspect of the fourth embodiment or the particular or specific embodiment thereof: $R_B$ is methyl, ethyl, hydroxy methyl, methoxymethyl, or trifluoromethyl.

In a fourth aspect of the fourth embodiment or the particular or specific embodiment thereof: ring A is 5- or 6-membered aryl or heteroaryl.

In a fifth aspect of the fourth embodiment or the particular or specific embodiment thereof: ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In a sixth aspect of the fourth embodiment or the particular or specific embodiment thereof: ring A is phenyl or thienyl.

In a seventh aspect of the fourth embodiment or the particular or specific embodiment thereof: R is —($C_6$-$C_{10}$) aryl, or —($C_5$-$C_{10}$)heteroaryl optionally substituted with 1 to 4 substituents independently selected from the group consisting of: —F, —Cl, and —Br.

In an eighth aspect of the fourth embodiment or the particular or specific embodiment thereof: R is phenyl or pyridyl optionally substituted with 1 to 4 substituents independently selected from the group consisting of: —F, —Cl, and —Br.

In a ninth aspect of the fourth embodiment or the particular or specific embodiment thereof: R is p-Cl-phenyl, o-Cl-phenyl, m-Cl-phenyl, p-F-phenyl, o-F-phenyl, m-F-phenyl or pyridinyl.

In a tenth aspect of the fourth embodiment or the particular or specific embodiment thereof: each $R_A$ is independently H or —($C_1$-$C_4$)alkyl, or any two $R_A$ together with the atoms to which each is attached, can form a fused aryl.

In an eleventh aspect of the fourth embodiment or the particular or specific embodiment thereof: m is 2, and at least one occurrence of $R_A$ is methyl.

In a twelfth aspect of the fourth embodiment or the particular or specific embodiment thereof: m is 2 and each $R_A$ is methyl.

In a thirteenth aspect of the fourth embodiment or the particular or specific embodiment thereof: $R_9$ is independently selected from the group consisting of —($C_1$-$C_6$)alkyl, —($C_0$-$C_6$)alkylene-heterocycloalkyl, —($C_0$-$C_6$)alkylene-aryl, and —($C_0$-$C_6$)alkylene-heteroaryl and each —($C_1$-$C_6$) alkyl, -heterocycloalkyl, -aryl, and -heteroaryl is optionally substituted with 1 to 4 substituents independently selected from the group consisting of —F, —Cl, —Br, and —($C_1$-$C_6$)alkyl.

In a fourteenth aspect of the fourth embodiment or the particular or specific embodiment thereof: $R_{10}$ is selected from the group consisting of: H and —($C_1$-$C_6$)alkyl optionally substituted with 1 to 4 substituents independently selected from the group consisting of —F, and —O—($C_1$-$C_6$)alkyl.

In a fifteenth aspect of the fourth embodiment or the particular or specific embodiment thereof: $R_9$ is N=$CR_{11}R_{12}$, $R_{11}$ is H or —($C_1$-$C_4$)alkyl and $R_{12}$ is —($C_5$-$C_7$)heterocycloalkyl, —($C_6$-$C_{10}$)aryl or —($C_5$-$C_7$)heteroaryl, optionally substituted with 1 to 4 substituents independently selected from —($C_1$-$C_4$)alkyl, —F, —Cl, —$SO_2$Na, or —B(OH)$_2$.

In a fifth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by Structural Formula V:

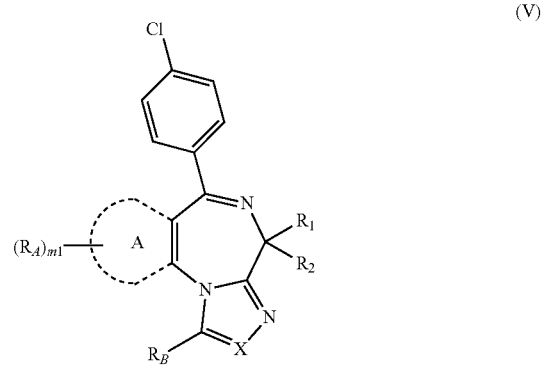

(V)

or a pharmaceutically acceptable salt thereof, wherein:

X is N or $CR_3$;

$R_3$ is selected from the group consisting of: H, —$(C_1-C_4)$alkyl, —$(C_3-C_8)$cycloalkyl, —$(C_5-C_7)$heterocycloalkyl, —$(C_6-C_{10})$aryl, and —$(C_5-C_{10})$heteroaryl, wherein each —$(C_1-C_4)$alkyl, —$(C_3-C_8)$cycloalkyl, —$(C_5-C_7)$heterocycloalkyl, —$(C_6-C_{10})$aryl, and —$(C_5-C_{10})$heteroaryl is optionally and independently substituted with 1 to 4 substituents;

$R_B$ is H, —$(C_1-C_4)$alkyl, —$(C_1-C_4)$alkylene-O—$(C_1-C_4)$alkyl, or —COO—$R_4$, wherein each —$(C_1-C_4)$alkyl and —$(C_1-C_4)$alkylene-O—$(C_1-C_4)$alkyl is optionally substituted with 1 to 4 substituents independently selected from the group consisting of —F, —Cl, —Br, —OH, and —$NR_5R_6$;

ring A is —$(C_6-C_{10})$aryl or —$(C_5-C_{10})$heteroaryl;

each $R_A$ is independently H, —$(C_1-C_4)$alkyl, —$(C_3-C_8)$cycloalkyl, —$(C_5-C_7)$ heterocycloalkyl, —$(C_6-C_{10})$aryl, or —$(C_5-C_{10})$heteroaryl, wherein each —$(C_1-C_4)$alkyl, —$(C_3-C_8)$cycloalkyl, —$(C_5-C_7)$ heterocycloalkyl, —$(C_6-C_{10})$aryl, and —$(C_5-C_{10})$heteroaryl is optionally and independently substituted with 1 to 4 substituents; or any two $R_A$ together with the atoms to which each is bound form a fused aryl or heteroaryl group;

$R_1$ is —$(CH_2)_n$-L, in which n is 0-3 and L is H, —C(O)O—$R_9$, —CO—$N(R_9R_{10})$, —$NR_9R_{10}$, —$N(R_{10})C(O)OR_9$, or —$N(R_{10})C(O)R_9$;

$R_2$ is H, D, halogen, or —$(C_1-C_4)$alkyl;

$R_4$, $R_5$, and $R_6$ are each independently selected from the group consisting of: H, —$(C_1-C_4)$alkyl, —$(C_3-C_8)$cycloalkyl, —$(C_5-C_7)$heterocycloalkyl, —$(C_6-C_{10})$aryl, and —$(C_5-C_7)$heteroaryl, wherein each —$(C_1-C_4)$alkyl, —$(C_3-C_8)$cycloalkyl, —$(C_5-C_7)$heterocycloalkyl, —$(C_6-C_{10})$aryl, and —$(C_5-C_7)$heteroaryl is optionally and independently substituted with 1 to 4 substituents;

$R_9$ is selected from the group consisting of: H, —$(C_1-C_6)$alkyl, —$(C_0-C_6)$alkylene-cycloalkyl, —$(C_0-C_6)$alkylene-heterocycloalkyl, —$(C_0-C_6)$alkylene-aryl, —$(C_0-C_6)$alkylene-heteroaryl, and —$N=CR_{11}R_{12}$, wherein each —$(C_1-C_6)$alkyl and —$(C_0-C_6)$alkylene- is optionally and independently substituted with 1 to 4 substituents and each -cycloalkyl, -heterocycloalkyl, -aryl, and -heteroaryl is optionally and independently substituted with 1 to 4 substituents;

$R_{10}$ is selected from the group consisting of: H, —$(C_1-C_6)$alkyl, —$(C_0-C_6)$alkylene-cycloalkyl, —$(C_0-C_6)$alkylene-heterocycloalkyl, —$(C_0-C_6)$alkylene-aryl; and —$(C_0-C_6)$alkylene-heteroaryl, wherein each —$(C_1-C_6)$alkyl and —$(C_0-C_6)$alkylene- is optionally and independently substituted with 1 to 4 substituents and each -cycloalkyl, -heterocycloalkyl, -aryl, and -heteroaryl is optionally and independently substituted with 1 to 4 substituents;

$R_9$ and $R_{10}$ are taken together with the nitrogen atom to which they are bound form a 4-10-membered ring;

$R_{11}$ is H, —$(C_1-C_4)$alkyl, or —$(C_1-C_4)$alkylene-O—$(C_1-C_4)$alkyl, wherein each —$(C_1-C_4)$alkyl, and —$(C_1-C_4)$alkylene-O—$(C_1-C_4)$alkyl is optionally and independently substituted with 1 to 3 substituents selected from the group consisting of: —F, —Cl, —Br, and —OH;

$R_{12}$ is H, —$(C_1-C_4)$alkyl, —$(C_3-C_8)$cycloalkyl, —$(C_5-C_7)$heterocycloalkyl, —$(C_6-C_{10})$aryl, or —$(C_5-C_7)$heteroaryl, wherein each —$(C_1-C_4)$alkyl, —$(C_3-C_8)$cycloalkyl, —$(C_5-C_7)$heterocycloalkyl, —$(C_6-C_{10})$aryl, and —$(C_5-C_7)$heteroaryl is optionally and independently substituted with 1 to 4 substituents; and m is 0, 1, 2, or 3.

In a particular embodiment, the condition associated with hyperinsulinaemia is an insulinoma.

In a specific embodiment, the condition associated with hyperinsulinaemia is congenital hyperinsulinism.

In a first aspect of the fifth embodiment or the particular or specific embodiment thereof: X is N.

In a second aspect of the fifth embodiment or the particular or specific embodiment thereof: $R_B$ is selected from the group consisting of: H, —$(C_1-C_4)$ alkyl, and —$(C_1-C_4)$ alkylene-O—$(C_1-C_4)$alkyl, and each —$(C_1-C_4)$ alkyl and —$(C_1-C_4)$alkylene-O—$(C_1-C_4)$alkyl is optionally substituted with 1 to 4 substituents independently selected from the group consisting of —F, —Cl, —Br, and —OH.

In a third aspect of the fifth embodiment or the particular or specific embodiment thereof: $R_B$ is methyl, ethyl, hydroxy methyl, methoxymethyl, or trifluoromethyl.

In a fourth aspect of the fifth embodiment or the particular or specific embodiment thereof: ring A is 5- or 6-membered aryl or heteroaryl.

In a fifth aspect of the fifth embodiment or the particular or specific embodiment thereof: ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In a sixth aspect of the fifth embodiment or the particular or specific embodiment thereof: ring A is phenyl or thienyl.

In a seventh aspect of the fifth embodiment or the particular or specific embodiment thereof: $R_A$ is independently H or —$(C_1-C_4)$alkyl, or any two $R_A$ together with the atoms to which each is attached, can form a fused aryl.

In an eighth aspect of the fifth embodiment or the particular or specific embodiment thereof: m is 2, and at least one occurrence of $R_A$ is methyl.

In a ninth aspect of the fifth embodiment or the particular or specific embodiment thereof: m is 2 and each $R_A$ is methyl.

In a tenth aspect of the fifth embodiment or the particular or specific embodiment thereof: L is —CO—$N(R_9R_{10})$, $R_9$ is —$(C_0-C_6)$alkylene-heterocycloalkyl, —$(C_0-C_6)$ alkylene-aryl, or —$(C_0-C_6)$alkylene-heteroaryl, optionally and independently substituted with 1 to 4 $(C_1-C_4)$alkyl, and $R_{10}$ is H or —$(C_1-C_6)$alkyl.

In an eleventh aspect of the fifth embodiment or the particular or specific embodiment thereof: L is —COO—$R_9$, and $R_9$ is independently selected from the group consisting of —$(C_1-C_6)$alkyl, —$(C_0-C_6)$alkylene-heterocycloalkyl, —$(C_0-C_6)$alkylene-aryl, and —$(C_0-C_6)$alkylene-heteroaryl and each —$(C_1-C_6)$alkyl, -heterocycloalkyl, -aryl, and -heteroaryl is optionally substituted with 1 to 4 substituents independently selected from the group consisting of —F, —Cl, —Br, and —$(C_1-C_6)$alkyl.

In a twelfth aspect of the fifth embodiment or the particular or specific embodiment thereof: L is —COO—$R_9$, and $R_9$ is selected from the group consisting of: methyl, ethyl, propyl, i-propyl, butyl, sec-butyl, t-butyl, and trifluoromethyl.

In a thirteenth aspect of the fifth embodiment or the particular or specific embodiment thereof: $R_2$ is H or —$(C_1-C_4)$alkyl.

In a sixth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by Structural Formula VI:

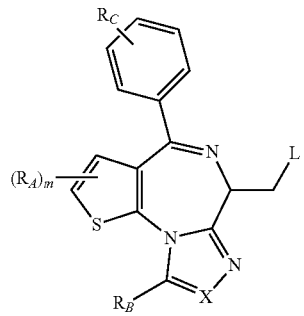

(VI)

or a pharmaceutically acceptable salt thereof, wherein:

X is N or $CR_3$;

$R_3$ is selected from the group consisting of: H, —$(C_1$-$C_4)$ alkyl, —$(C_3$-$C_8)$cycloalkyl, —$(C_5$-$C_7)$heterocycloalkyl, —$(C_6$-$C_{10})$aryl, and —$(C_5$-$C_{10})$heteroaryl, wherein each —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_{10})$heteroaryl is optionally and independently substituted with 1 to 4 substituents;

$R_B$ is H, —$(C_1$-$C_4)$alkyl, —$(C_1$-$C_4)$alkylene-O—$(C_1$-$C_4)$ alkyl, or —COO—$R_4$, wherein each —$(C_1$-$C_4)$alkyl and —$(C_1$-$C_4)$alkylene-O—$(C_1$-$C_4)$alkyl is optionally substituted with 1 to 4 substituents independently selected from the group consisting of —F, —Cl, —Br, —OH, and —$NR_5R_6$;

each $R_A$ is independently H, —$(C_1$-$C_4)$alkyl, —$(C_3$-$C_8)$cycloalkyl, —$(C_5$-$C_7)$ heterocycloalkyl, —$(C_6$-$C_{10})$aryl, or —$(C_5$-$C_{10})$heteroaryl, wherein each —$(C_1$-$C_4)$alkyl, —$(C_3$-$C_8)$cycloalkyl, —$(C_5$-$C_7)$ heterocycloalkyl, —$(C_6$-$C_{10})$aryl, and —$(C_5$-$C_{10})$heteroaryl is optionally and independently substituted with 1 to 4 substituents; or any two $R_A$ together with the atoms to which each is bound form a fused aryl or heteroaryl group;

L is H, —C(O)O—$R_9$, —CO—N($R_9R_{10}$), —$NR_9R_{10}$, —N($R_{10}$)C(O)O$R_9$, or —N($R_{10}$)C(O)$R_9$;

$R_C$ is selected from the group consisting of: —F, —Cl, —Br, —OH, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, —C(O)-(fluoro-substituted-$(C_1$-$C_4)$alkyl), —S(O)$_o$—$(C_1$-$C_4)$alkyl, —$NR_7R_8$ and CN;

$R_4$, $R_5$, $R_6$, $R_7$ and $R_8$ are each independently selected from the group consisting of: H, —$(C_1$-$C_4)$alkyl, —$(C_3$-$C_8)$ cycloalkyl, —$(C_5$-$C_7)$heterocycloalkyl, —$(C_6$-$C_{10})$aryl, and —$(C_5$-$C_7)$heteroaryl, wherein each —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$heteroaryl is optionally and independently substituted with 1 to 4 substituents;

$R_9$ is selected from the group consisting of: H, —$(C_1$-$C_6)$ alkyl, —$(C_0$-$C_6)$alkylene-cycloalkyl, —$(C_0$-$C_6)$alkylene-heterocycloalkyl, —$(C_0$-$C_6)$alkylene-aryl, —$(C_0$-$C_6)$alkylene-heteroaryl, and —N=$CR_{11}R_{12}$, wherein each —$(C_1$-$C_6)$alkyl and —$(C_0$-$C_6)$alkylene- is optionally and independently substituted with 1 to 4 substituents and each -cycloalkyl, -heterocycloalkyl, -aryl, and -heteroaryl is optionally and independently substituted with 1 to 4 substituents;

$R_{10}$ is selected from the group consisting of: H, —$(C_1$-$C_6)$alkyl, —$(C_0$-$C_6)$alkylene-cycloalkyl, —$(C_0$-$C_6)$alkylene-heterocycloalkyl, —$(C_0$-$C_6)$alkylene-aryl; and —$(C_0$-$C_6)$alkylene-heteroaryl, wherein each —$(C_1$-$C_6)$alkyl and —$(C_0$-$C_6)$alkylene- is optionally and independently substituted with 1 to 4 substituents and each -cycloalkyl, -heterocycloalkyl, -aryl, and -heteroaryl is optionally and independently substituted with 1 to 4 substituents;

$R_9$ and $R_{10}$ are taken together with the nitrogen atom to which they are bound form a 4-10-membered ring;

$R_{11}$ is H, —$(C_1$-$C_4)$alkyl, or —$(C_1$-$C_4)$alkylene-O—$(C_1$-$C_4)$alkyl, wherein each —$(C_1$-$C_4)$alkyl, and —$(C_1$-$C_4)$alkylene-O—$(C_1$-$C_4)$alkyl is optionally and independently substituted with 1 to 3 substituents selected from the group consisting of: —F, —Cl, —Br, and —OH;

$R_{12}$ is H, —$(C_1$-$C_4)$alkyl, —$(C_3$-$C_8)$cycloalkyl, —$(C_5$-$C_7)$heterocycloalkyl, —$(C_6$-$C_{10})$aryl, or —$(C_5$-$C_7)$heteroaryl, wherein each —$(C_1$-$C_4)$alkyl, —$(C_3$-$C_8)$cycloalkyl, —$(C_5$-$C_7)$heterocycloalkyl, —$(C_6$-$C_{10})$aryl, and —$(C_5$-$C_7)$ heteroaryl is optionally and independently substituted with 1 to 4 substituents;

m is 0, 1, 2, or 3; and o is 1 or 2.

In a particular embodiment, the condition associated with hyperinsulinaemia is an insulinoma.

In a specific embodiment, the condition associated with hyperinsulinaemia is congenital hyperinsulinism.

In a first aspect of the sixth embodiment or the particular or specific embodiment thereof: X is N.

In a second aspect of the sixth embodiment or the particular or specific embodiment thereof: $R_B$ is selected from the group consisting of: H, —$(C_1$-$C_4)$ alkyl, and —$(C_1$-$C_4)$ alkylene-O—$(C_1$-$C_4)$alkyl, and each —$(C_1$-$C_4)$ alkyl and —$(C_1$-$C_4)$alkylene-O—$(C_1$-$C_4)$alkyl is optionally substituted with 1 to 4 substituents independently selected from the group consisting of —F, —Cl, —Br, and —OH.

In a third aspect of the sixth embodiment or the particular or specific embodiment thereof: $R_B$ is methyl, ethyl, hydroxy methyl, methoxymethyl, or trifluoromethyl.

In a fourth aspect of the sixth embodiment or the particular or specific embodiment thereof: each $R_A$ is independently H or —$(C_1$-$C_4)$alkyl, or any two $R_A$ together with the atoms to which each is attached, can form a fused aryl.

In a fifth aspect of the sixth embodiment or the particular or specific embodiment thereof: m is 1 or 2, and at least one occurrence of $R_A$ is methyl.

In a sixth aspect of the sixth embodiment or the particular or specific embodiment thereof: m is 2 and each $R_A$ is methyl.

In a seventh aspect of the sixth embodiment or the particular or specific embodiment thereof: L is —CO—N ($R_9R_{10}$), $R_9$ is —$(C_0$-$C_6)$alkylene-heterocycloalkyl, —$(C_0$-$C_6)$ alkylene-aryl, or —$(C_0$-$C_6)$alkylene-heteroaryl and each -heterocycloalkyl, -aryl, and -heteroaryl is optionally and independently substituted with 1 to 4 $(C_1$-$C_4)$alkyl, and $R_{10}$ is H or —$(C_1$-$C_6)$alkyl.

In an eighth aspect of the sixth embodiment or the particular or specific embodiment thereof: L is —COO—$R_9$, and $R_9$ is independently selected from the group consisting of —$(C_1$-$C_6)$alkyl, —$(C_0$-$C_6)$alkylene -heterocycloalkyl, —$(C_0$-$C_6)$alkylene-aryl, and —$(C_0$-$C_6)$alkylene-heteroaryl and each —$(C_1$-$C_6)$alkyl, -heterocycloalkyl, -aryl, and -heteroaryl is optionally substituted with 1 to 4 substituents independently selected from the group consisting of —F, —Cl, —Br, and —$(C_1$-$C_6)$alkyl.

In a ninth aspect of the sixth embodiment or the particular or specific embodiment thereof: L is —COO—$R_9$, and $R_9$ is selected from the group consisting of: methyl, ethyl, propyl, i-propyl, butyl, sec-butyl, t-butyl, and trifluoromethyl.

In a tenth aspect of the sixth embodiment or the particular or specific embodiment thereof: $R_C$ is selected from the group consisting of: —F, —Cl, —Br, —OH, and —O—($C_1$-$C_4$)alkyl.

In a seventh embodiment, the present invention is directed to a method for treating a condition associated with hyperinsulinaemia (e.g., insulinoma, congential hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by invention provides a method for treating insulinoma or congenital hyperinsulinism (CHI) in a subject in need thereof using a compound represented following structural formula:

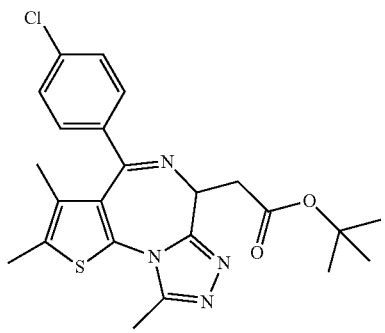 [SMILES: Cc1sc2c(c1C)C(c1ccc(Cl)cc1)=NC(CC(=O)OC(C)(C)C)c1nnc(C)n1-2]

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In first aspect of the seventh embodiment or the particular or specific embodiments thereof, the compound is represented following structural formula:

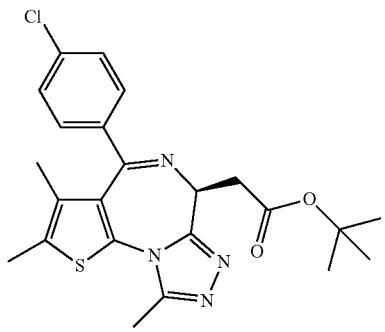 [SMILES: Cc1sc2c(c1C)C(c1ccc(Cl)cc1)=N[C@@H](CC(=O)OC(C)(C)C)c1nnc(C)n1-2]

or a pharmaceutically acceptable salt thereof.

In an eighth embodiment, the present invention is directed to a method for treating a condition associated with hyperinsulinaemia (e.g., insulinoma, congential hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by any one of the following structural formulas:

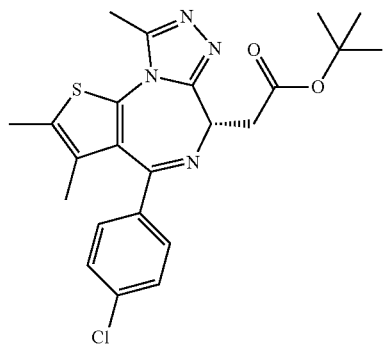
JQ1S

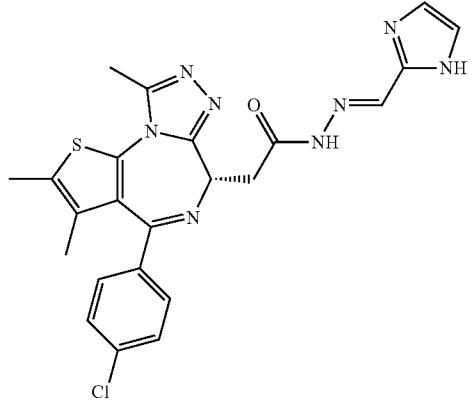
JQ6

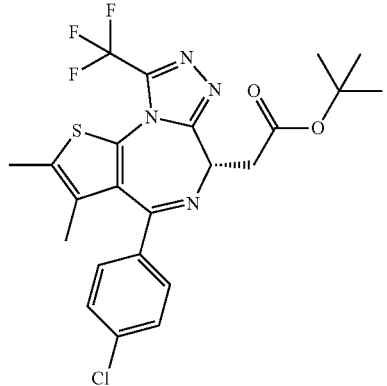
JQ11

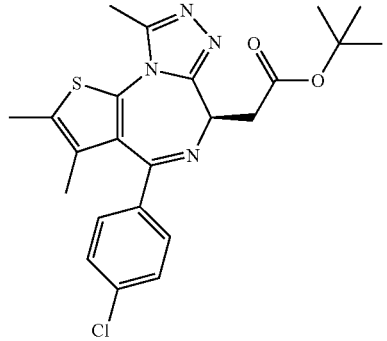
JQ1R

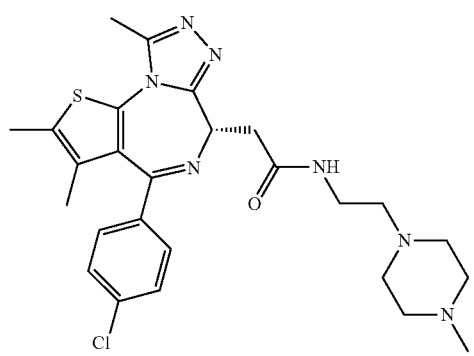
JQ13

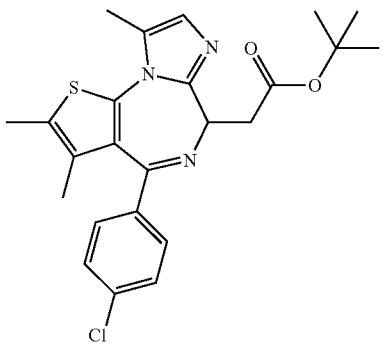
JQ24B

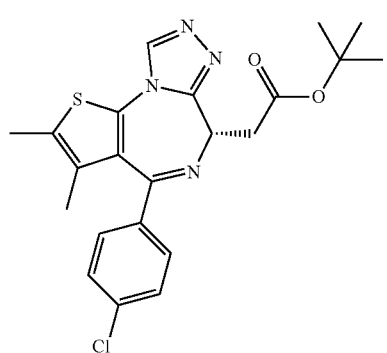
JQ21

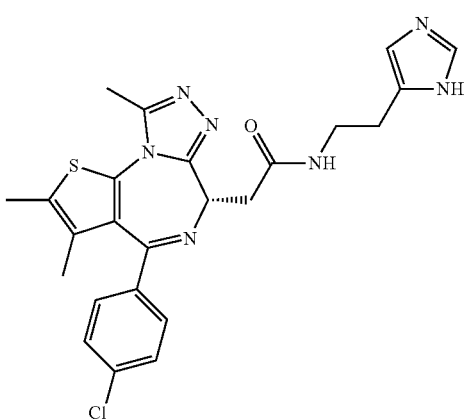
JQ8

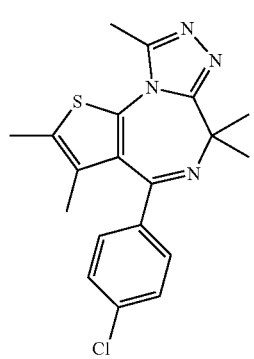
JQ20

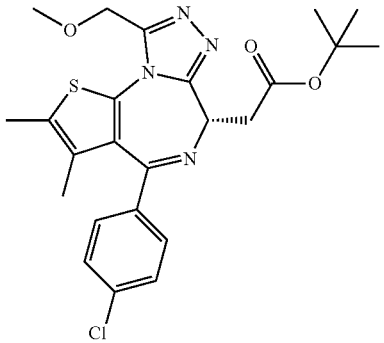
JQ18

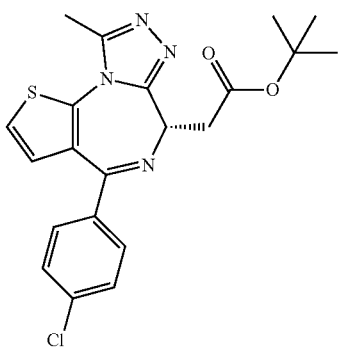
KS1

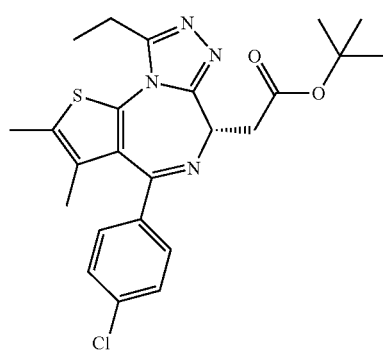
JQ19 or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In a ninth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by any one of the following structural formulas:

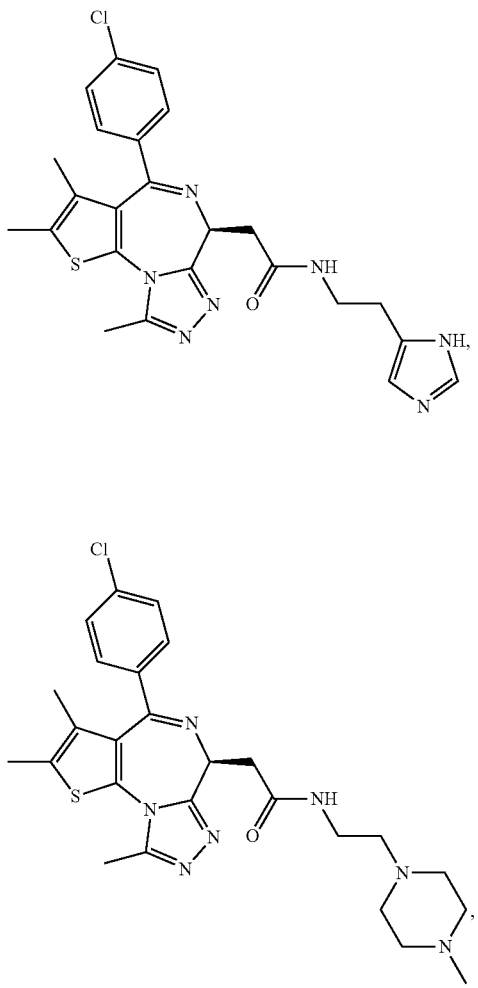

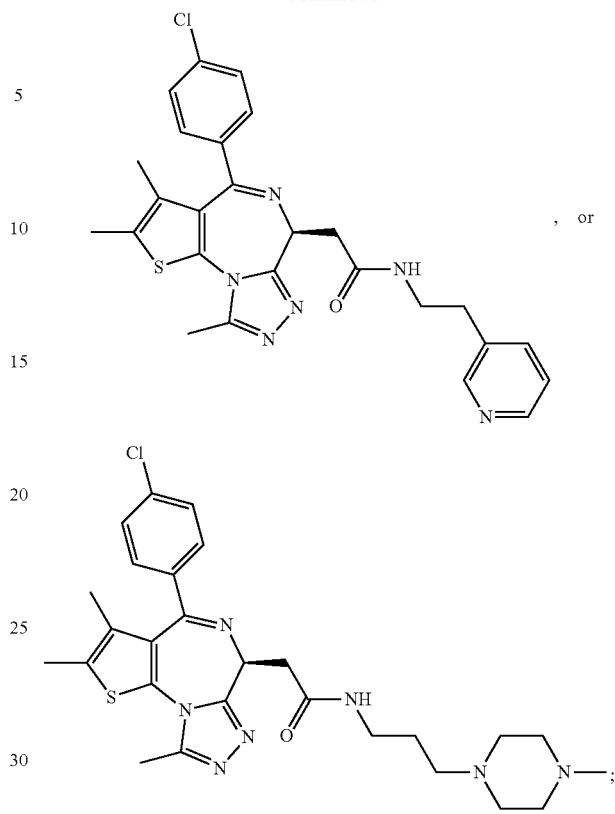

, or or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In a tenth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by any one of the following structural formulas:

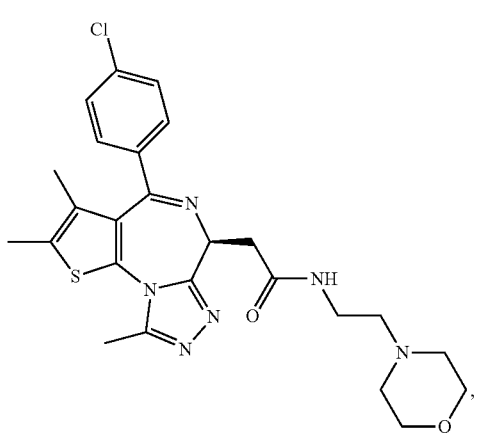

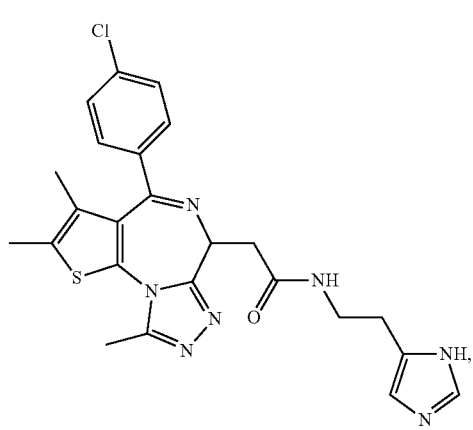

-continued

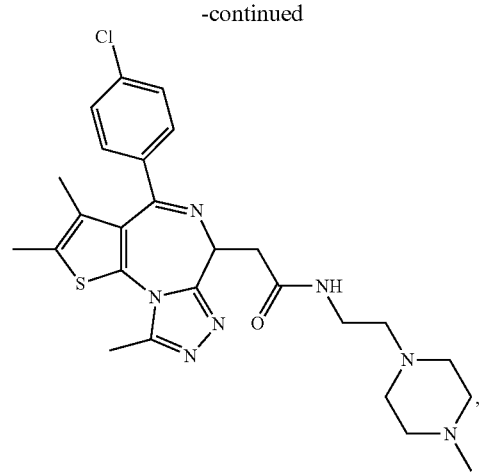

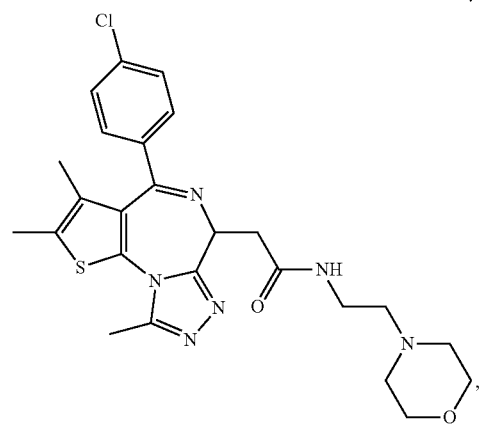

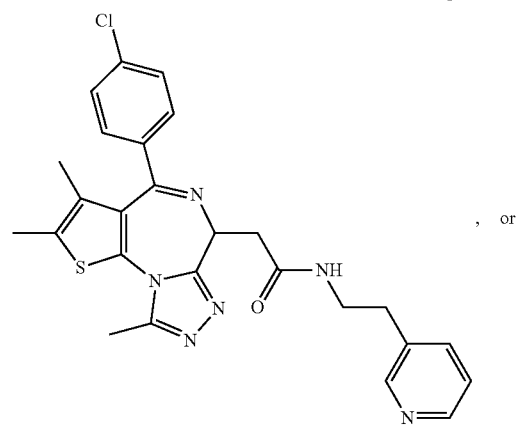

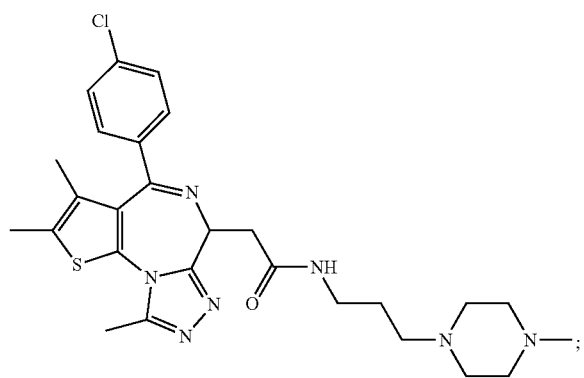

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In an eleventh embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by any one of the following structural formulas:

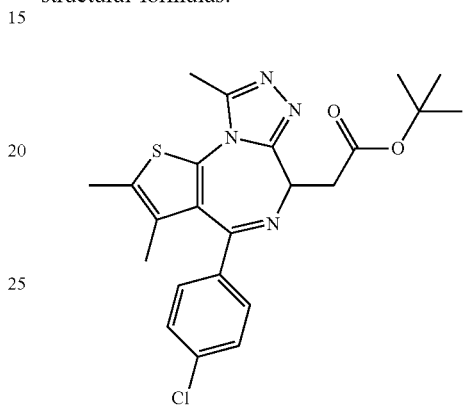

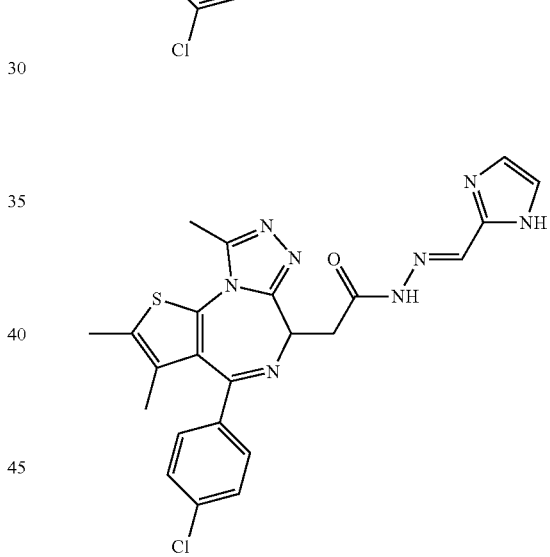

, or

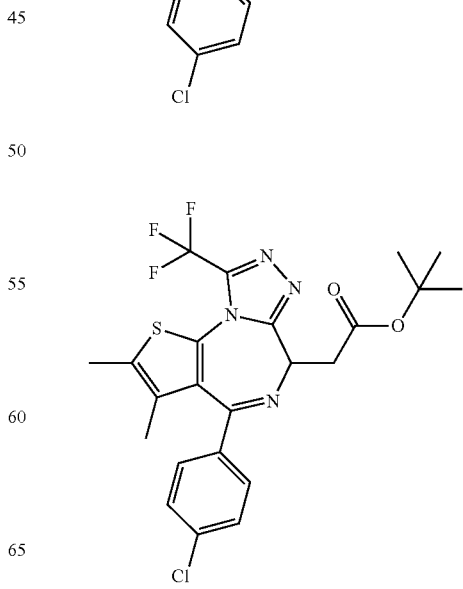

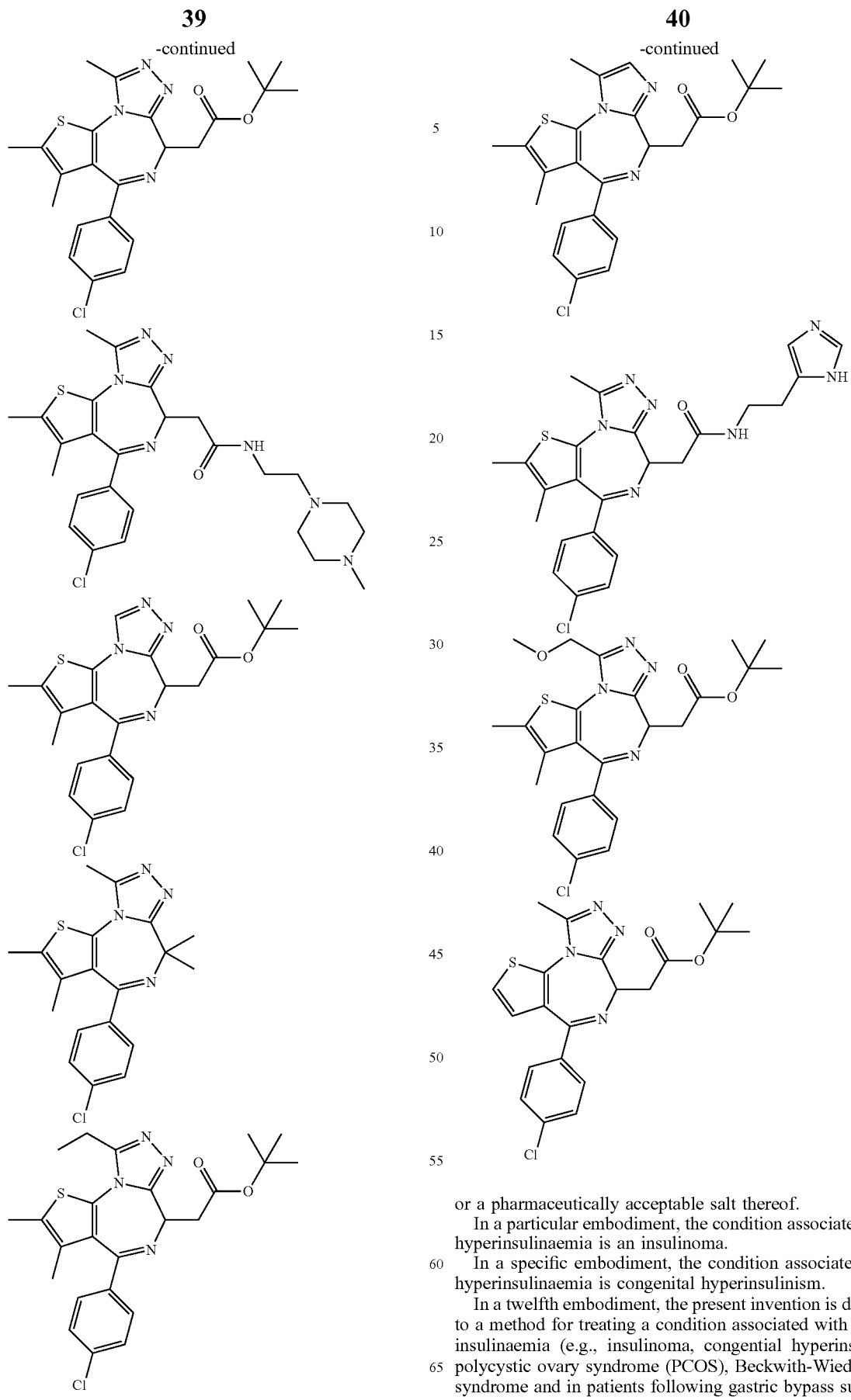

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In a twelfth embodiment, the present invention is directed to a method for treating a condition associated with hyperinsulinaemia (e.g., insulinoma, congenital hyperinsulinism, polycystic ovary syndrome (PCOS), Beckwith-Wiedemann syndrome and in patients following gastric bypass surgery) in a subject in need thereof, comprising administering to the subject an effective amount of a compound represented by represented by any one of the following structural formulas:

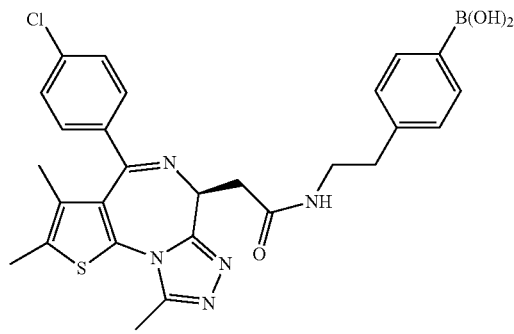

or

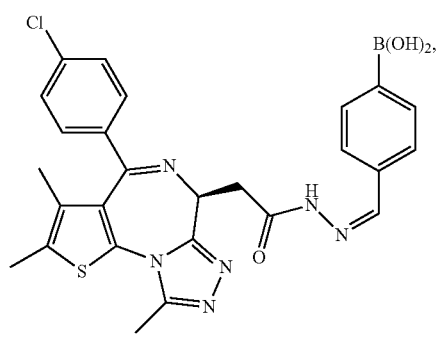

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In a thirteenth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by any one of the following structural formulas:

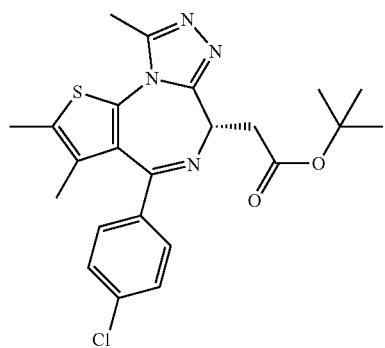

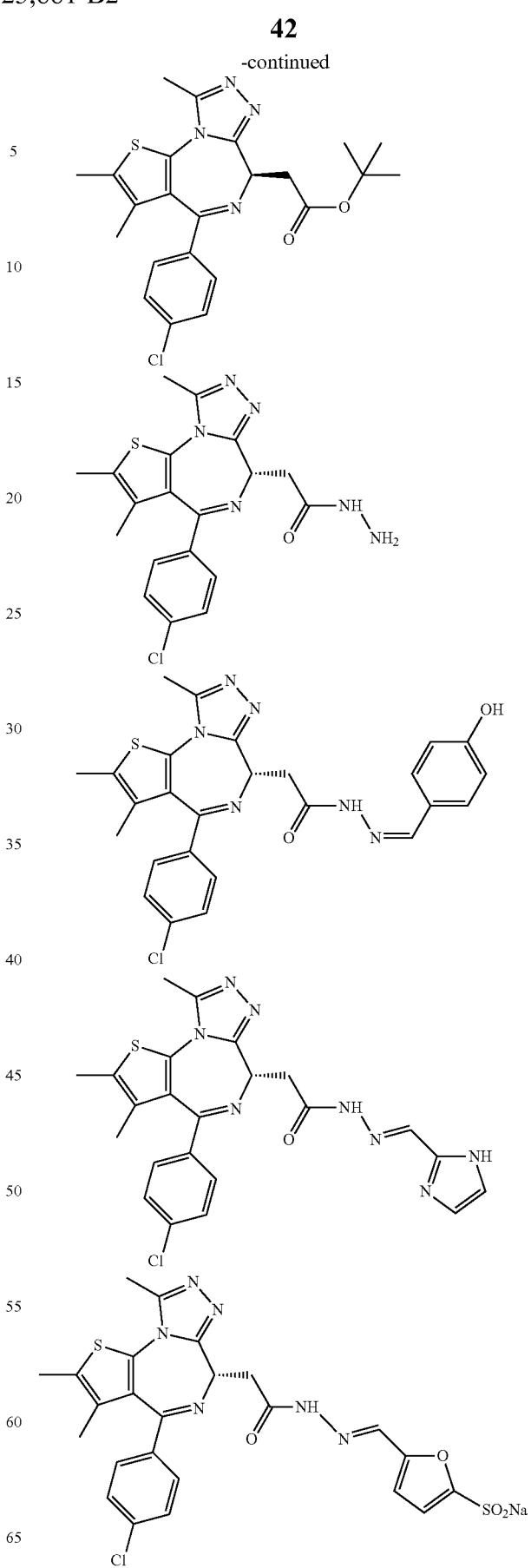

43
-continued
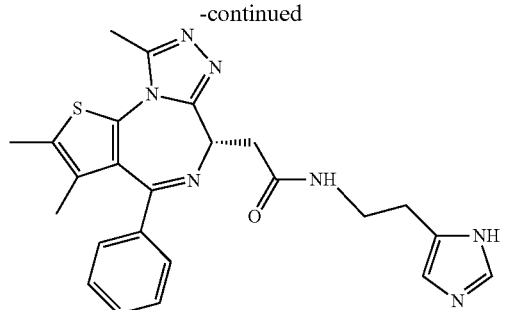
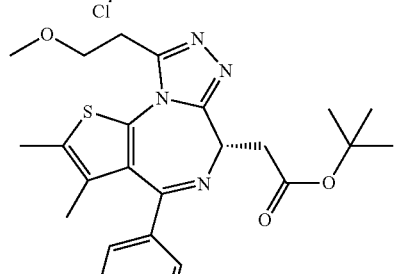
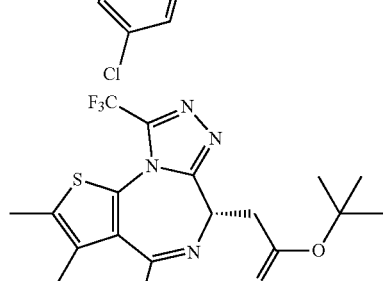
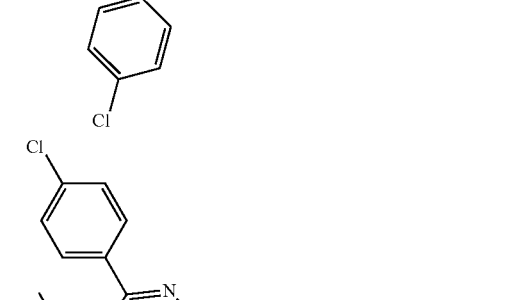
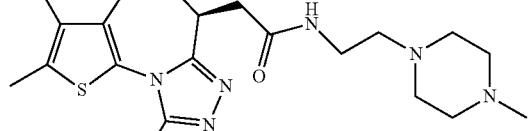
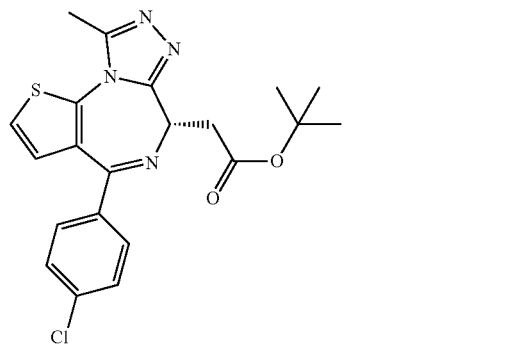
44
-continued
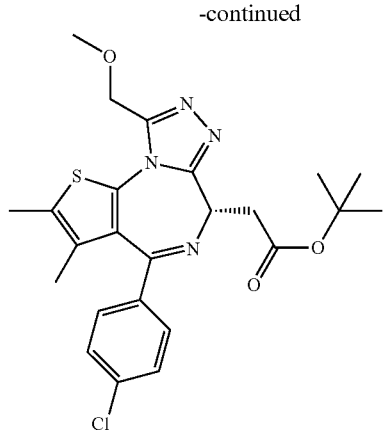
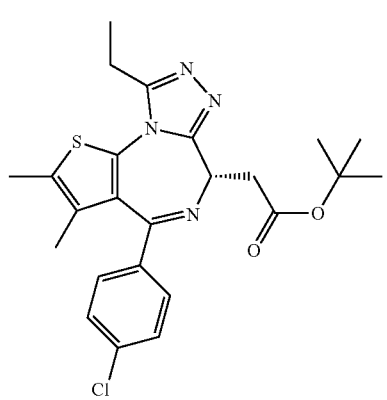
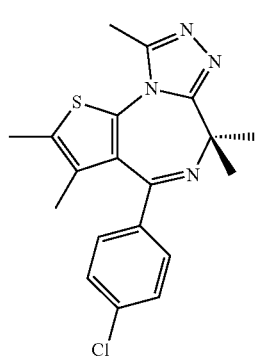
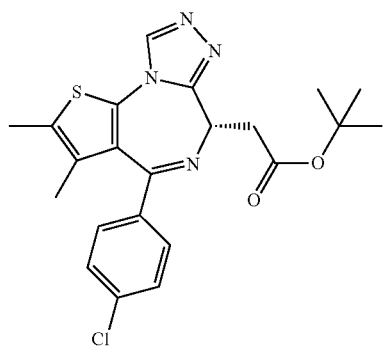

45
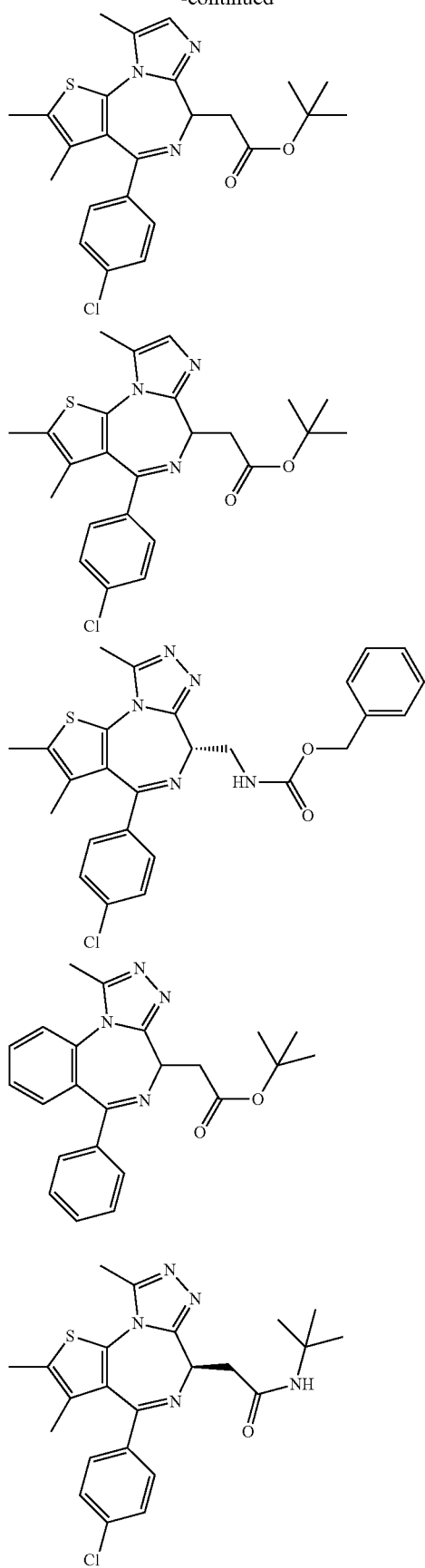
46
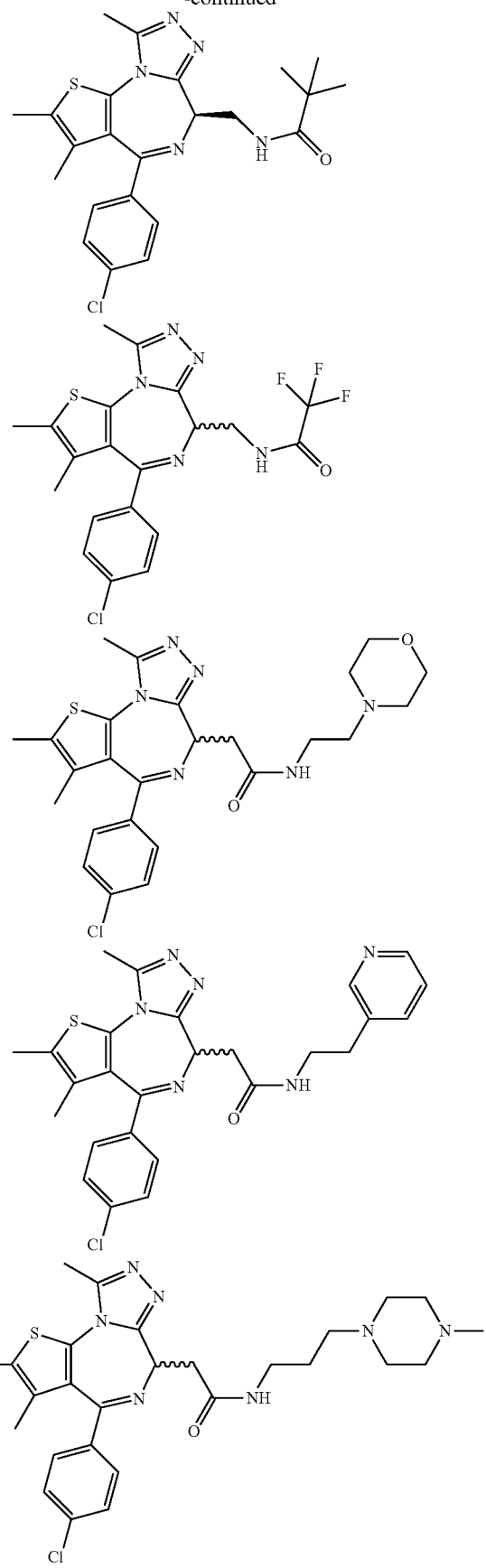

47

-continued

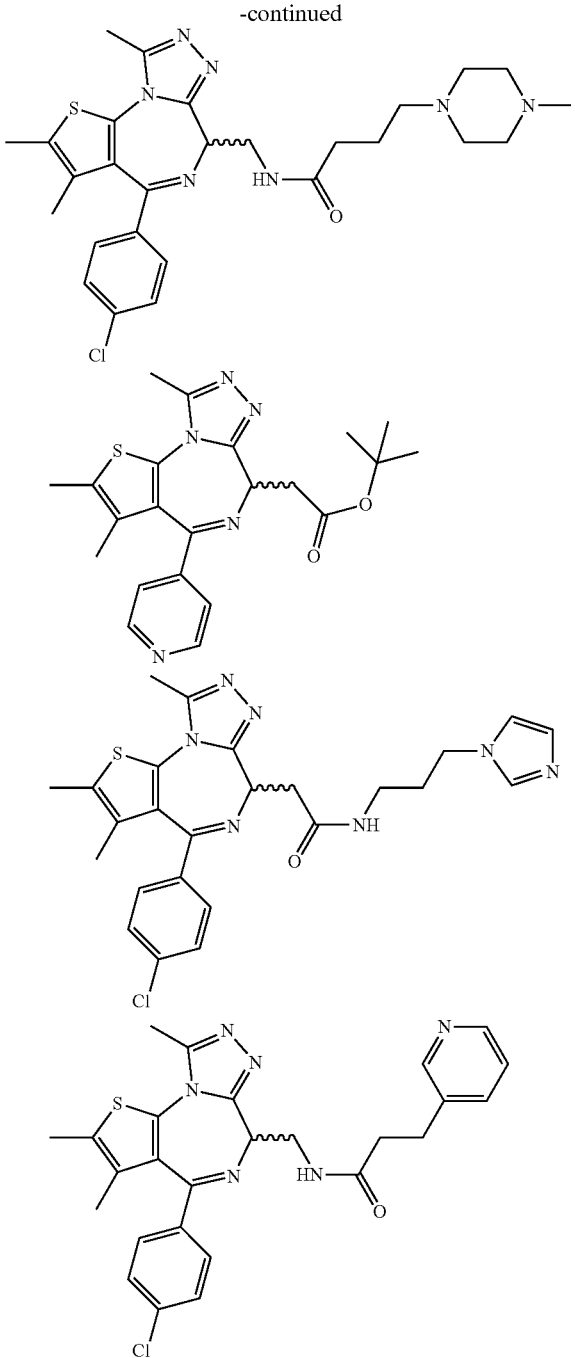

48

-continued

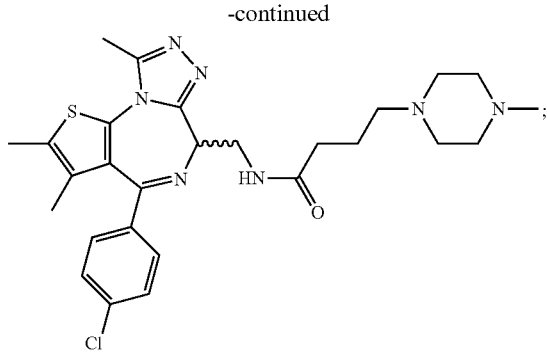

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In a fourteenth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by represented by any one of the following structural formulas:

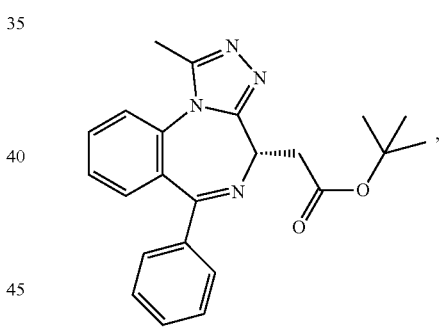

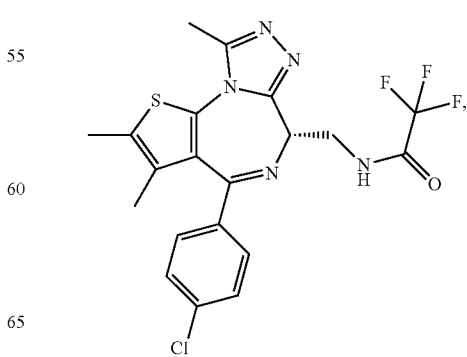

49
-continued
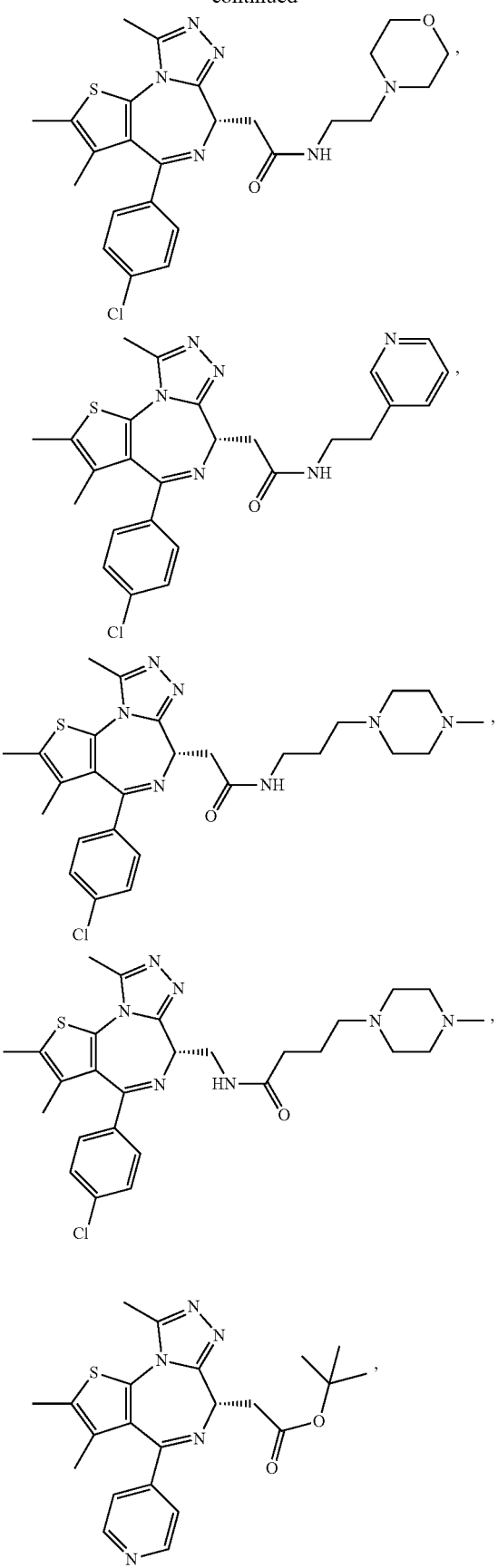
50
-continued
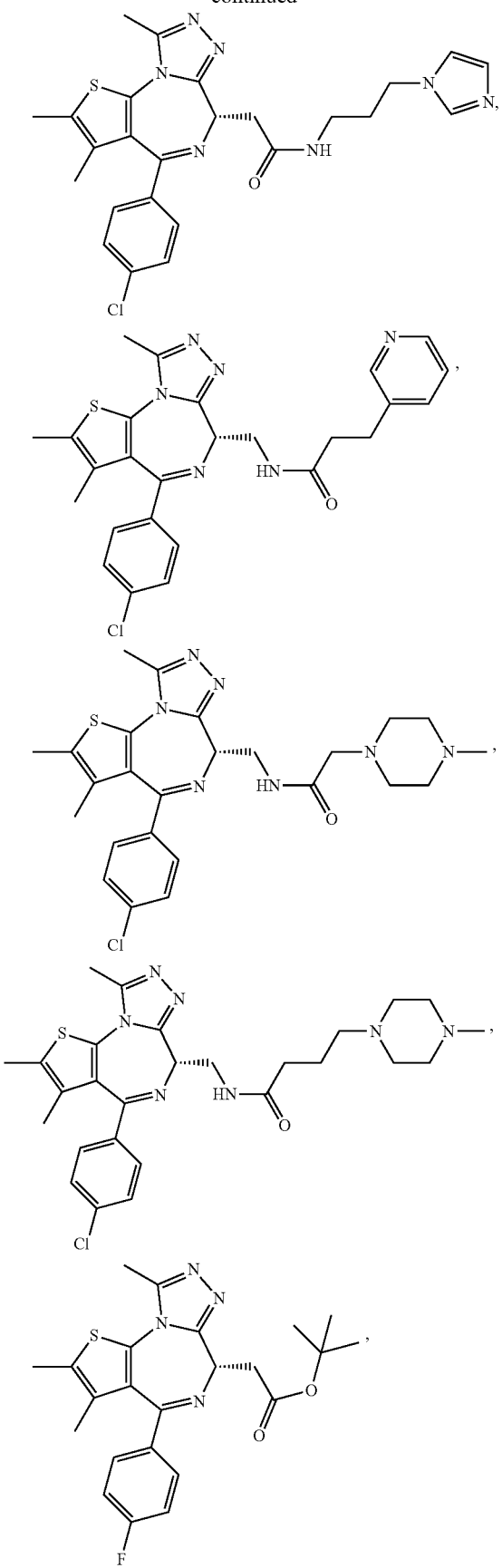

51
-continued
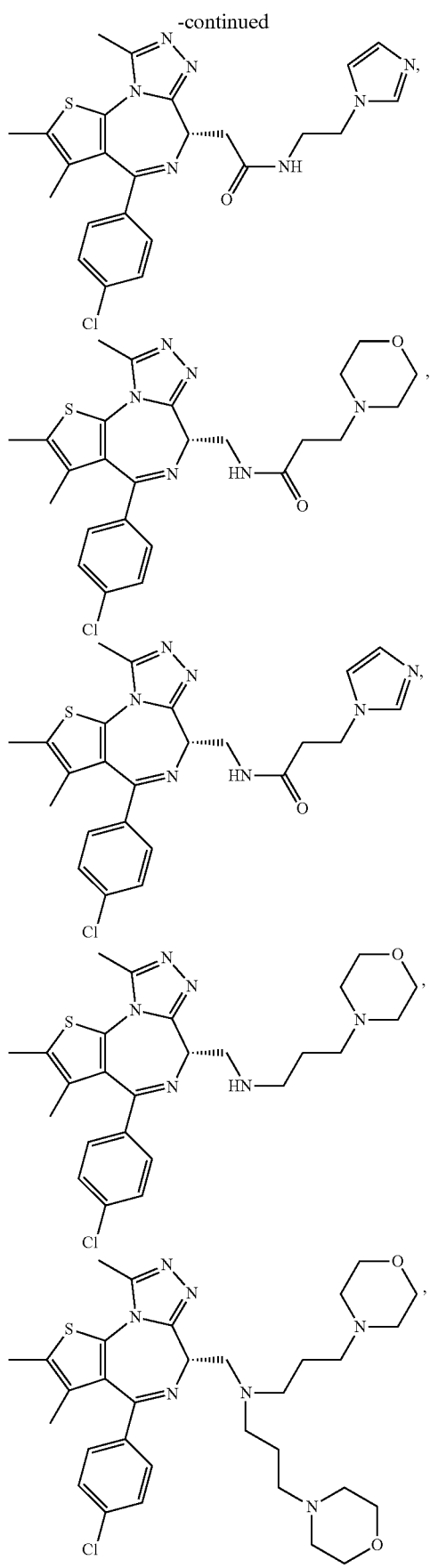
52
-continued
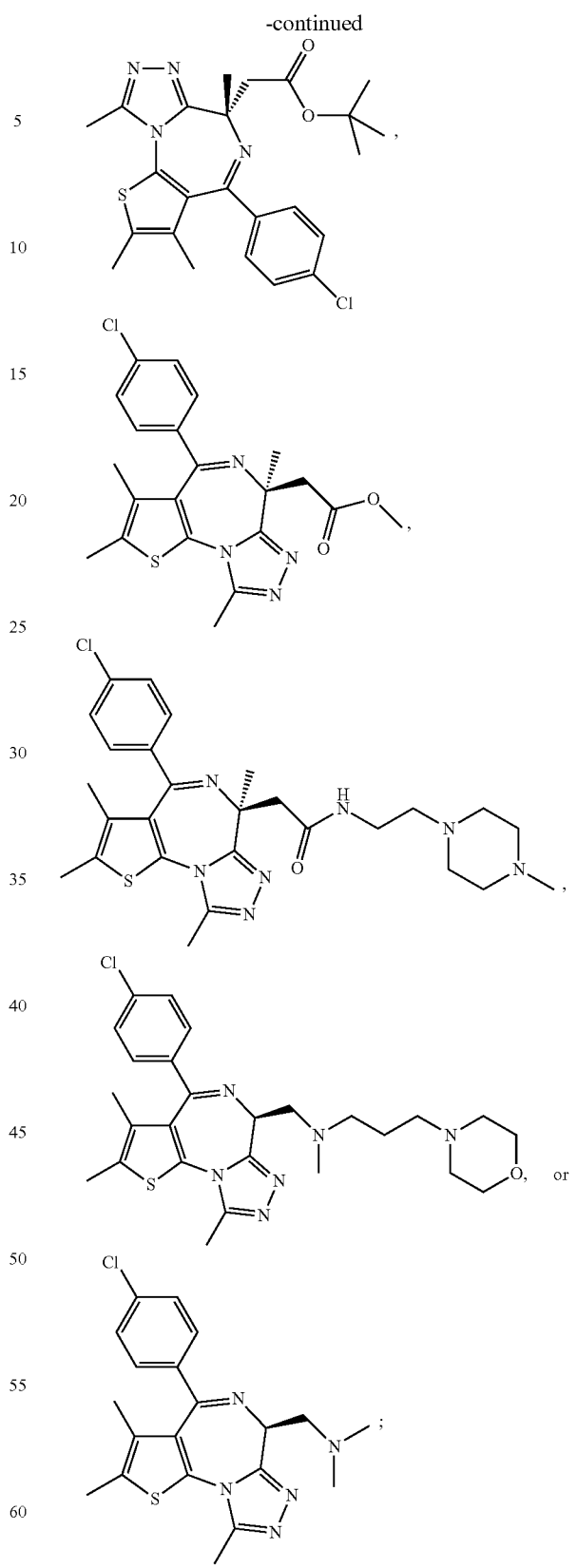
or a pharmaceutically acceptable salt thereof.
In a particular embodiment, the condition associated with hyperinsulinaemia is an insulinoma.

In a specific embodiment, the condition associated with hyperinsulinaemia is congenital hyperinsulinism.

In a fifteenth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by the structure:

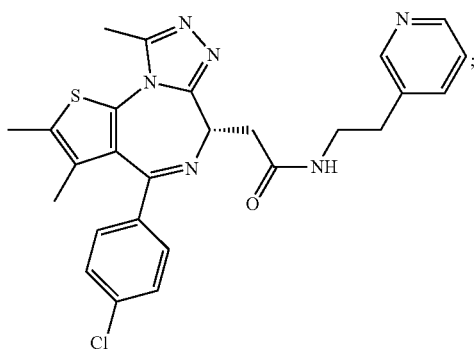 [SMILES: Cc1sc2c(c1C)C(c1ccc(Cl)cc1)=N[C@@H](CC(=O)NCCc1cccnc1)c1nnc(C)n1-2]

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In a sixteenth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by the structure:

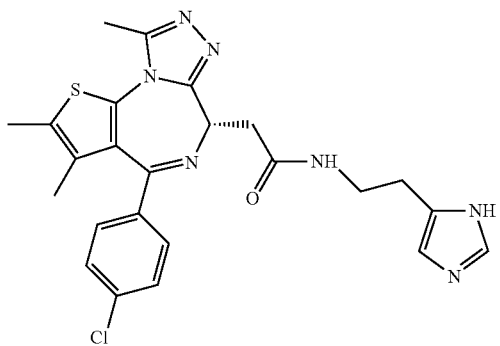 [SMILES: Cc1sc2c(c1C)C(c1ccc(Cl)cc1)=N[C@@H](CC(=O)NCCc1cnc[nH]1)c1nnc(C)n1-2]

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In a seventeenth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by the structure:

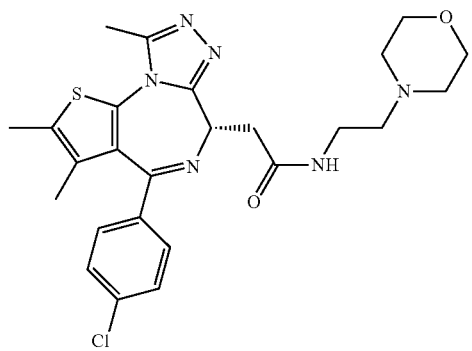 [SMILES: Cc1sc2c(c1C)C(c1ccc(Cl)cc1)=N[C@@H](CC(=O)NCCN1CCOCC1)c1nnc(C)n1-2]

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In an eighteenth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by Structural Formula (VI), (VII), or (VIII):

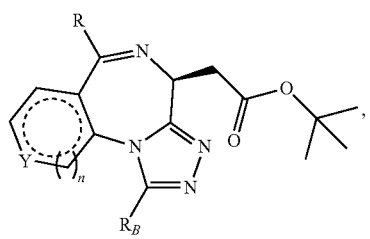

(VI)

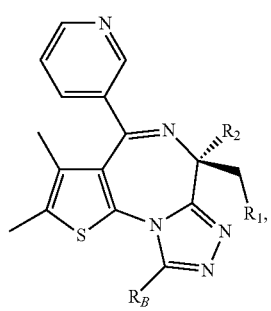

(VII)

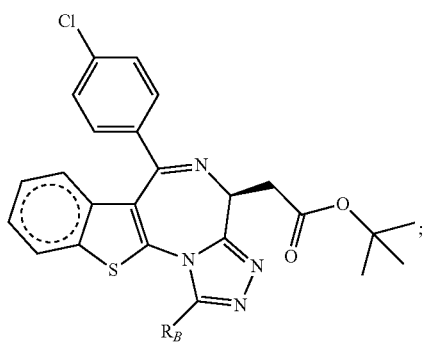

(VIII)

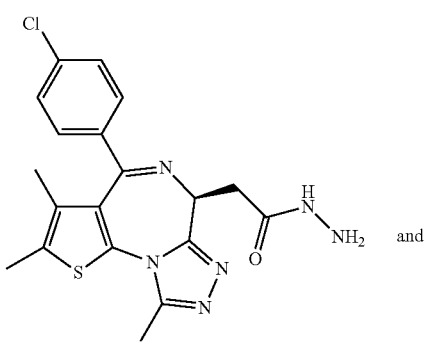

(3)

and in which R, $R_1$, and $R_2$ and $R_B$ have the same meaning as in Formula (I); Y is O, N, S, or $CR_3$, in which $R_3$ has the same meaning as in Formula (I); n is 0 or 1; and the dashed circle in Formula (VIII) indicates an aromatic or non-aromatic ring; or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In a nineteenth embodiment, the present invention is directed to a method for treating a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof, comprising administering to the subject an effective amount of a compound represented by the structure:

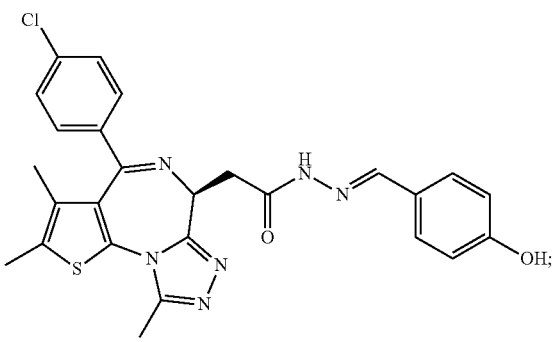

(4)

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

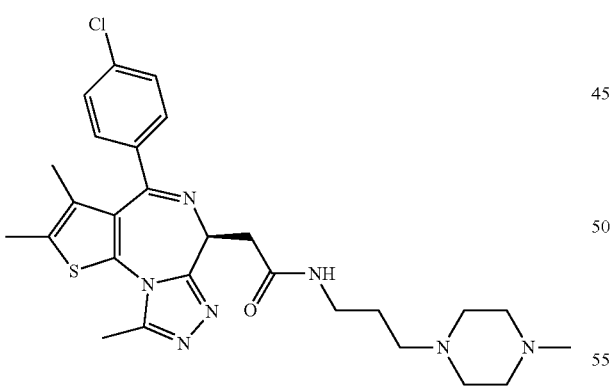

or a pharmaceutically acceptable salt thereof.

In a particular embodiment, the condition associated with hyperinsulinaemia is an insulinoma.

In a specific embodiment, the condition associated with hyperinsulinaemia is congenital hyperinsulinism.

In certain embodiments, the compound for use in the methods of the invention is a compound selected from the group consisting of:

Methods of Preparation of Compounds of the Present Invention

Compounds used in the methods of the invention can be prepared by a variety of methods. For instance, the chemical Examples provided herein below provide synthetic schemes for the preparation of the compound JQ1 (as the racemate) and the enantiomers (+)-JQ1 and (−)-JQ1 (see Schemes S1 and S2 in Examples). A variety of compounds of Formulas (I)-(IX) can be prepared by analogous methods with substitution of appropriate starting materials.

For example, starting from JQ1, the analogous amine can be prepared as shown in Scheme 1, below.

Scheme 1

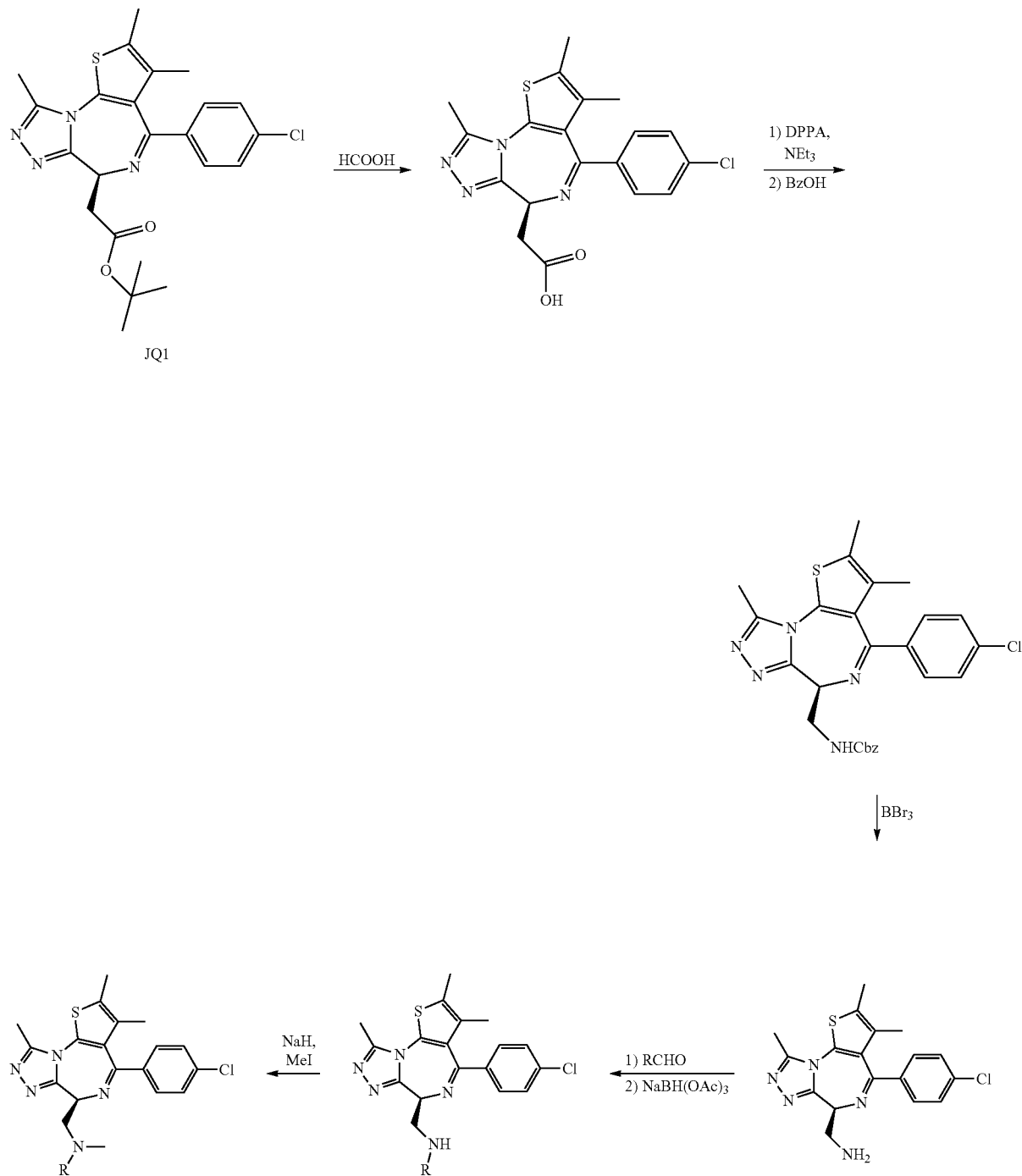

As shown in Scheme 1, hydrolysis of the t-butyl ester of JQ1 affords the carboxylic acid, which is treated with diphenylphosphoryl azide (DPPA) and subjected to Curtius rearrangement conditions to provide the Cbz-protected amine. The Cbz-protected amine is then deprotected to yield the amine. Subsequent elaboration of the amine group (e.g., by reductive amination) yields secondary amines, which can be further alkylated to provide tertiary amines.

Compounds used in the methods of the invention, e.g., of Formulas I-IX, in which the fused ring core is modified (e.g., substitution of Ring A in Formula I to a different aryl or heteroaryl ring) can be accomplished by using aminodiarylketones having appropriate functionality (e.g., in place of the aminodiarylketone S2 in Scheme S1, infra) to provide new compounds having a variety of fused ring cores and/or aryl groups with different substituents. Aminodiarylketones are commercially available or can be prepared by a variety of methods, some of which are known in the art.

Scheme 2 provides additional exemplary synthetic schemes for preparing further compounds of the invention Scheme 2

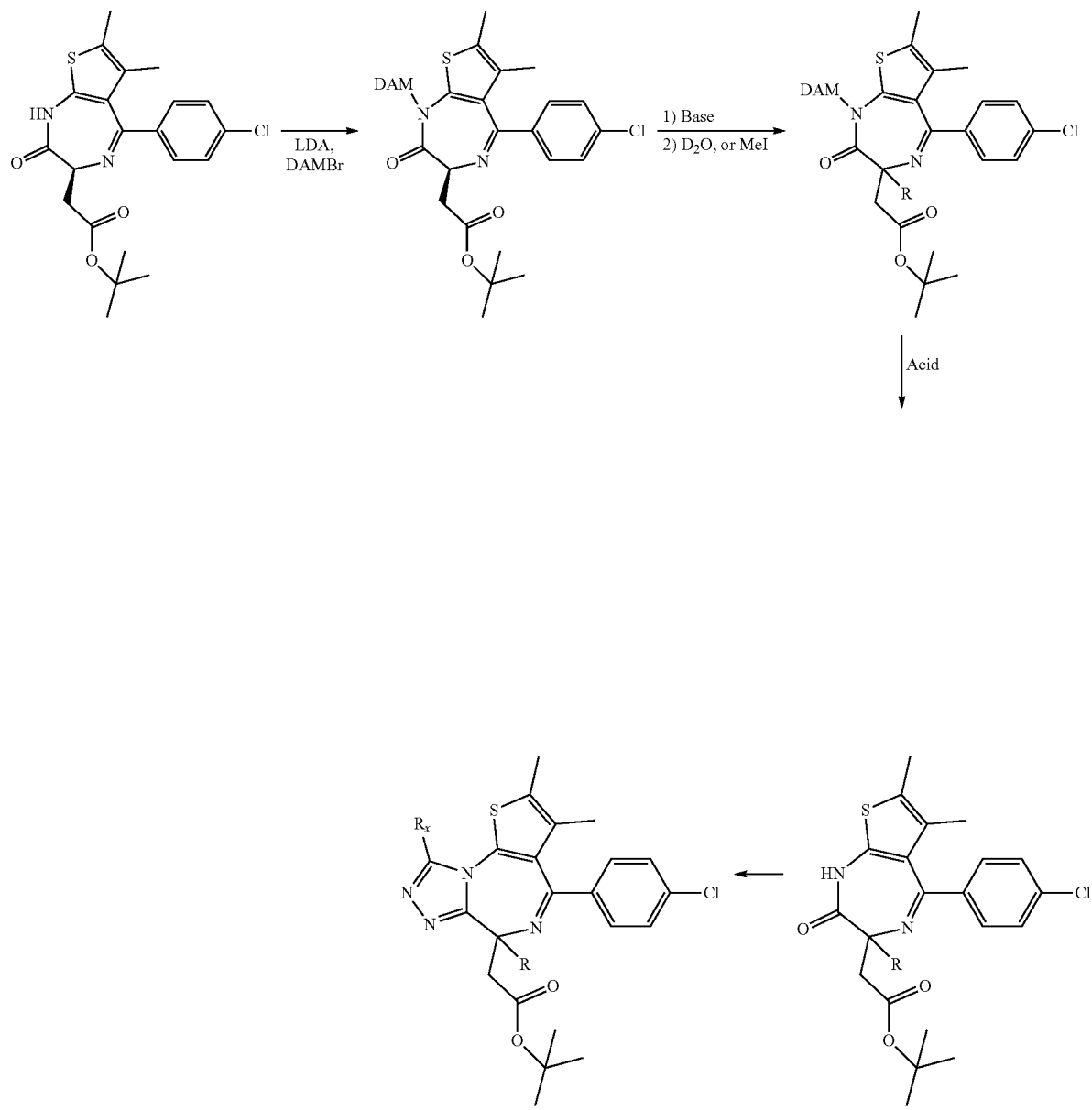

As shown in Scheme 2, a fused bicyclic precursor (see Scheme S1, infra, for synthesis of this compound) can be treated with dimethylaminomethylene bromide (DAM-Br) to obtain the DAM-protected intermediate shown in Scheme 2. Reaction of the DAM-protected intermediate with a hydrazine yields the tricyclic fused core. Substituent $R_x$ can be varied by selection of a suitable hydrazine.

Additional examples of compounds used in the methods of the invention (which can be prepared by the methods described herein) include:

Amides:

Amides can be prepared from the carboxylic acid or ester. Amidation of the carboxylic acid with an appropriate amine using standard amidation (e.g., coupling condition) conditions provides the amide product. In certain embodiments, the amide product formed is an amide substituted with a heterocycle connected by a two-carbon "linker". Exemplary amide structures include:

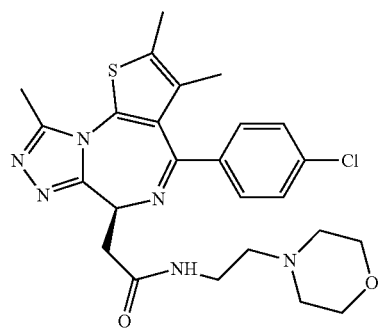

-continued
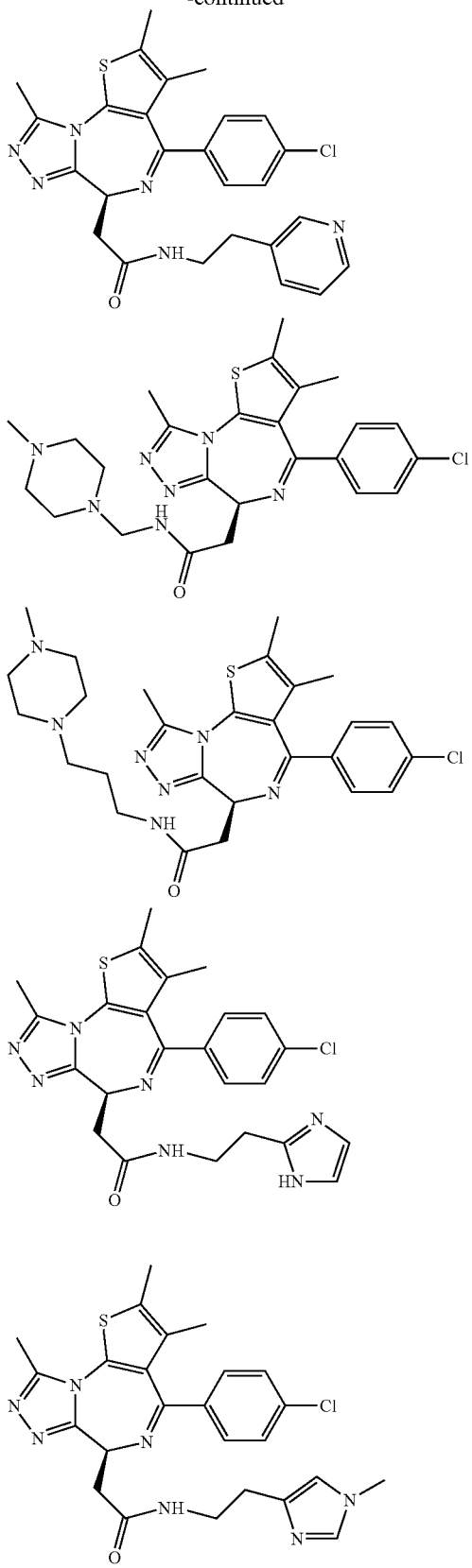
In other embodiments, the amide product formed is an amide substituted with a heterocycle connected by a three-carbon "linker". In certain embodiments, the amide product formed is an amide substituted with a heterocycle connected by a one-carbon "linker".
"Reverse Amides":
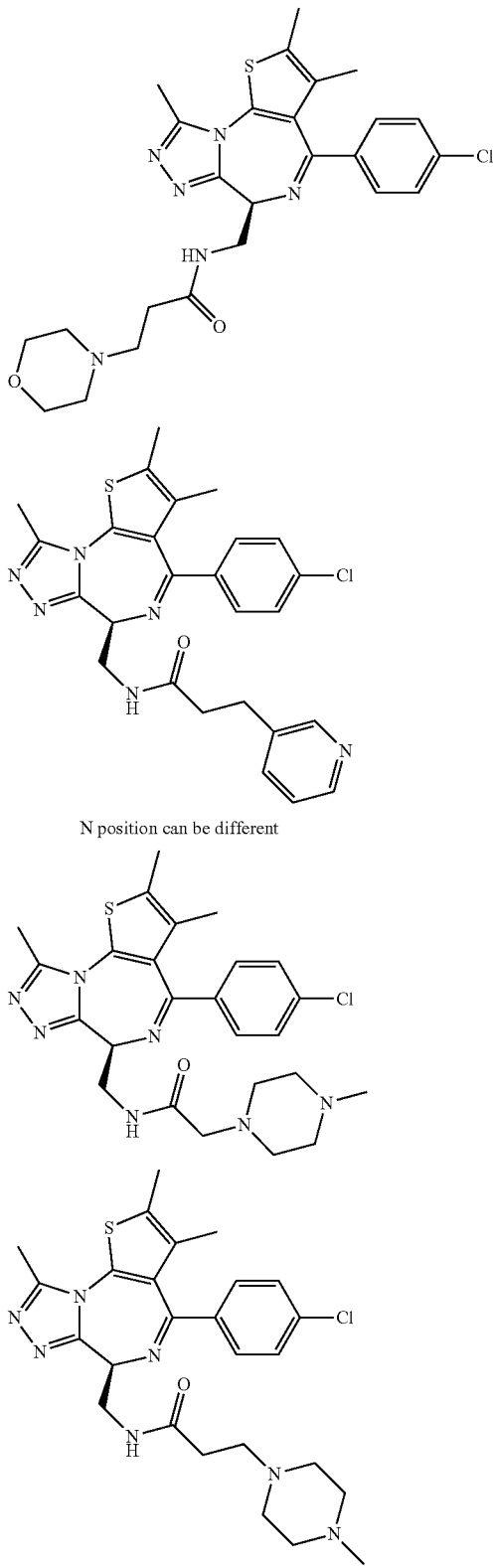
N position can be different 63
-continued
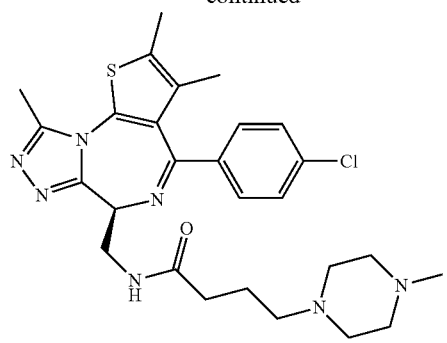
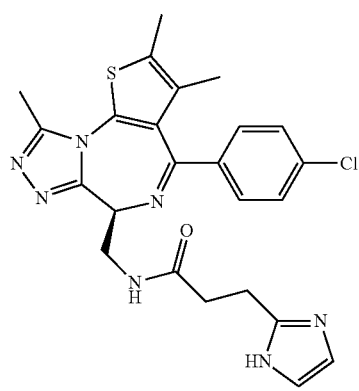 [SMILES: Cc1sc2c(c1C)C(c1ccc(Cl)cc1)=N[C@@H](CNCCCc1ncc[nH]1)c1nnc(C)n1-2]
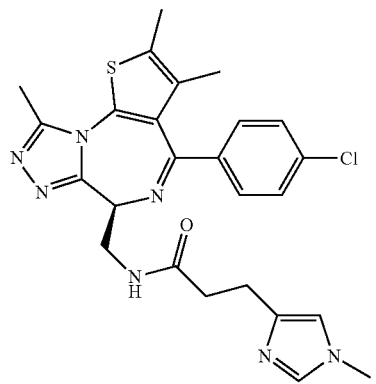
Secondary Amines:
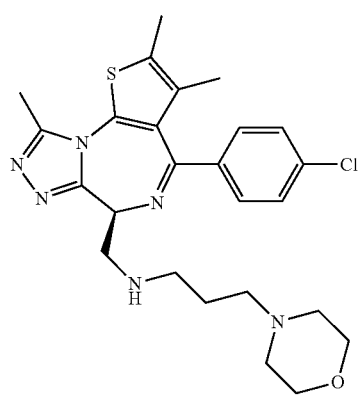
64
-continued
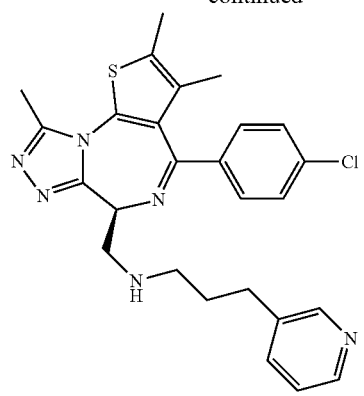
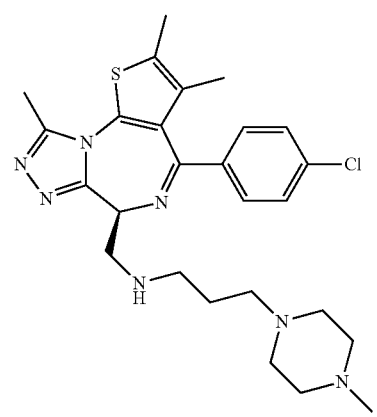
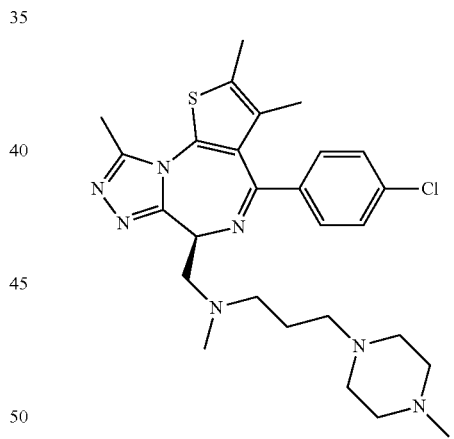
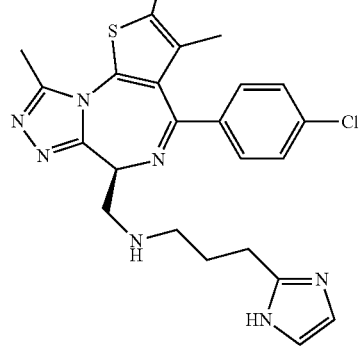

Boronic Acids:

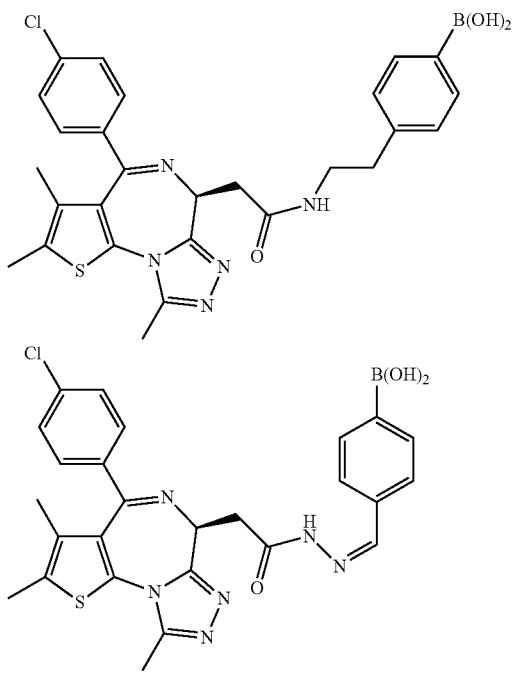

Another aspect of the present invention is a method for reducing the growth, proliferation, and survival of an insulinoma cell, the method comprising contacting the cell with a compound disclosed herein, or a pharmaceutically acceptable salt thereof. In one embodiment, the method for reducing the growth, proliferation and survival of an insulinoma cell further comprises selecting the compound for binding to a bromodomain of the BET family. In another embodiment, the BET family member is BRD2, BRD3, BRD4 or BRDT.

Another aspect of the present invention is a method of inducing cell death in an insulinoma cell, the method comprising contacting the cell with a compound disclosed herein, or a pharmaceutically acceptable salt thereof. In one embodiment, the method of inducing cell death in an insulinoma cell further comprises selecting the compound for binding to a bromodomain of the BET family. In another embodiment, the BET family member is BRD2, BRD3, BRD4 or BRDT.

In one embodiment, the subject is a mammal. In another embodiment, the subject is a human.

Another aspect of the present invention is a method for treating insulinoma in a subject in need thereof, the method comprising administering an effective amount of a compound disclosed herein, or a pharmaceutically acceptable salt thereof, wherein said compound is capable of binding a BET family bromodomain and disrupting bromodomain interaction with chromatin, thereby treating cancer.

"Insulinoma" is a rare tumor of the pancreas derived from beta cells and that secretes insulin. Insulin secretion in insulinomas is not regulated by glucose and the tumors will continue to secrete insulin and cause glucose levels to fall below normal. Presently, the most effective treatment option involves surgical removal of the tumor when possible. Medications, such as diazoxide and somatostatin, can also be utilized to lower insulin levels in patients who are not surgical candidates or who have otherwise inoperable tumors or for patients having other hyperinsulinaemic disorders. As such, effective therapies are limited.

"Congenital hyperinsulism (CHI)" is an inappropriate insulin secretion by the pancreatic beta cells caused by various genetic disorders. More specifically, CHI comprises a group of different genetic disorders with the common finding of recurrent episodes of hyperinsulinemic hypoglycemias due to an inappropriate secretion of insulin by the pancreatic beta cells. The genetic disorders can be caused by mutations in genes that regulate the release of insulin or in other genes involved in glucose regulation.

The former names of CHI are not obsolete: idiopathic hypoglycemis of infancy, nesidioblastosis, persistent hyperinsulinemic hypoglycemia of infancy, PHHI. Current treatment of CHI include administration of glucagon, somatostatin analogues, diazoxide and near-total pancreatectomy. Glucagon is not appropriate as a long-term treatment, and somatostatin analogs and diazoxide have been associated with severe adverse effects.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e., a compound of the present invention).

Treatment of a condition associated with hyperinsulinaemia (e.g., insulinoma, congenital hyperinsulism, polycystic ovary syndrome (PCOS), Beckwith-Wiedemann syndrome and in patients following gastric bypass surgery) in a subject in need thereof with pharmaceutically acceptable salts of the compounds of the present invention is also included. The term "pharmaceutically acceptable salt" also refers to a salt prepared from a compound disclosed herein, or any other compound delineated herein having a basic functional group, such as an amino functional group, and a pharmaceutically acceptable inorganic or organic acid. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

The term "pharmaceutically acceptable salt" also refers to a salt prepared from a compound disclosed herein or any other compound delineated herein, having an acidic functional group, such as a carboxylic acid functional group, and a pharmaceutically acceptable inorganic or organic base.

Salts of the compounds used in the methods of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine.

The invention also includes treatment of a condition associated with hyperinsulinaemia (e.g., insulinoma, congential hyperinsulism, polycystic ovary syndrome (PCOS), Beckwith-Wiedemann syndrome and in patients following gastric bypass surgery) in a subject in need thereof with various isomers and mixtures thereof. Certain compounds for the treatment of insulinomas or congenital hyperinsulism of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomers" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity (i.e., they do not rotate the plane of polarized light).

The compounds used in the methods of the present invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

As used herein, the term "tautomers" refers to isomers of organic molecules that readily interconvert by tautomerization, in which a hydrogen atom or proton migrates in the reaction, accompanied in some occasions by a switch of a single bond and an adjacent double bond.

As used herein the term "subject" refers to animals such as mammals, including, but not limited to, primates (e.g., humans), cows, sheep, goats, horses, pigs, dogs, cats, rabbits, guinea pigs, rates, mice or other bovine, ovine, equine, canine, feline, rodent or murine species.

The terms "treat" and "treating" are used interchangeably and include both therapeutic treatment and prophylactic treatment (reducing the likelihood of development). Both terms mean decrease, suppress, attenuate, diminish, arrest, or stabilize the development or progression of a condition, for example, a disease or disorder delineated herein. For example, hyperinsulinaemia is characterized by levels of insulin circulating in the blood that are in excess of those expected relative to the level of glucose. Hyperinsulinaemia is a result of unregulated insulin secretion by beta cells of the pancreas despite low blood glucose levels. Hyperinsulinaemia is associated with a variety of conditions such as insulinoma, congenital hyperinsulism, polycystic ovary syndrome (PCOS), Beckwith-Wiedemann syndrome and can occur in patients following gastric bypass surgery. Treatment of diseases or disorders associated with hyperinsulinaemia can include lessening the severity of the disease or disorder or improving the symptoms associated with the disease or disorder.

In a particular embodiment, treatment at least includes reduction of insulin secretion. In a more particular embodiment, treatment at least includes reduction of insulin secretion to levels in the blood that are not in excess of those expected relative to the level of glucose. In the case of insulinomas, treatment includes reduction of the tumor volume of the insulinoma, reduction of secretion of insulin or a combination thereof. As with any condition, the ability to treat more than one aspect (e.g., reduce insulin levels and reduce tumor volume) of a condition with a single drug provides benefits over the need for multiple agents.

A "condition associated with hyperinsulinaemia" means a condition in which levels of insulin circulating in the blood are in excess of those expected relative to the level of glucose. Conditions associated with hyperinsulinaemia are a result of unregulated insulin secretion by beta cells of the pancreas despite low blood glucose levels. Conditions associated with hyperinsulinaemia include, but are not limited to, insulinoma, congenital hyperinsulism, polycystic ovary syndrome (PCOS), Beckwith-Wiedemann syndrome and can occur in patients following gastric bypass surgery.

As used herein, the term "effective amount" refers to an amount which, when administered in a proper dosing regimen, is sufficient to treat (therapeutically or prophylactically) the target condition, in this case, a condition associated with hyperinsulinaemia (e.g., insulinoma, congenital hyperinsulism, polycystic ovary syndrome (PCOS), Beckwith-Wiedemann syndrome and in patients following gastric bypass surgery). For example, an effective amount is sufficient to reduce or ameliorate the severity, duration, or progression of the disorder being treated, prevent the advancement of the disorder being treated, cause the regression of the disorder being treated, or enhance or improve the prophylactic or therapeutic effect(s) of another therapy. For example, when the disorder associated with hyperinsulinaemia is an insulinoma, an effective amount can be an amount that reduces tumor volume of the insulinoma, reduces secretion of insulin or a combination thereof.

An effective amount may contain from about 0.001 mg/kg/day to about 1000 mg/kg/day. In one embodiment, the effective amount of a compound of the invention is from about 0.001 mg/kg/day to about 100 mg/kg/day. In another embodiment, the effective amount of a compound of the invention is from about 0.01 mg/kg/day to about 50 mg/kg/day. In yet another embodiment, the effective amount of a compound of the invention is from about 0.01 mg/kg/day to about 25 mg/kg/day. In yet another embodiment, the effective amount of a compound of the invention is from about 0.02 mg/kg/day to about 10 mg/kg/day. In yet another embodiment, the effective amount of a compound of the invention is from about 0.03 mg/kg/day to about 6 mg/kg/day, such as from about about 0.03 mg/kg/day to about 3 mg/kg/day.

Mode of Administration

The compositions used in the methods of the present invention include ocular, oral, nasal, transdermal, topical with or without occlusion, intravenous (both bolus and infusion), inhalable, and injection (intraperitoneally, subcutaneously, intramuscularly, intratumorally, or parenterally) formulations. In a particular embodiment, the compositions are for intravenous or oral administration. The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions used in the methods of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions used in the methods of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition used in the methods of the invention contains an effective amount of the active ingredient necessary to provide a therapeutic effect. The composition may contain from about 5,000 mg to about 0.01 mg of a compound of the invention, or pharmaceutically acceptable salt thereof, and may be constituted into any form suitable for the selected mode of administration. In one embodiment, the composition comprises about 5000 mg to about 0.01 mg of a compound of the invention, or pharmaceutically acceptable salt thereof. In another embodiment, the composition comprises about 1000 mg to about 0.01 mg of a compound of the invention, or pharmaceutically acceptable salt thereof. In yet another embodiment, the composition comprises about 100 mg to about 0.01 mg of a compound of the invention, or pharmaceutically acceptable salt thereof. The composition may be administered about 1 to about 5 times per day. Daily administration or periodic dosing may be employed.

For oral administration, the composition is preferably in the form of a tablet or capsule containing (e.g., 1000 to 0.5 milligrams of the active compound). Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate, or combinations thereof) may be used.

Compounds used in the methods of the invention may also be administered via a slow release composition, wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles or nanoemulsions (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound disclosed herein and used in the methods of the invention may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired. In one embodiment, the compound, or a pharmaceutically acceptable salt thereof, is administered orally. In another embodiment, the compound, or a pharmaceutically acceptable salt thereof, is administered intravenously. The compounds used in the methods may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit can contain from about 0.005 to about 99% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds used in the methods of the invention may be administered intranasally using a suitable intranasal vehicle.

In another embodiment, the compounds used in the methods of this invention may be administered directly to the lungs by inhalation.

Compounds used in the methods of the invention may also be administered topically or enhanced by using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

Combination Therapy

In certain embodiments, the methods of the present invention also include treatment of a condition associated with hyperinsulinaemia (e.g., insulinoma, congenital hyperinsulism, polycystic ovary syndrome (PCOS), Beckwith-Wiedemann syndrome and in patients following gastric bypass surgery) using a compound of the invention, or a pharmaceutically acceptable salt thereof, alone or in combination with one or more therapeutic agents, or a pharmaceutically acceptable salt thereof. The one or more therapeutic agent can be, for example, any agent that is capable of treating insulinomas. Alternatively, the one or more therapeutic agent can be any agent known in the art to treat cancer, any agent that is an insulin secretion inhibiting agent, or any agent of benefit to the patient when administered in combination with a compound of the invention. Examples of therapeutic agents known in the art to treat cancer and suitable for use in combination with the compounds of the invention include, but are not limited to, CdK4/6 inhibitors (e.g., PD0332992(palbociclib)), 5-fluorouracil, 6-mercaptopurine, capecitabine, cladribine, clofarabine, cytarabine, floxuridine, fludarabin, gemcitabine, hydroxyurea, methotrexate, pemetrexed, pentostatin, thioguanine, daunorubicin, doxorubicin, epirubicin, idarubicin, actinomycin-D, bleomycin, mitomycin-C, topotecan, irinotecan, etoposide, teniposide, mitoxantrone, paclitaxel, docetaxel, ixabepilone, vinblastine, vincristine, vinorelbine, estramustine, prednisone, methylprednisolone, dexamethasone, mechlorethamine, chlorambucil, cyclophosphamide, ifosfamide, melphalan, streptozocin, carmustine, lomustine, busulfan, dacarbazine, temozolomide, thiotepa and altretamine. Examples of insulin secretion inhibiting agents include, but are not limited to, diazoxide, somatostatin, octreotide, and nifedipine. In particular, the one or more therapeutic agents do not diminish the effects of the therapy the effects of the primary administration.

In certain embodiments, the methods of the present invention also include treatment of congenital hyperinsulism using a compound of the invention, or a pharmaceutically acceptable salt thereof, alone or in combination with one or more therapeutic agents, or a pharmaceutically acceptable salt thereof. The one or more therapeutic agent can be any agent that is capable of treating congenital hyperinsulism. Alternatively, the one or more therapeutic agent can be any agent known in the art that is an insulin secretion inhibiting agent, or any agent of benefit to the patient when administered in combination with a compound of the invention. Examples of insulin secretion inhibiting agents include, but are not limited to, diazoxide, somatostatin, octreotide, and nifedipine. In particular, the one or more therapeutic agents do not diminish the effects of the therapy the effects of the primary administration.

In one embodiment, the combination therapy comprises a compound of the invention, or a pharmaceutically acceptable salt thereof, and a therapeutic agent known in the art to treat cancer, or a pharmaceutically acceptable salt thereof and the disorder associated with hyperinsulinaemia is an insulinoma.

In another embodiment, the combination therapy comprises a compound of the invention, or a pharmaceutically acceptable salt thereof, and an insulin secretion inhibiting agent, or a pharmaceutically acceptable salt thereof.

In yet another embodiment, the combination therapy comprises a compound of the invention, or a pharmaceutically acceptable salt thereof, a therapeutic agent known in the art to treat cancer, or a pharmaceutically acceptable salt thereof, and an insulin secretion inhibiting agent, or a pharmaceutically acceptable salt thereof and the condition associated with hyperinsulinaemia is an insulinoma.

In another embodiment, the combination therapy comprises a compound of the invention, or a pharmaceutically acceptable salt thereof, and an agent that is capable of treating congenital hyperinsulism, or a pharmaceutically acceptable salt thereof.

In a further embodiment, the combination therapy comprises a compound of the invention, or a pharmaceutically acceptable salt thereof, an agent that is capable of treating congenital hyperinsulism, or a pharmaceutically acceptable salt thereof, and an insulin secretion inhibiting agent, or a pharmaceutically acceptable salt thereof.

The language "in combination with" or "combination therapy" refers to the co-administration of a first amount of a compound capable of treating a disorder associated with hyperinsulinaemia, or a pharmaceutically acceptable salt thereof, and a second amount of at least one therapeutic agent, or a pharmaceutically acceptable salt thereof, wherein the first and second amounts together comprise a therapeutically effective amount to treat a disorder associated with hyperinsulinaemia. Combination therapy encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of the compound capable of treating a disorder associated with hyperinsulinaemia, or a pharmaceutically acceptable salt thereof, and a second amount of at least one therapeutic agent, or a pharmaceutically acceptable salt thereof, the compounds are administered sufficiently close in time to have the desired therapeutic effect. For example, the period of time between each administration, which can result in the desired therapeutic effect, can range from minutes to hours and can be determined taking into account the properties of each compound such as potency, solubility, bioavailability, plasma half-life and kinetic profile. For example, the compound capable of treating disorders associated with hyperinsulinaemia, or a pharmaceutically acceptable salt thereof, and at least one therapeutic agent, or a pharmaceutically acceptable salt thereof, can be administered in any order within about 24 hours of each other, within about 16 hours of each other, within about 8 hours of each other, within about 4 hours of each other, within about 1 hour of each other or within about 30 minutes of each other.

EXEMPLIFICATION

The following abbreviations are used in throughout the application.
Ac acetyl
AcOH acetic acid
Actb Actin (beta)
AIBN 2,2'-azobis(2-methylpropionitrile)
aq aqueous
Asp aspartic acid
BET Bromodomain and extra-terminal domain
BRDT Bromodomain testis-specific protein
BRD2 Bromodomain containing protein 2
BRD3 Bromodomain containing protein 3
Brd4 Bromodomain containing protein 4
Bn benzyl
Boc tert-butoxycarbonyl
BSA bovine serum albumen
Bu butyl
Cdk4 Cyclin dependent kinase 4
Cdk6 Cyclin dependent kinase 6
DIEA N,N-diisopropylethylamine
DMF N,N-dimethylformamide
DMSO dimethyl sulfoxide
EDC N-(3-dimethylaminopropyl)-N'-ethylcarbodiimide
ESI electrospray ionization
Et ethyl
EtOAc ethyl acetate
EtOH ethanol
Fmoc Fluorenylmethyloxycarbonyl
Gapdh Glyceraldehyde 3-phosphate dehydrogenase
Gck Glucokinase
HCTU (2-(6-chloro-1H-benzotriazole-1-yl)-1,1,3,3-tetramethylaminium hexafluorophosphate
His histidine
HPLC high performance liquid chromatography
HRMS high resolution mass spectrometry
i iso
$IC_{50}$ Half maximal growth inhibitory concentration
Igf2 Insulin like growth factor 2
Ins1 Insulin 1
Ins2 Insulin 2
MeoH methanol
Me methyl
MS mass spectrometry
MW molecular weight
Myc c-Myc
Mycn n-Myc
NMR nuclear magnetic resonance spectrometry
PBS Phosphate buffered saline
Ph phenyl
PEG Polyethylene glycol
Pr propyl
PyBOP (benzotriazol-1-yloxyl)tripyrrolidinophosphonium
RT Reverse transcription
qPCR Quantitative polymerase chain reaction
s secondary
S sulfur
t tertiary
THF tetrahydrofuran
TLC thin layer chromatography
qPCR Quantitative polymerase chain reaction
18sRNA 18s ribosomal RNA

I. CHEMICAL EXAMPLES

Synthesis and Methods of Preparation

Compounds of the invention can be synthesized by methods described herein, and/or according to methods known to one of ordinary skill in the art in view of the description herein.

Instrumentation

Proton and carbon-13 nuclear magnetic resonance ($^{1}$H NMR and $^{13}$C NMR) spectra were recorded with a Varian inverse probe 600 INOVA spectrometer at the Harvard Medical School East Quad NMR Facility. Chemical shifts are recorded in parts per million on the δ scale and are referenced from the residual protium in the NMR solvent, (CHCl$_3$: δ 7.24) for $^1$H NMR, and the carbon resonances of the solvent, (CDCl$_3$: δ 77.2) for $^{13}$C NMR, respectively. Data is reported as follows: chemical shift multiplicity (s=singlet, d=doublet, t=triplet, q=quartet, m=multiplet, br=broad), and coupling constant(s) in Hertz, integration. High resolution mass spectra (HRMS) were recorded on a Bruker APEX 4.7 Tesler. FTMS spectrometer using electrospray ion source (ESI) at the Instrumentation Facility of the Department of Chemistry, Massachusetts Institute of Technology. The intermediates and final product were purified with a CombiFlash RF system (Teledyne Isco). Organic solutions were concentrated on Büichi R-205 rotary evaporators. The enantiomeric purities were checked with Berger Supercritical Fluid Chromatography (SFC) and an AS-H column. The enantiomeric preparative purification was performed with Agilent High Pressure Liquid Chromatography and an OD-H column (Broad Institute of Harvard and MIT).

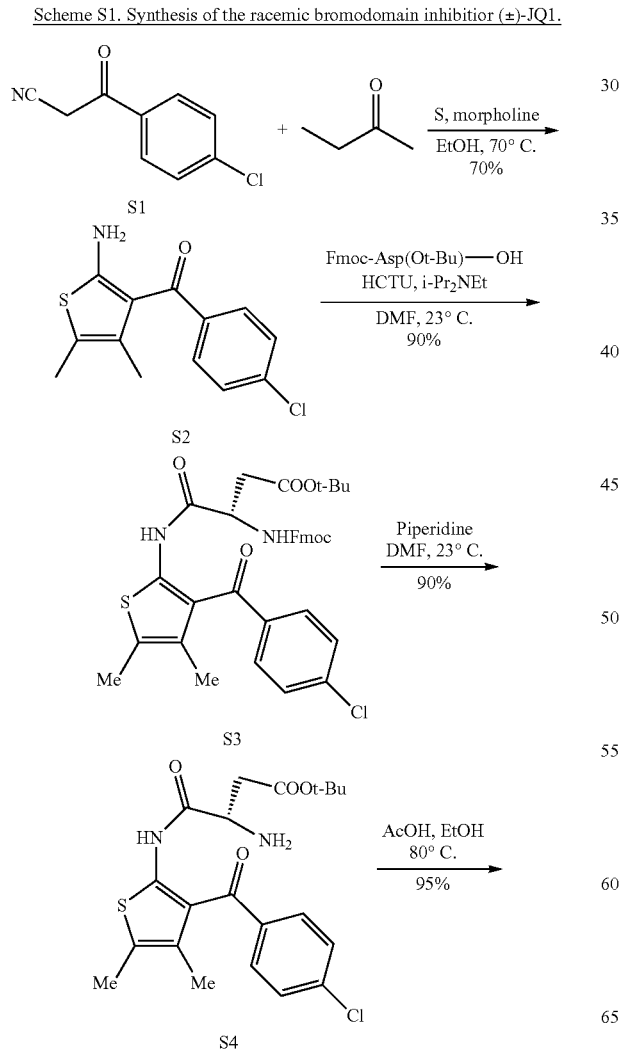

Scheme S1. Synthesis of the racemic bromodomain inhibitior (±)-JQ1.

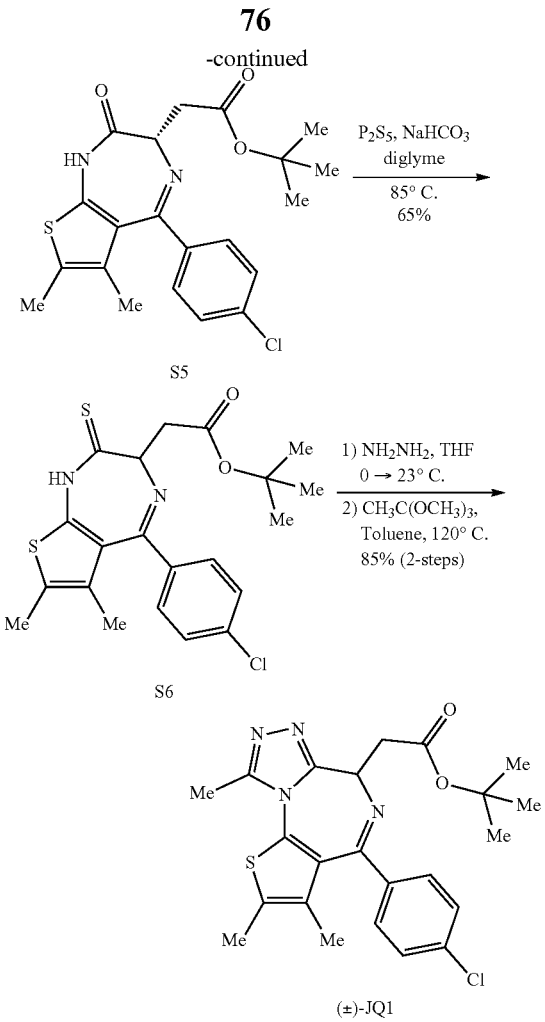

Example 1

(2-amino-4,5-dimethylthiophen-3-yl)(4-chlorophenyl)methanone (S2)

The compound JQ1 was prepared according to the scheme shown above.

Sulfur (220 mg, 6.9 mmol, 1.00 equiv) was added as a solid to a solution of 4-chlorobenzoyl acetonitrile S1 (1.24 g, 6.9 mmol, 1 equiv), 2-butanone (0.62 ml, 6.9 mmol, 1.00 equiv), and morpholine (0.60 ml, 6.9 mmol, 1.00 equiv) in ethanol (20 ml, 0.35 M) at 23° C. The mixture was then heated to 70° C. After 12 hours, the reaction mixture was cooled to 23° C. and poured into brine (100 ml). The aqueous layer was extracted with ethyl acetate (3×50 ml). The combined organic layers were washed with brine (50 ml), dried over anhydrous sodium sulphate, filtered, and concentrated under reduced pressure. The residue was purified by flash column chromatography (Combiflash RF system, 40 gram silica gel, gradient 0 to 100% ethyl acetate-hexanes) to afford S2 (1.28 g, 70%) as a yellow solid.

(S)-tert-Butyl-3-({[(9H-fluoren-9-yl)methoxy]carbonyl}amino)-4-{[3-(4-chlorobenzoyl)-4,5-dimethylthiophen-2-yl]amino}-4-oxobutanoate (S3)

(2-(6-Chloro-1H-benzotriazole-1-yl)-1,1,3,3-tetramethylaminium hexafluorophosphate (HCTU) (827 mg, 2.0 mmol, 2.00 equiv), and N,N-diisopropylethylamine (0.72 ml, 4.0 mmol, 4.00 equiv) were added sequentially to a solution of 9-fluorenylmethoxycarbonyl-aspartic acid β-tert-butyl ester [Fmoc-Asp(Ot-Bu)-OH] (864 mg, 2.1 mmol, 2.10 equiv) in N,N-dimethylformamide (1.5 ml, 1.0 M). The mixture was then stirred at 23° C. for 5 min. S2 (266 mg, 1.0 mmol, 1 equiv) was then added as a solid. The reaction mixture was stirred at 23° C. After 16 hours, ethyl acetate (20 ml) and brine (20 ml) were added. The two layers were separated, and the aqueous layer was extracted with ethyl acetate (2×20 ml). The combined organic layers were washed with brine (30 ml), dried over with anhydrous sodium sulphate, filtered, and concentrated under reduced pressure. The residue was purified by flash column chromatography (Combiflash RF, 40 gram silica gel, gradient 0 to 100% ethyl acetate-hexanes) to afford S3 (625 mg, 90%) as brown oil.

(S)-tert-butyl 3-amino-4-((3-(4-chlorobenzoyl)-4,5-dimethylthiophen-2-yl)amino)-4-oxobutanoate (S4)

Compound S3 (560 mg, 0.85 mmol, 1 equiv) was dissolved into 20% piperidine in DMF solution (4.0 ml, 0.22 M) at 23° C. After 30 min, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), dried over anhydrous sodium sulphate, filtered, and concentrated under reduced pressure. The residue was purified by flash column chromatography (Combiflash RF system, 24 gram silica gel, gradient 0 to 100% ethyl acetate-hexanes) to afford free amine S4 (370 mg, 90%) as yellow solid. The enantiomeric purity was reduced to 75% (determined with Berger Supercritical Fluid Chromatography (SFC) using AS-H column).

(S)-tert-Butyl 2-(5-(4-chlorophenyl)-6,7-dimethyl-2-oxo-2,3-dihydro-1H-thieno[2,3-e][1,4]diazepin-3-yl)acetate (S5)

Amino ketone (S4) (280 mg, 0.63 mmol) was dissolved in 10% acetic acid ethanol solution (21 ml, 0.03 M). The reaction mixture was heated to 85° C. After 30 minutes, all solvents were removed under reduced pressure. The residue was purified by flash column chromatography (Combiflash RF system, 12 gram silica gel, gradient 0 to 100% ethyl acetate-hexanes) to afford compound S5 (241 mg, 95%) as white solid. Enantiomeric purity of S5 was 67% (determined with Berger Supercritical Fluid Chromatography (SFC) using an AS-H column).

tert-Butyl 2-(5-(4-chlorophenyl)-6,7-dimethyl-2-thioxo-2,3-dihydro-1H-thieno[2,3-e][1,4]diazepin-3-yl)acetate (S6)

Phosphorus pentasulfide (222 mg, 1.0 mmol, 2.00 equiv) and sodium bicarbonate (168 mg, 2.0 mmol, 4.00 equiv) were added sequentially to a solution of S5 (210 mg, 0.5 mmol, 1 equiv) in diglyme (1.25 ml, 0.4M). The reaction mixture was heated to 90° C. After 16 h, brine (20 ml) and ethyl acetate (35 ml) were added. The two layers were separated, and the aqueous layer was extracted with ethyl acetate (3×30 ml). The combined organic layers were washed with brine (2×15 ml), dried over anhydrous sodium sulphate, filtered, and concentrated under reduced pressure. The residue was purified by flash column chromatography (Combiflash RF system, 24 gram silica gel, gradient 0 to 100% ethyl acetate-hexanes) to afford S6 (141 mg, 65%) as brown solid and recovered S5 (73 mg, 34%).

tert-Butyl 2-(4-(4-chlorophenyl)-2,3,9-trimethyl-6H-thieno[3,2-f][1,2,4]triazolo[4,3-a][1,4]diazepin-6-yl)acetate [(±)JQ1]

Hydrazine (0.015 ml, 0.45 mmol, 1.25 equiv) was added to a solution of S6 (158 mg, 0.36 mmol, 1 equiv) in THF (2.6 ml, 0.14 M) at 0° C. The reaction mixture was warmed to 23° C., and stirred at 23° C. for 1 h. All solvents were removed under reduced pressure. The resulting hydrazine intermediate was used directly without purification. The hydrazine intermediate was then dissolved in a 2:3 mixture of trimethyl orthoacetate and toluene (6 ml, 0.06 M). The reaction mixture was heated to 120° C. After 2 h, all the solvents were removed under reduced pressure. The residue was purified by flash column chromatography (Combiflash system, 4 g silica gel, gradient 0 to 100% ethyl acetate-hexanes) to afford JQ1 (140 mg, 85% in 2 steps) as white solid. The reaction conditions further epimerized the stereogenic center, resulting in the racemate of JQ1 (determined with Berger Supercritical Fluid Chromatography (SFC) with an AS-H column).

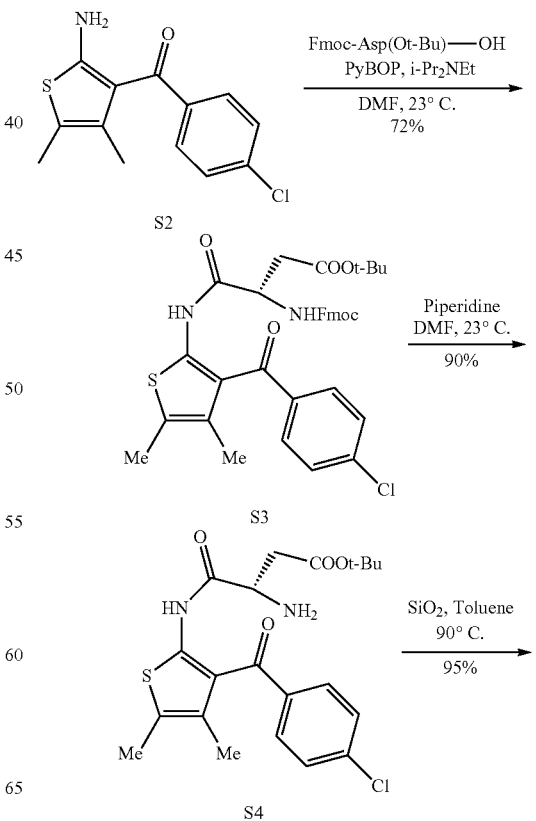

Scheme S2. Synthesis of enantiomerically enriched (+)-JQ1.

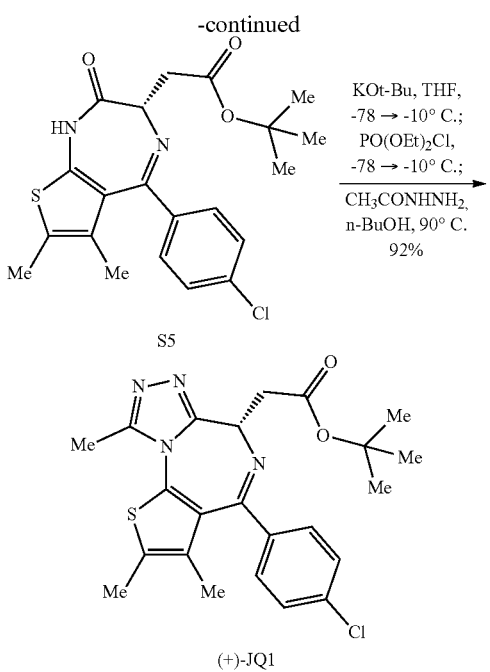

(S)-tert-Butyl-3-({[(9H-fluoren-9-yl)methoxy]carbonyl}amino)-4-{[3-(4-chlorobenzoyl)-4,5-dimethylthiophen-2-yl]amino}-4-oxobutanoate (S3)

(Benzotriazol-1-yloxyl)tripyrrolidinophosphonium (PyBOP) (494 mg, 0.95 mmol, 0.95 equiv), N,N-diisopropylethylamine (0.50 ml, 2.8 mmol, 2.75 equiv) were added sequentially to a solution of 9-fluorenylmethoxycarbonyl-aspartic acid β-tert-butyl ester [Fmoc-Asp(Ot-Bu)-OH] (411 mg, 1.00 mmol, 1.0 equiv) in N,N-dimethylformamide (1.0 ml, 1.0 M). The mixture was then stirred at 23° C. for 5 min S2 (266 mg, 1.0 mmol, 1 equiv) was then added as solid. The reaction mixture was stirred at 23° C. After 4 h, ethyl acetate (20 ml) and brine (20 ml) were added. The two layers were separated, and the aqueous layer was extracted with ethyl acetate (2×20 ml). The combined organic layers were washed with brine, dried over with anhydrous sodium sulphate, filtered, and concentrated under reduced pressure. The residue was purified by flash column chromatography (Combiflash RF system, 40 gram silica gel, gradient 0 to 100% ethyl acetate-hexanes) to afford S3 (452 mg, 72%) as brown oil.

(S)-tert-butyl 3-amino-4-((3-(4-chlorobenzoyl)-4,5-dimethylthiophen-2-yl)amino)-4-oxobutanoate (S4)

Compound S3 (310 mg, 0.47 mmol, 1 equiv) was dissolved into 20% piperidine in DMF solution (2.2 ml, 0.22 M) at 23° C. After 30 min, ethyl acetate (20 ml) and brine (20 ml) were added to the reaction mixture. The two layers were separated, and the aqueous layer was extracted with ethyl acetate (2×20 ml). The combined organic layers were washed with brine (3×25 ml), dried over anhydrous sodium sulphate, filtered, and concentrated under reduced pressure. The residue was purified by flash column chromatography (Combiflash RF system, 24 gram silica gel, gradient 0 to 100% ethyl acetate-hexane) to afford free amine S4 (184 mg, 90%) as yellow solid. The enantiomeric purity of S4 was 91% (checked with Berger Supercritical Fluid Chromatography (SFC) using an AS-H column).

(S)-tert-Butyl 2-(5-(4-chlorophenyl)-6,7-dimethyl-2-oxo-2,3-dihydro-1H-thieno[2,3-e][1,4]diazepin-3-yl)acetate (S5)

Amino ketone (S4) (184 mg, 0.42 mmol) was dissolved in toluene (10 ml, 0.04 M). Silica gel (300 mg) was added, and the reaction mixture was heated to 90° C. After 3 h, the reaction mixture was cooled to 23° C. The silica gel was filtered, and washed with ethyl acetate. The combined filtrates were concentrated. The residue was purified by flash column chromatography (Combiflash RF system, 12 gram silica gel, gradient 0 to 100% ethyl acetate-hexanes) to afford compound S5 (168 mg, 95%) as white solid. Enantiomeric purity of S5 was 90% (determined with Berger Supercritical Fluid Chromatography (SFC) using an AS-H column).

(S)-tert-Butyl 2-(4-(4-chlorophenyl)-2,3,9-trimethyl-6H-thieno[3,2-f][1,2,4]triazolo [4,3-a][1,4]diazepin-6-yl)acetate [(+)JQ1]

Potassium tert-butoxide (1.0 M solution in THF, 0.3 ml, 0.30 mmol, 1.10 equiv) was added to a solution of S5 (114 mg, 0.27 mmol, 1 equiv) in THF (1.8 ml, 0.15 M) at −78° C. The reaction mixture was warmed to −10° C., and stirred at 23° C. for 30 min. The reaction mixture was cooled to −78° C. Diethyl chlorophosphate (0.047 ml, 0.32 mmol, 1.20 equiv) was added to reaction mixture. The resulting mixture was warmed to −10° C. over 45 min. Acetic hydrazide (30 mg, 0.40 mmol, 1.50 equiv) was added to reaction mixture. The reaction mixture was stirred at 23° C. After 1 h, 1-butanol (2.25 ml) was added to reaction mixture, which was heated to 90° C. After 1 h, all solvents were removed under reduce pressure. The residue was purified with flash column chromatography (Combiflash system, 4 g silica gel, gradient 0 to 100% ethyl acetate-hexanes) to afford (+)-JQ1 (114 mg, 92%) as white solid with 90% enantiomeric purity (determined with Berger Supercritical Fluid Chromatography (SFC) using AS-H column, 85% hexanes-methanol, 210 nm, $t_R$ (R-enantiomer)=1.59 min, $t_R$ (S-enantiomer)=3.67 min). The product was further purified by chiral preparative HPLC (Agilent High Pressure Liquid Chromatography using an OD-H column) to provide the S-enantiomer in greater than 99% ee.

$^1$H NMR (600 MHz, CDCl$_3$, 25° C.) δ 7.39 (d, J=8.4 Hz, 2H), 7.31 (d, J=8.4 Hz, 2H), 4.54 (t, J=6.6 MHz, 1H), 3.54-3.52 (m, 2H), 2.66 (s, 3H), 2.39 (s, 3H), 1.67 (s, 3H), 1.48 (s, 9H).

$^{13}$C NMR (150 MHz, CDCl$_3$, 25° C.) δ 171.0, 163.8, 155.7, 150.0, 136.9, 131.1, 130.9, 130.6, 130.3, 128.9, 81.2, 54.1, 38.1, 28.4, 14.6, 13.5, 12.1.

HRMS(ESI) calc'd for $C_{21}H_{24}ClN_2O_3S$ [M+H]$^+$: 457.1460, found 457.1451 m/z.

TLC (EtOAc), Rf: 0.32 (UV)

$[\alpha]^{22}_D$=+75 (c 0.5, CHCl$_3$)

(−)-JQ1 was synthesized in a similar manner, employing Fmoc-D-Asp(Ot-Bu)-OH as a starting material, and was further purified by chiral preparative HPLC (Agilent High Pressure Liquid Chromatography using an OD-H column) to afford the R-enantiomer in greater than 99% ee. $[\alpha]^{22}_D$=−72 (c 0.5, CHCl$_3$).

Synthesis of Additional Compounds

Additional compounds of the invention were prepared as illustrated in Scheme S3.

Scheme S3. Synthesis of hydrazine derivatives.

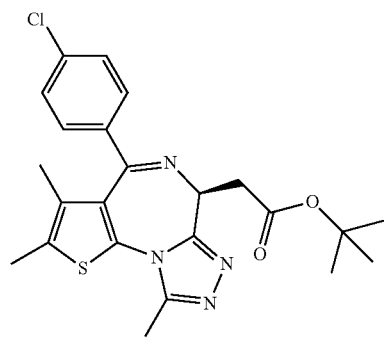

(1), (+)-JQ1

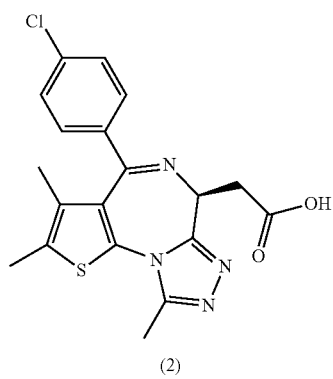

(2)

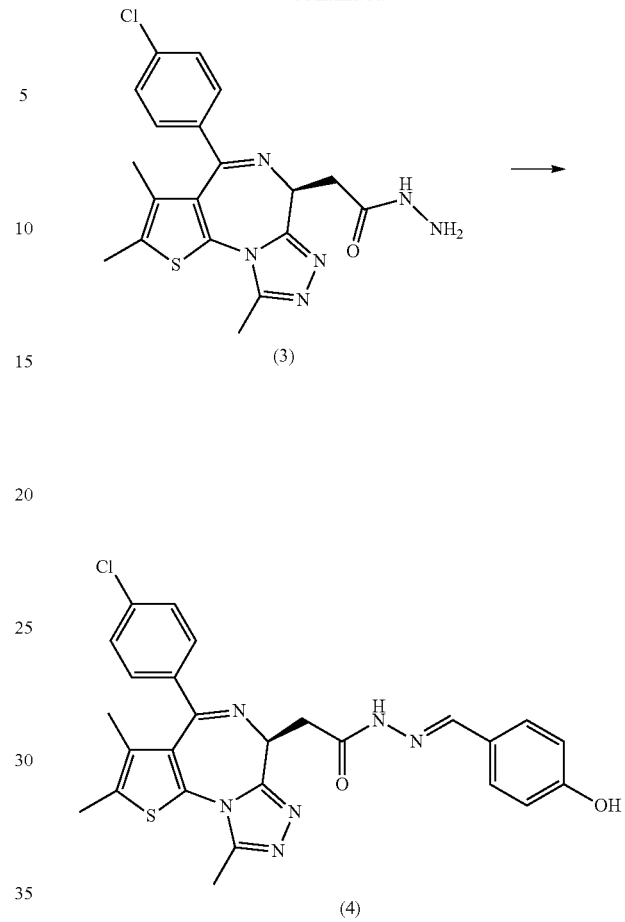

As shown in Scheme S3, the t-butyl ester of (+)-JQ1 (1) was cleaved to yield the free acid (2), which was coupled with hydrazine to yield the hydrazide (3). Reaction with 4-hydroxybenzaldehyde yielded the hydrazone (4).

Both hydrazide (3) and hydrazone (4) showed activity in at least one biological assay.

Table A below shows the additional compounds prepared for use in the methods of the present invention.

| Compound Name | Structure | MS [M + H]+ m/z (Observed) |
|---|---|---|
| (S)-JQ1 | 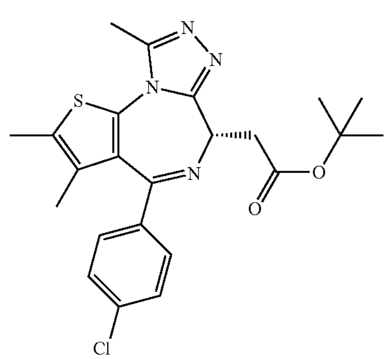 [SMILES: Cc1sc2c(c1C)C(c1ccc(Cl)cc1)=N[C@@H](CC(=O)OC(C)(C)C)c1nnc(C)n1-2] | 457.1 |

-continued

| Compound Name | Structure | MS [M + H]+ m/z (Observed) |
|---|---|---|
| (R)-JQ1 | 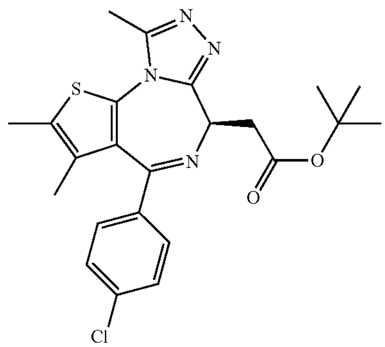 [SMILES: Cc1sc2c(c1C)C(c1ccc(Cl)cc1)=N[C@H](CC(=O)OC(C)(C)C)c1nnc(C)n1-2] | 457.1 |
| (S)-JQ3 | 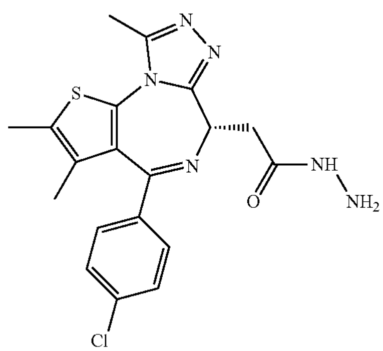 [SMILES: Cc1sc2c(c1C)C(c1ccc(Cl)cc1)=N[C@@H](CC(=O)NN)c1nnc(C)n1-2] | 415.1 |
| (S)-JQ4 | 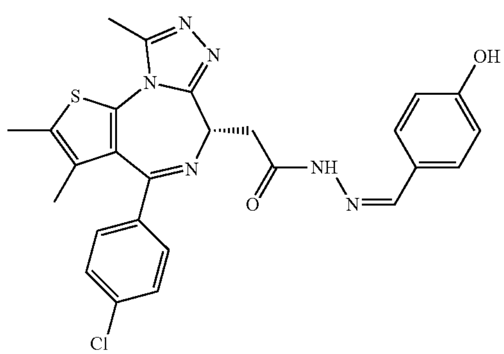 [SMILES: Cc1sc2c(c1C)C(c1ccc(Cl)cc1)=N[C@@H](CC(=O)N/N=C\c1ccc(O)cc1)c1nnc(C)n1-2] | 519.1 |
| (S)-JQ6 | 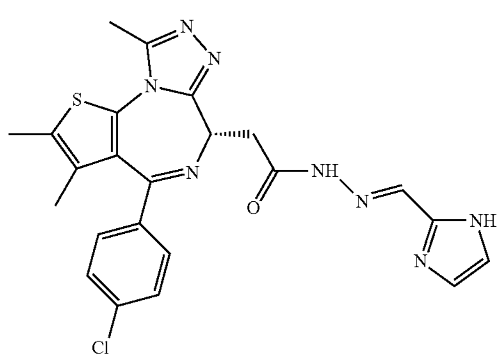 [SMILES: Cc1sc2c(c1C)C(c1ccc(Cl)cc1)=N[C@@H](CC(=O)N/N=C/c1ncc[nH]1)c1nnc(C)n1-2] | 493.1 |

-continued
| Compound Name | Structure | MS [M + H]+ m/z (Observed) |
|---|---|---|
| (S)-JQ7 | 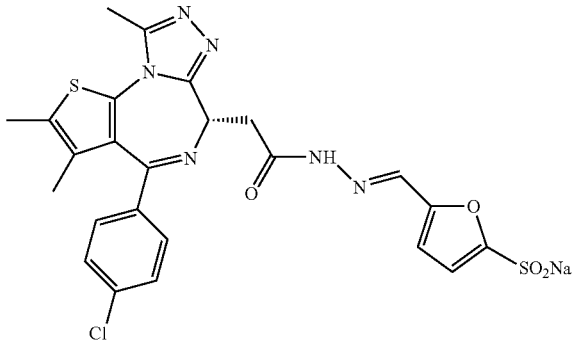 | 579.0 |
| (S)-JQ8 | 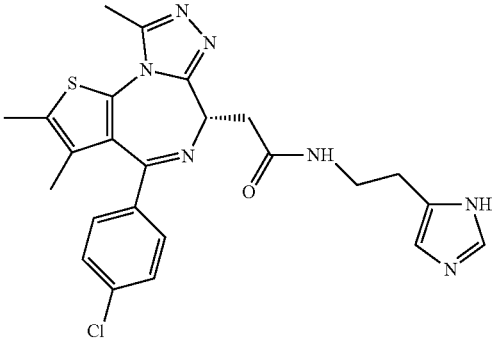 [SMILES: Cc1sc2c(c1C)C(c1ccc(Cl)cc1)=N[C@@H](CC(=O)NCCc1cnc[nH]1)c1nnc(C)n1-2] | 494.1 |
| (S)-JQ10 | 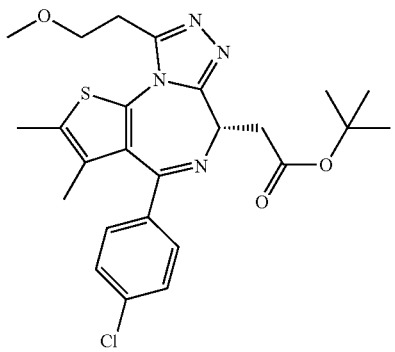 [SMILES: COCCc1nnc2n1-c1sc(C)c(C)c1C(c1ccc(Cl)cc1)=N[C@H]2CC(=O)OC(C)(C)C] | 501.1 |
| (S)-JQ11 | 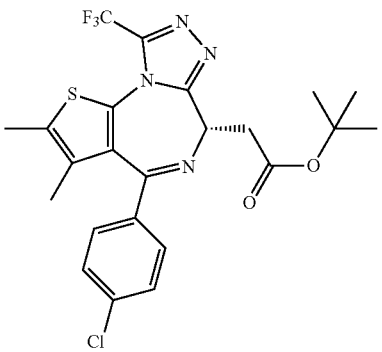 [SMILES: Cc1sc2c(c1C)C(c1ccc(Cl)cc1)=N[C@@H](CC(=O)OC(C)(C)C)c1nnc(C(F)(F)F)n1-2] | 511.1 |

-continued

| Compound Name | Structure | MS [M + H]+ m/z (Observed) |
|---|---|---|
| (S)-JQ1-FITC | 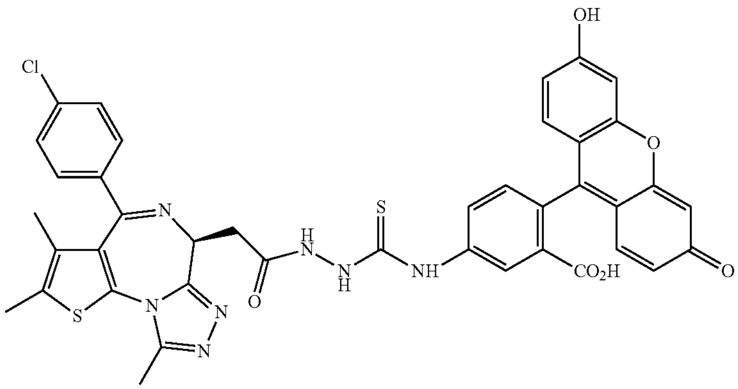 [SMILES: Cc1sc2c(c1C)C(c1ccc(Cl)cc1)=N[C@@H](CC(=O)NNC(=S)Nc1ccc(-c3c4ccc(=O)cc-4oc4cc(O)ccc34)c(C(=O)O)c1)c1nnc(C)n1-2] | 804.1 |
| JQ1-Biotin | | 829.3 |
| (S)-JQ13 | 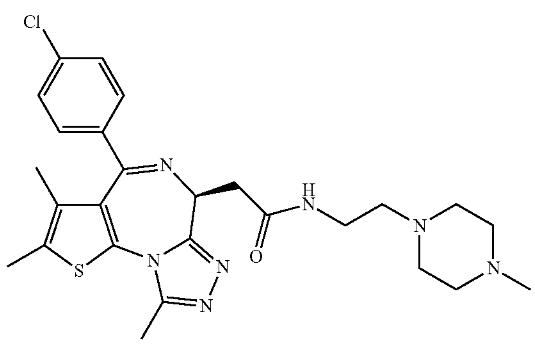 | 526.2 |
| (S)-KS1 | 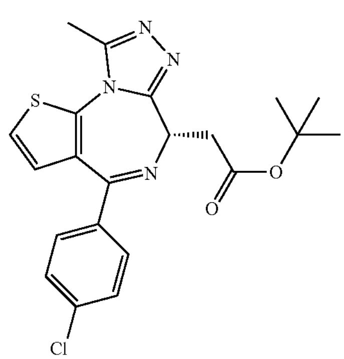 [SMILES: Cc1nnc2n1-c1sccc1C(c1ccc(Cl)cc1)=N[C@H]2CC(=O)OC(C)(C)C] | 429.1 |

| Compound Name | Structure | MS [M + H]+ m/z (Observed) |
|---|---|---|
| (S)-JQ18 | 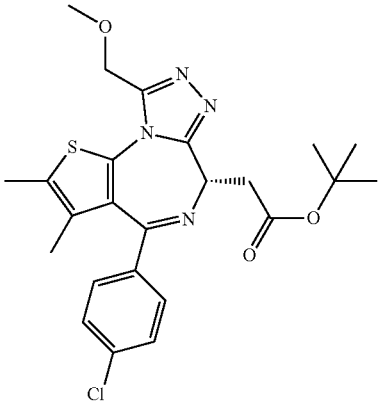 [SMILES: COCc1nnc2n1-c1sc(C)c(C)c1C(c1ccc(Cl)cc1)=N[C@H]2CC(=O)OC(C)(C)C]<br>Chemical Formula: $C_{24}H_{27}ClN_4O_3S$<br>Exact Mass: 486.14924<br>Molecular Weight: 487.01418 | 487.1 |
| (S)-JQ19 | 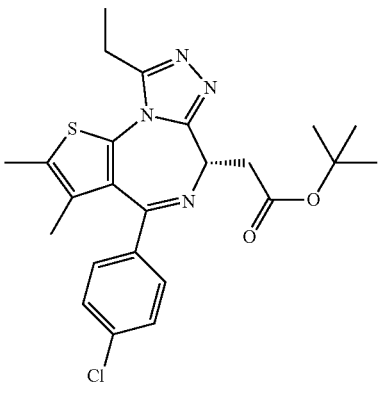 [SMILES: CCc1nnc2n1-c1sc(C)c(C)c1C(c1ccc(Cl)cc1)=N[C@H]2CC(=O)OC(C)(C)C]<br>Chemical Formula: $C_{24}H_{27}ClN_4O_2S$<br>Exact Mass: 470.15432<br>Molecular Weight: 471.01478 | 471.1 |
| JQ20 | 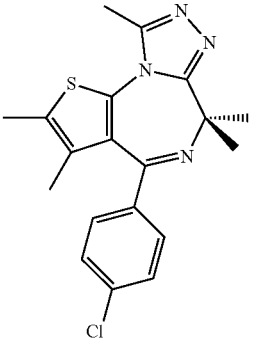<br>Chemical Formula: $C_{19}H_{19}ClN_4S$<br>Exact Mass: 370.10190<br>Molecular Weight: 370.89896<br>JQI-II-023 | 370.1 |

| Compound Name | Structure | MS [M + H]+ m/z (Observed) |
|---|---|---|
| (S)-JQ21 | 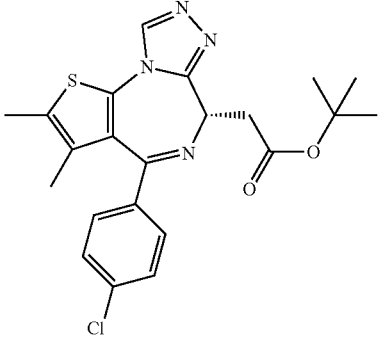 [SMILES: Cc1sc2c(c1C)C(c1ccc(Cl)cc1)=N[C@@H](CC(=O)OC(C)(C)C)c1nncn1-2]<br>JQI-II-024<br>Chemical Formula: C$_{22}$H$_{23}$ClN$_4$O$_2$S<br>Exact Mass: 442.12302<br>Molecular Weight: 442.96162 | 443.1 |
| JQ24A | 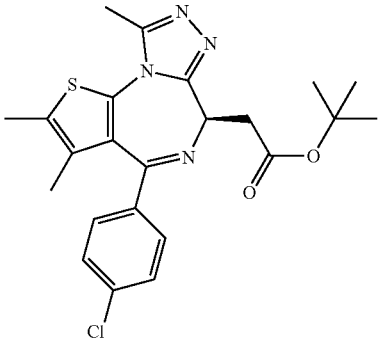 [SMILES: Cc1sc2c(c1C)C(c1ccc(Cl)cc1)=N[C@H](CC(=O)OC(C)(C)C)c1nnc(C)n1-2]<br>Chemical Formula: C$_{24}$H$_{26}$ClN$_3$O$_2$S<br>Exact Mass: 455.1434<br>Molecular Weight: 456.0001 | 456.1 |
| JQ24B | 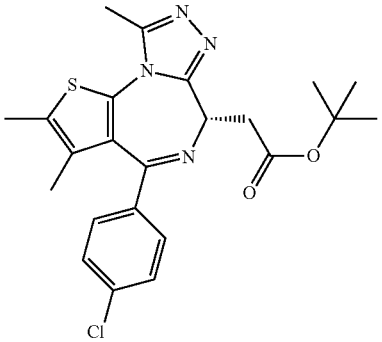 [SMILES: Cc1sc2c(c1C)C(c1ccc(Cl)cc1)=N[C@@H](CC(=O)OC(C)(C)C)c1nnc(C)n1-2]<br>Chemical Formula: C$_{24}$H$_{26}$ClN$_3$O$_2$S<br>Exact Mass: 455.1434<br>Molecular Weight: 456.0001 | 456.1 |

-continued
| Compound Name | Structure | MS [M + H]+ m/z (Observed) |
|---|---|---|
| (S)-JQ25 | 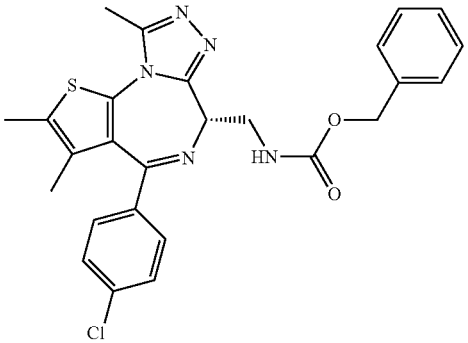 [SMILES: Cc1sc2c(c1C)C(c1ccc(Cl)cc1)=N[C@@H](CNC(=O)OCc1ccccc1)c1nnc(C)n1-2]<br>Chemical Formula: C$_{26}$H$_{24}$ClN$_5$O$_2$S<br>Exact Mass: 505.1339<br>Molecular Weight: 506.0191 | 506.1 |
| JQB | 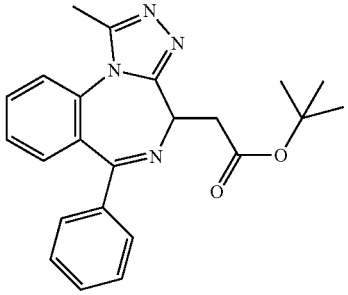 [SMILES: Cc1nnc2n1-c1ccccc1C(c1ccccc1)=NC2CC(=O)OC(C)(C)C]<br>Chemical Formula: C$_{23}$H$_{24}$N$_4$O$_2$<br>Exact Mass: 388.1899<br>Molecular Weight: 388.4623 | 389.2 |
| (R)-JQ30 | 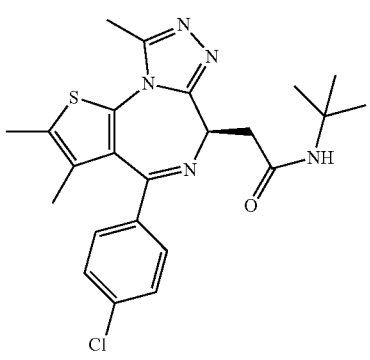 [SMILES: Cc1sc2c(c1C)C(c1ccc(Cl)cc1)=N[C@H](CC(=O)NC(C)(C)C)c1nnc(C)n1-2]<br>Chemical Formula: C$_{23}$H$_{26}$ClN$_5$OS<br>Exact Mass: 455.1547<br>Molecular Weight: 456.0034 | 456.2 |

| Compound Name | Structure | MS [M + H]+ m/z (Observed) |
|---|---|---|
| (R)-JQ31 | 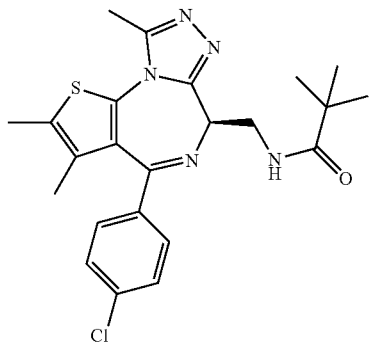 [SMILES: Cc1sc2c(c1C)C(c1ccc(Cl)cc1)=N[C@H](CNC(=O)C(C)(C)C)c1nnc(C)n1-2]<br>Chemical Formula: C_{23}H_{26}ClN_5OS<br>Exact Mass: 455.1547<br>Molecular Weight: 456.0034 | 456.2 |
| JQ32 | 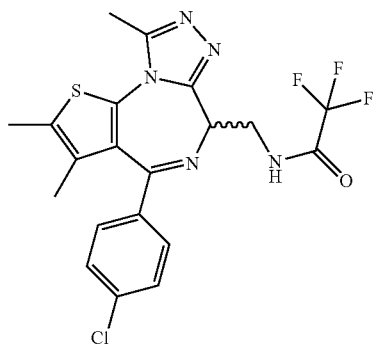 [SMILES: Cc1sc2c(c1C)C(c1ccc(Cl)cc1)=NC(CNC(=O)C(F)(F)F)c1nnc(C)n1-2]<br>Chemical Formula: C_{20}H_{17}ClF_3N_5OS<br>Exact Mass: 467.0794<br>Molecular Weight: 467.8951 | 468.1 |
| JQ33 | 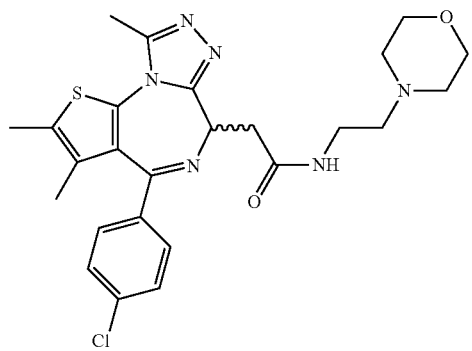 [SMILES: Cc1sc2c(c1C)C(c1ccc(Cl)cc1)=NC(CC(=O)NCCN1CCOCC1)c1nnc(C)n1-2]<br>Chemical Formula: C_{25}H_{29}ClN_6O_2S<br>Exact Mass: 512.1761<br>Molecular Weight: 513.0548 | 512.2 |

-continued

| Compound Name | Structure | MS [M + H]+ m/z (Observed) |
|---|---|---|
| JQ34 | Chemical Formula: C26H25ClN6OS<br>Exact Mass: 504.1499<br>Molecular Weight: 505.0343 | 505.1 |
| JQ35 | Chemical Formula: C27H34ClN7OS<br>Exact Mass: 539.2234<br>Molecular Weight: 540.1232 | 540.2 |
| JQ36 | Chemical Formula: C27H34ClN7OS<br>Exact Mass: 539.2234<br>Molecular Weight: 540.1232 | 540.2 |

| Compound Name | Structure | MS [M + H]+ m/z (Observed) |
|---|---|---|
| JQ37 | 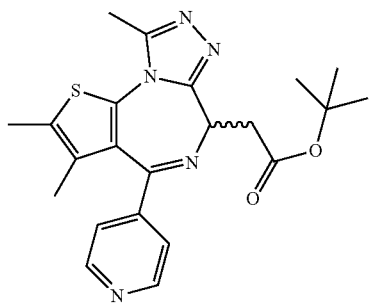 [SMILES: Cc1sc2c(c1C)C(c1ccncc1)=NC(CC(=O)OC(C)(C)C)c1nnc(C)n1-2]<br>Chemical Formula: C$_{22}$H$_{25}$N$_5$O$_2$S<br>Exact Mass: 423.1729<br>Molecular Weight: 423.5312 | 424.2 |
| JQ38 | 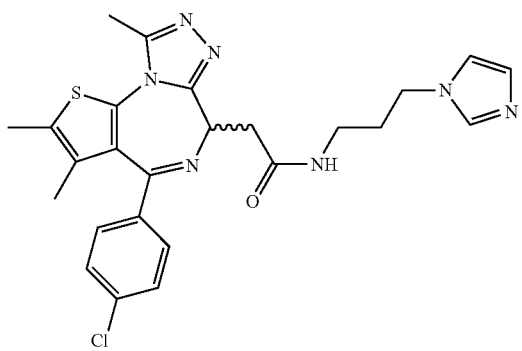 [SMILES: Cc1sc2c(c1C)C(c1ccc(Cl)cc1)=NC(CC(=O)NCCCn1ccnc1)c1nnc(C)n1-2]<br>Chemical Formula: C$_{25}$H$_{26}$ClN$_7$OS<br>Exact Mass: 507.1608<br>Molecular Weight: 508.0382 | 508.2 |
| JQ39 | 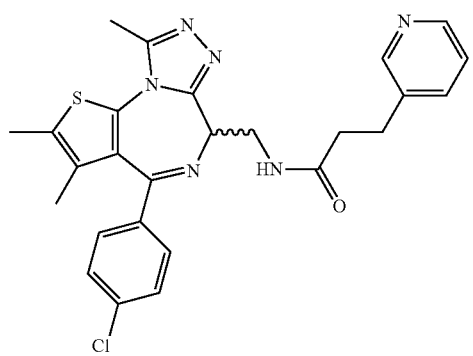 [SMILES: Cc1sc2c(c1C)C(c1ccc(Cl)cc1)=NC(CNC(=O)CCc1cccnc1)c1nnc(C)n1-2]<br>Chemical Formula: C$_{26}$H$_{25}$ClN$_6$OS<br>Exact Mass: 504.1499<br>Molecular Weight: 505.0343 | 505.1 |

-continued

| Compound Name | Structure | MS [M + H]+ m/z (Observed) |
|---|---|---|
| JQ40 | Chemical Formula: $C_{25}H_{30}ClN_7OS$<br>Exact Mass: 511.1921<br>Molecular Weight: 512.0700 | 512.2 |
| JQ41 | Chemical Formula: $C_{27}H_{34}ClN_7OS$<br>Exact Mass: 539.2234<br>Molecular Weight: 540.1232 | 540.2 |
| JQ42 | Chemical Formula: $C_{23}H_{25}FN_4O_2S$<br>Exact Mass: 440.1682<br>Molecular Weight: 440.5336 | 441.2 |

| Compound Name | Structure | MS [M + H]+ m/z (Observed) |
|---|---|---|
| JQ43 | 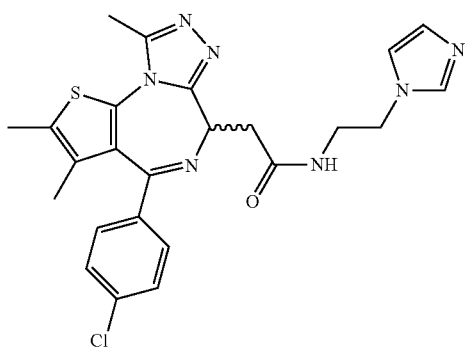 [SMILES: Cc1sc2c(c1C)C(c1ccc(Cl)cc1)=NC(CC(=O)NCCn1ccnc1)c1nnc(C)n1-2]<br>Chemical Formula: C$_{24}$H$_{24}$ClN$_7$OS<br>Exact Mass: 493.1452<br>Molecular Weight: 494.0117 | 494.1 |
| JQ44 | 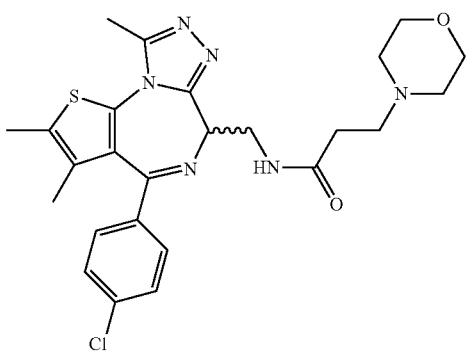 [SMILES: Cc1sc2c(c1C)C(c1ccc(Cl)cc1)=NC(CNC(=O)CCN1CCOCC1)c1nnc(C)n1-2]<br>Chemical Formula: C$_{25}$H$_{29}$ClN$_6$O$_2$S<br>Exact Mass: 512.1761<br>Molecular Weight: 513.0548 | 513.2 |
| JQ45 | 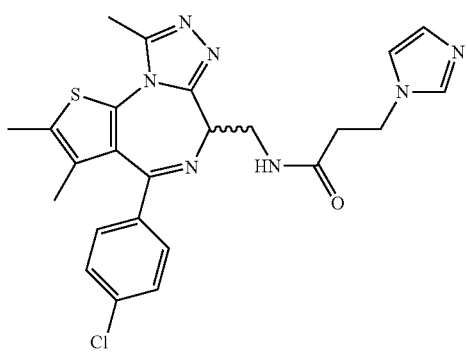 [SMILES: Cc1sc2c(c1C)C(c1ccc(Cl)cc1)=NC(CNC(=O)CCn1ccnc1)c1nnc(C)n1-2]<br>Chemical Formula: C$_{24}$H$_{24}$ClN$_7$OS<br>Exact Mass: 493.1452<br>Molecular Weight: 494.0117 | 494.1 |

| Compound Name | Structure | MS [M + H]+ m/z (Observed) |
|---|---|---|
| JQ46 | 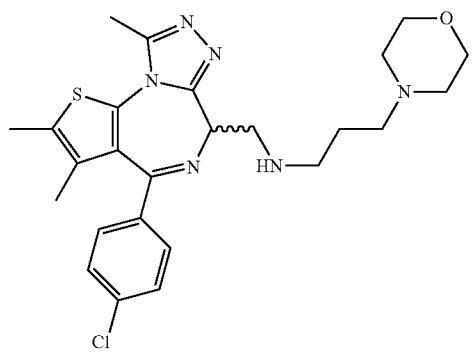 [SMILES: Cc1sc2c(c1C)C(c1ccc(Cl)cc1)=NC(CNCCCN1CCOCC1)c1nnc(C)n1-2]<br>Chemical Formula: C$_{25}$H$_{31}$ClN$_6$OS<br>Exact Mass: 498.1969<br>Molecular Weight: 499.0712 | 499.2 |
| JQ47 | 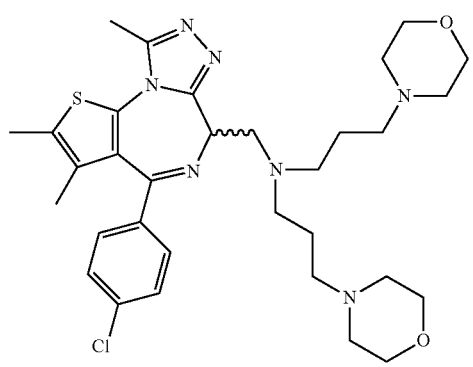 [SMILES: Cc1sc2c(c1C)C(c1ccc(Cl)cc1)=NC(CN(CCCN1CCOCC1)CCCN1CCOCC1)c1nnc(C)n1-2]<br>Chemical Formula: C$_{32}$H$_{44}$ClN$_7$O$_2$S<br>Exact Mass: 625.2966<br>Molecular Weight: 626.2555 | 626.3 |
| JQ48 | 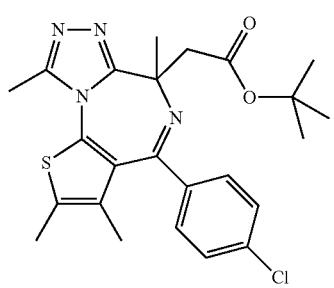 [SMILES: Cc1sc2c(c1C)C(c1ccc(Cl)cc1)=NC(C)(CC(=O)OC(C)(C)C)c1nnc(C)n1-2]<br>Exact Mass: 470.1543<br>Molecular Weight: 471.0148 | 471.2 |

-continued

| Compound Name | Structure | MS [M + H]+ m/z (Observed) |
|---|---|---|
| JQ49 | Exact Mass: 428.1074<br>Molecular Weight: 428.9350 | 429.1 |
| JQ50 | Exact Mass: 539.2234<br>Molecular Weight: 540.1232 | 540.2 |
| (S)-JQ51 | JQI-II-114<br>Exact Mass: 666.1816<br>Molecular Weight: 667.1764 | 667.2 |
| JQ52 | Exact Mass: 512.2125<br>Molecular Weight: 513.0978 | 513.2 |

-continued

| Compound Name | Structure | MS [M + H]+ m/z (Observed) |
|---|---|---|
| JQ53 | 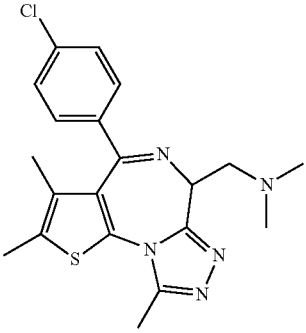 Exact Mass: 399.1284 Molecular Weight: 399.9402 | 400.1 |

Spectral data for each compound were consistent with the assigned structure.

II. BIOLOGICAL ACTIVITY

Example 2

Binding Assay Results

Results of a binding assay are shown below at Table B.

TABLE B

| | | Bio-assay $IC_{50}$ and Cell-assay $IC_{50}$ | |
|---|---|---|---|
| Compound | | Bio-assay $IC_{50}$ (μM) | |
| Name | Structure | BRD4(1) | BRD4(2) |
| (S)-JQ1 | 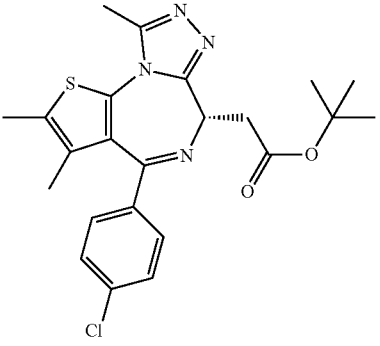 [SMILES: Cc1sc2c(c1C)C(c1ccc(Cl)cc1)=N[C@@H](CC(=O)OC(C)(C)C)c1nnc(C)n1-2] | 0.018 | 0.014 |
| (R)-JQ1 | 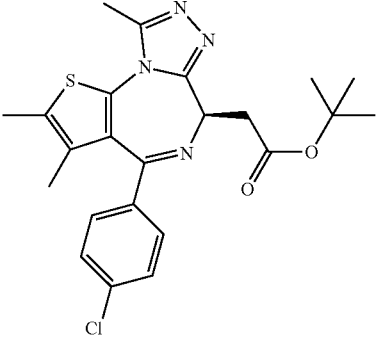 [SMILES: Cc1sc2c(c1C)C(c1ccc(Cl)cc1)=N[C@H](CC(=O)OC(C)(C)C)c1nnc(C)n1-2] | 8,354 | 52,120 |

TABLE B-continued

Bio-assay IC$_{50}$ and Cell-assay IC$_{50}$

| Compound Name | Structure | Bio-assay IC$_{50}$ (μM) | |
|---|---|---|---|
| | | BRD4(1) | BRD4(2) |
| (S)-JQ6 | | 0.00348 | 0.00024 |
| (S)-JQ8 | | 0.002189 | 0.000427 |
| (S)-JQ13 | | 0.002493 | 0.0005843 |
| (S)-JQ33 | | 0.085 | 0.0295 |

Chemical Formula: C$_{25}$H$_{29}$ClN$_6$O$_2$S
Exact Mass: 512.1761
Molecular Weight: 513.0548

TABLE B-continued

Bio-assay IC$_{50}$ and Cell-assay IC$_{50}$

| Compound | | Bio-assay IC$_{50}$ (µM) | |
|---|---|---|---|
| Name | Structure | BRD4(1) | BRD4(2) |
| (S)-JQ35 | [structure with chemical formula: C$_{27}$H$_{34}$ClN$_7$OS; Exact Mass: 539.2234; Molecular Weight: 540.1232] | 0.0243 | 0.00613 |

The binding activity of lead compounds with the BRD4 site 1 was determined by Alpha-assay with a 12-point dose response curve. Compound (S)-JQ1 (JQS) was used as a positive control. (R)-JQ1 (JQ-R) was used as a negative control. Compounds (S)-JQ6, (S)-JQ8, (S)-JQ13, (S)-JQ33 and (S)-JQ35 exhibited excellent binding activity. The results of binding activity of all lead compounds with the BRD4 site 2 was also determined by Alpha-assay with a 12-point dose response curve. Compounds (S)-JQ6, (S)-JQ8, (S)-JQ13, (S)-JQ33 and (S)-JQ35 exhibited excellent binding activity.

The activity of the lead compounds was examined in a cell-assay with the 797 cell line (derived from patient) to determine the growth effects of BRD4 inhibition on BRD4-NUT dependent cell lines. Cells were incubated with compounds and monitored for proliferation after 72 hours. Curve fit was calculated by logistical regression. All the lead compounds were examined in cell-assays with 10326 cell line that directly derived from a patient to determine the growth effects of BRD4 inhibition on BRD4-NUT dependent cell lines. Cells were incubated with compounds and monitored for proliferation after 72 hours. Curve fit was calculated by logistical regression.

Example 3

Rat Insulinoma Cell Assay

A Cell Titer-Glo assay was utilized to test the sensitivity of four rat insulinoma (RIN) cell lines, RIN-14B, RIN-m5F, RIN-m, and RIN-5, to (S)-JQ1 (Table 1). Paclitaxel was used as a positive control.

Cells were seeded at 5000 cells per well in a 96-well microculture plate in a total volume of 100 µl/well and incubated for 24 hours. 100 µl of 2× testing compounds ((S)-JQ1 or paclitaxel), serially diluted 1:4 were added to each well. The concentrations tested for (S)-JQ1 were, 20 µM, 5 µM, 1.25 µM, 0.313 µM, 0.0781 µM, 0.0195 µM, 0.00488 µM, 0.00122 µM, 0.000305 µM, and 0.0000763 µM. The concentrations tested for paclitaxel were, 10 µM, 2.5 µM, 0.625 µM, 0.156 µM, 0.0391 µM, 0.00977 µM, 0.00244 µM, 0.000610 µM, 0.000153 µM, and 0.0000381 µM. Duplicate data for RIN-5F was obtained where the test concentrations for paclitaxel were, 1 µM, 0.25 µM, 0.0625 µM, 0.0156 µM, 0.00391 µM, 0.000977 µM, 0.000244 µM, 0.0000610 µM, 0.0000153 µM, and 0.00000381 µM. After 168-192 total hours of culture 100 µl of media was removed from each well and 50 µl of Cell Titer-Glo (Promega #G7571) was added to each well. The plate was shaken for 2 minutes and allowed to equilibrate for 10 minutes. Luminescence was measured on a Tecan GENios microplate reader. Percent inhibition of cell viability was calculated relative to untreated control wells. All tests were performed in triplicate or quadruplicates at each concentration level. IC$_{50}$ values were calculated using Prism 6.00 curve-fitting with a four parameter-logistic equation.

Results

All cell lines were sensitive to (S)-JQ1 with IC$_{50}$ values under 100 nM. Higher concentrations of (S)-JQ1 reduced cell viability to virtually 0% indicating that (S)-JQ1 is having a cytotoxic effect (FIGS. 1-5). These results indicate that BET bromodomain inhibitors are highly effective in decreasing the viability of insulinoma cell lines.

TABLE 1

| | IC50 Values (nM) | |
|---|---|---|
| Cell Line | (S)-JQ1 | Paclitaxel |
| RIN-14B | 17 | 1.33 |
| RIN-m5F | 31 | 0.43 |
| RIN-m | 34 | 0.718 |
| RIN-5F | 96 and 61 | 1.63 and 3.14 |

Example 4

Rat Insulinoma Insulin Secretion Cell Assay

An ELISA assay was utilized to measure the effect of (S)-JQ1 and (S)-JQ35 on the amount of insulin secreted by the rat insulinoma (RIN) cell line RIN-m5F. DMSO was used as a vehicle control.

Cells were seeded at 300,000 cells per well in a 12-well culture plate in a total volume of 1 mL/well and incubated for 24 hours. After 24 hours of incubation, media was removed and 1 mL of growth media with test compounds (DMSO (control), (S)-JQ1 or (S)-JQ35) at a final concentration of 100 nM or 500 nM was added. After 24, 48, or 72 hours of treatment the amount of insulin secreted into the cell culture media was measured by an ELISA assay (Crystal Chemical, Cat #90060). The number of viable cells was determined at the end of each time point by Trypan Blue exclusion dye. The amount of insulin secreted per cell was calculated.

Figure 6:
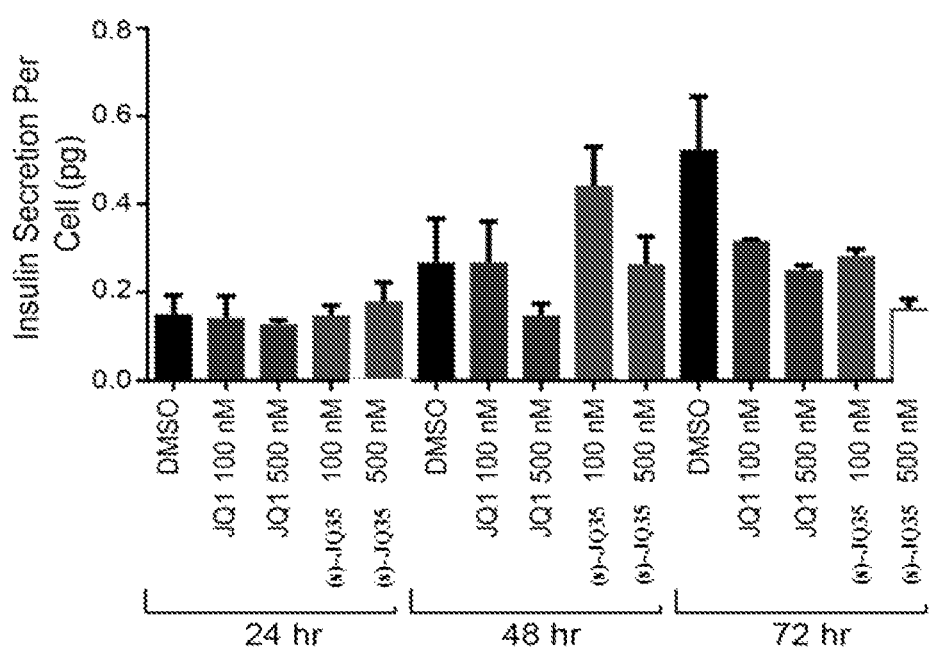
FIG. 6 is a graph showing insulin secretion over time of the rat insulinoma cells, RIN-m5F, when treated with varying concentrations of (S)-JQ1 or (S)-JQ35.
Figure 7:
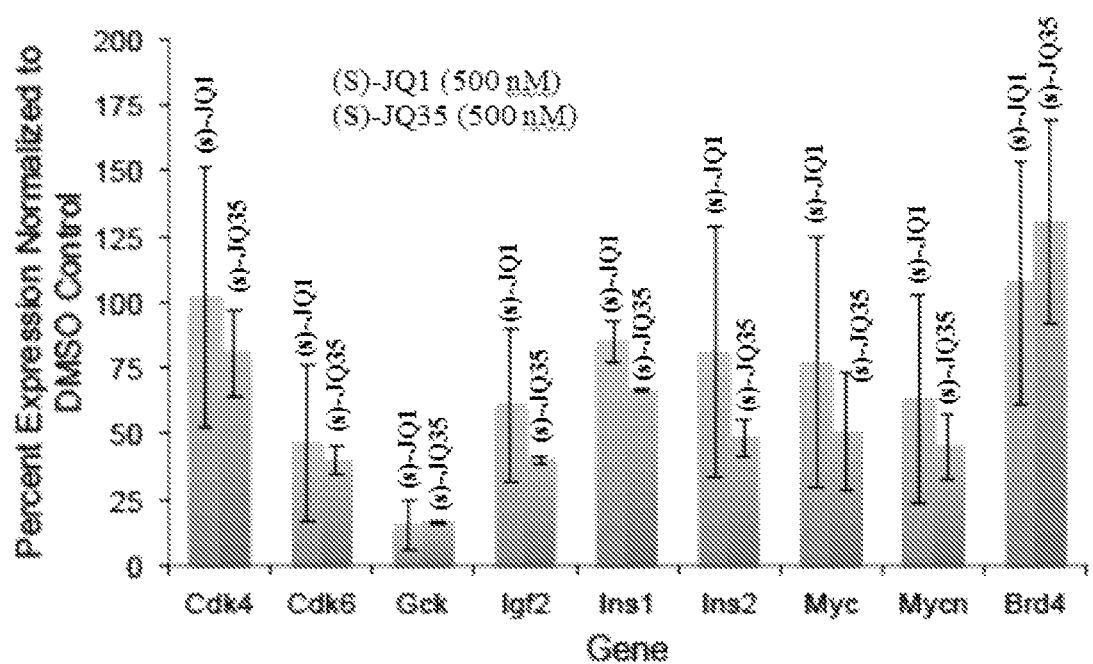
FIG. 7 is a graph showing the effect of BET Bromodomain inhibitors, (S)-JQ1 or (S)-JQ35, on gene expression in RIN-m5F cells when Actb is used as an internal control.
Figure 8:
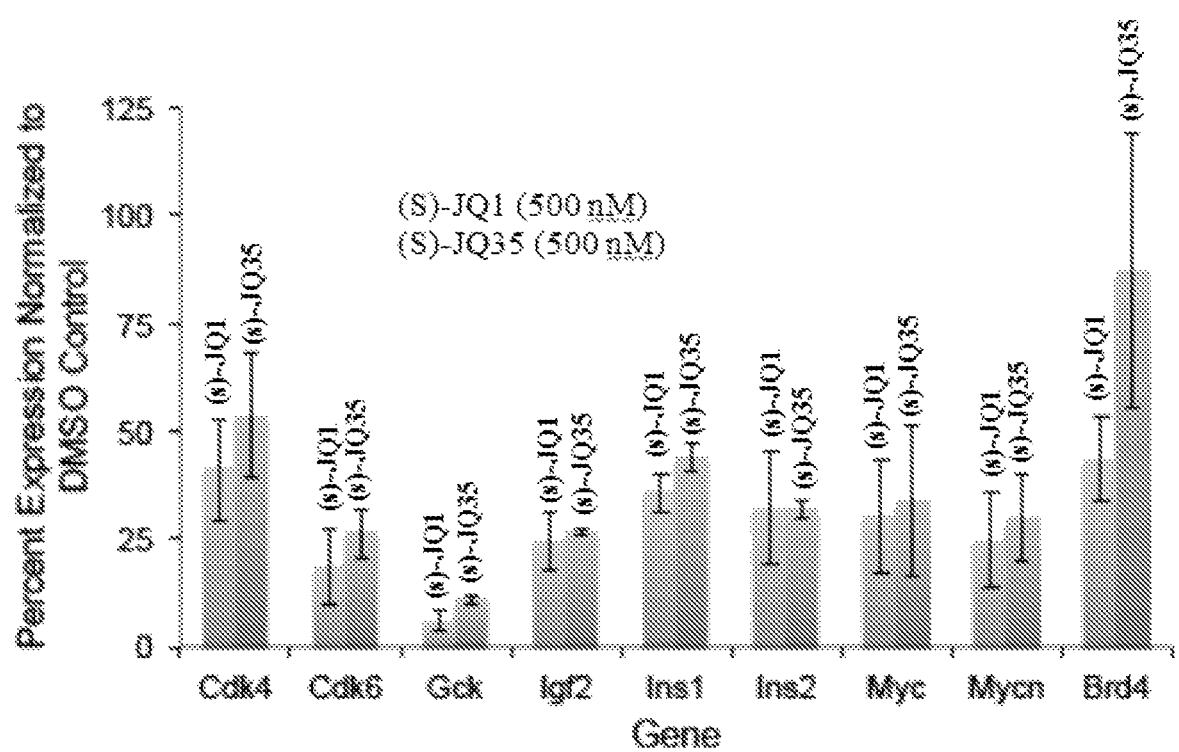
FIG. 8 is a graph showing the effect of BET Bromodomain inhibitors, (S)-JQ1 or (S)-JQ35, on gene expression in RIN-m5F cells when Gapdh is used as an internal control.
Figure 9:
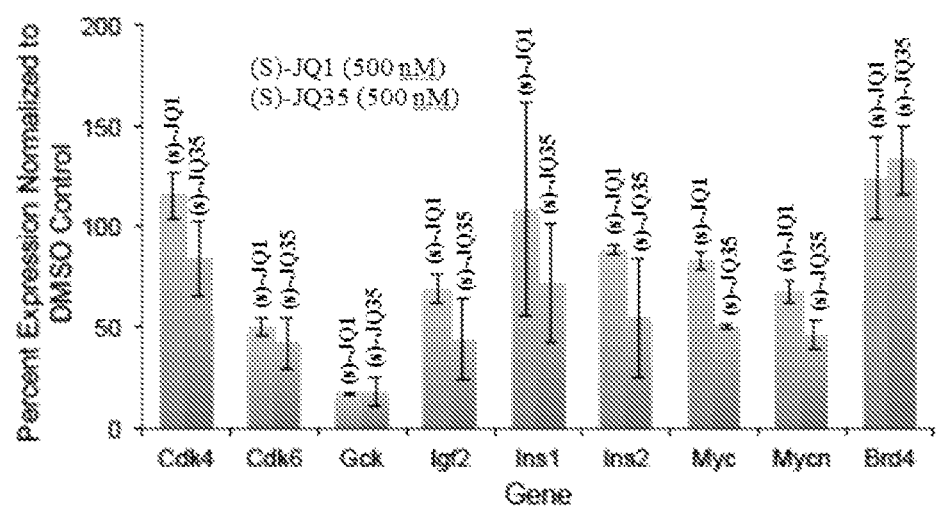
FIG. 9 is a graph showing the effect of BET Bromodomain inhibitors, (S)-JQ1 or (S)-JQ35, on gene expression in RIN-m5F cells when 18sRNA is used as an internal control.
Figure 10:
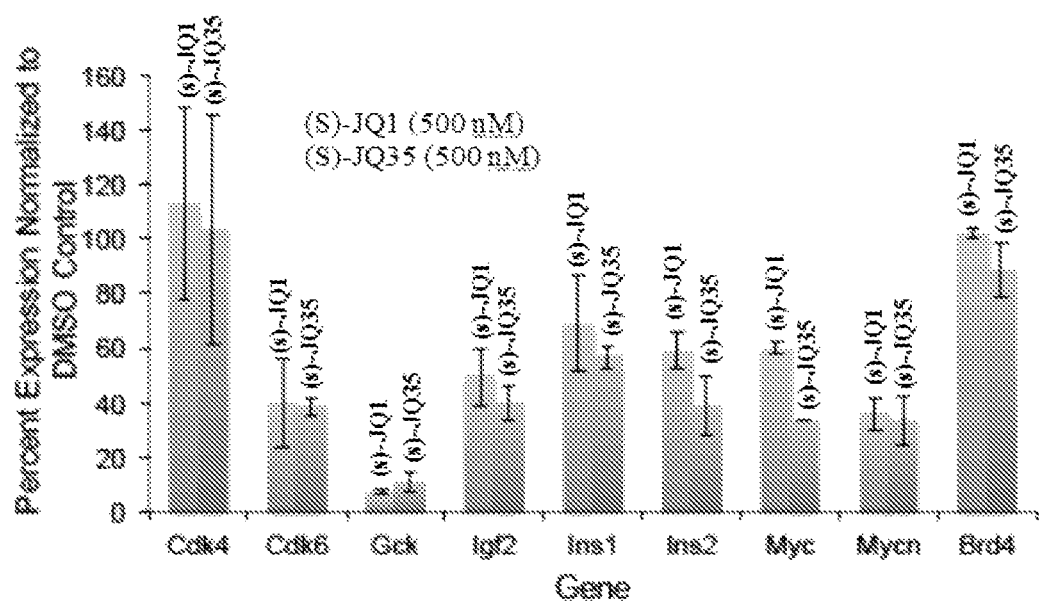
FIG. 10 is a graph showing the effect of BET Bromodomain inhibitors, (S)-JQ1 or (S)-JQ35, on gene expression in RIN-m cells when Actb is used as an internal control.
Figure 11:
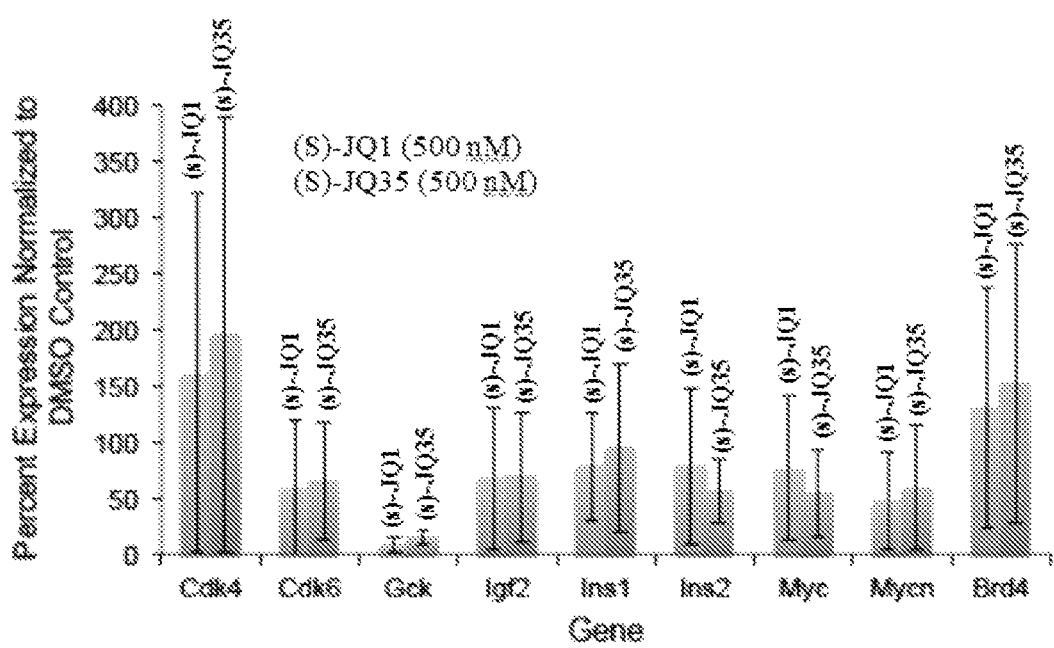
FIG. 11 is a graph showing the effect of BET Bromodomain inhibitors, (S)-JQ1 or (S)-JQ35, on gene expression in RIN-m cells when Gapdh is used as an internal control.
Figure 12:
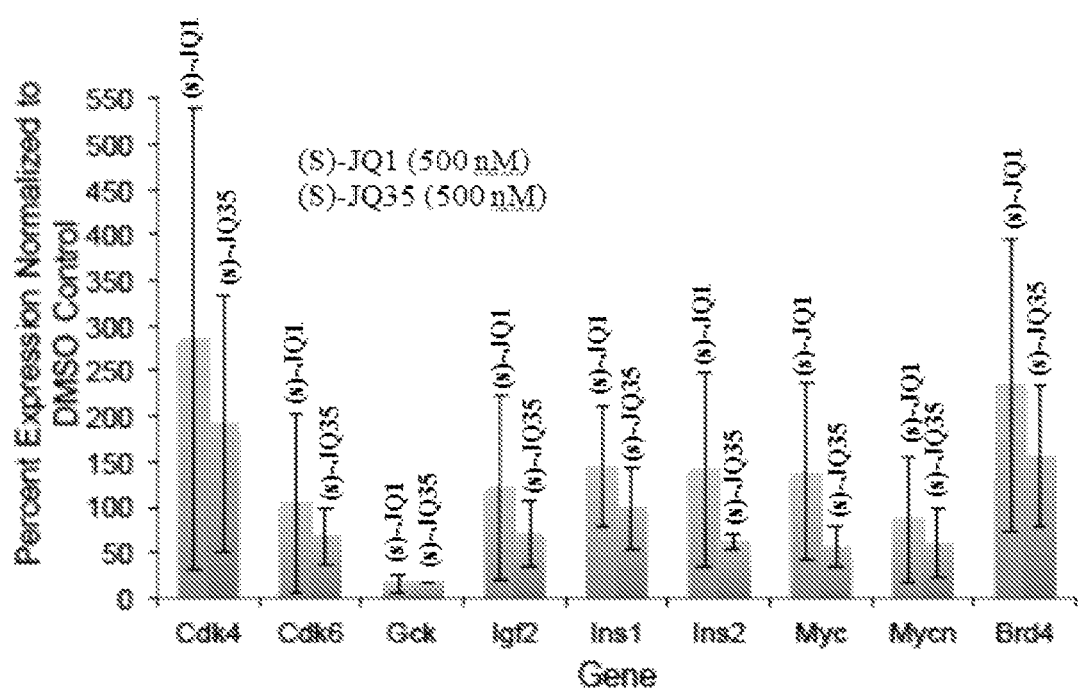
FIG. 12 is a graph showing the effect of BET Bromodomain inhibitors, (S)-JQ1 or (S)-JQ35, on gene expression in RIN-m cells when 18sRNA is used as an internal control.

BET bromodomain inhibitors decrease the amount of insulin secreted from the rat insulinoma cell line RIN-m5F. The results showed that over time the control treated cells secrete insulin into the cell culture media. However by the 72 hr time point, the BET bromodomain inhibitor treated cells did not secrete nearly as much insulin as the DMSO treated cells. There also appeared to be a dose dependent effect at this time point, with the 500 nM treatments having a greater effect on insulin secretion than the 100 nM treatments. Results are shown graphically in FIG. 6. These data support using BET bromodomain inhibtors to treat disorders associated with hyperinsulinaemia (e.g., insulinomas and congenital hyperinsulism) by reducing insulin production.

Example 5 qPCR Gene Expression Analysis in Rat Insulinoma Cell Lines

To further explore the sensitivity of insulinoma cells lines to BET bromodomain inhibitors, quantitative PCR (qPCR) gene expression analysis was conducted to measure the expression levels of Myc, Mycn, Cdk4, Cdk6, Ins1, Ins2, Gck, Igf2 and Brd4 in rat insulinoma cell lines, RIN-m5F and RIN-m cells. DMSO was used as a control.

Cell Culture and Drug Treatment

RIN-m5F or RIN-m cells were cultured in RPMI with 10% FBS. Cells were seeded at 2,000,000 cells/well in a 6-well plate (about $4 \times 10^5$ cells/cm$^2$) in a total volume of 2 mL/well. After 24 hours of incubation in a humidified incubator at 37° C. with 5% $CO_2$ and 95% air, the medium was replaced with 2-3 mL of fresh medium containing 0.1% DMSO, (S)-JQ1 (500 nM) or (S)-JQ35 (500 nM) and incubated for 24 hr. The media was removed and cells were washed twice with 2 mL cold PBS (1×). Cells were solubilized in 250 μL of Qiazol per well for a total of 2 mL and passed through a 23 gauge needle and syringe to break cell clumps. Lyses were stored at −80° C. or in liquid nitrogen.

RNA Extraction and cDNA Generation

Cell lyses were thawed on ice and 500 μl was transferred into a phase lock tube. 100 μl of chloroform was added and the tubes were shaken vigorously for 15 seconds and incubated for 2-3 minutes at room temperature. Samples were centrifuged for 13 minutes at 10,000×g at 2-8° C. Supernatant was removed, 600 μl of ethanol was added and tubes were mixed. Samples were added to a column (miRNeasy mini kit Qiagen, cat. 217004), and centrifuged for 4 minutes at 6000 rpm. 600 μl of RWT buffer (miRNeasy mini kit Qiagen, cat. 217004) was added to the column and centrifuged for 4 minutes at 6000 rpm. DNA was digested on column for 15 minutes at room temperature with DNase I (RNase free DNase kit, Qiagen, cat. 79254). 600 μl of RWT buffer was added to the column and centrifuged for 4 minutes at 6000 rpm. 700 μl of RPE (miRNeasy mini kit Qiagen, cat. 217004) buffer was added to the column and centrifuged for 4 minutes at 6000 rpm. 100 μl of RNase-free water was added to the column, incubated for 1 minute and RNA was eluted by centrifugation at 6000 rpm for 4 minutes. This elution step was repeated with 50 μl of RNase-free water and both eluates were combined. RNA concentrations were quantified and RNA was stored at −80° C.

cDNA was generated from 1000 ng of RNA with a Life Tech-RT Kit (Cat. 4304134). A RT-cDNA reaction mixture containing 10 μl of 10× RT buffer, 22 μl of 25 mM magnesium chloride ($MgCl_2$), 20 μl of 10 mM Deoxy NTP mix, 5.5 μl of Random hexamer, 2 μl of RNase inhibitor, 2.5 μl Multiscribe RT (50 U/μl), 18 μl of water and 20 μl (1000 ng) of RNA (50 ng/μl) (total volume of 100 μl) was setup.

Tubes were placed at 25° C. for 10 minutes, followed by 48° C. for 30 minutes, then 95° C. for 5 minutes and held at 4° C. indefinitely.

Quantitative PCR (qPCR)

Quantitative PCR (qPCR) was conducted with Ins 1, Ins 2, Myc, Mycn, Ifg2, Gck, Cdk6, Cdk4, Brd4 (Actb, Gadph and 18sRNA as controls) Taqman Probes (Applied Biosystems), on a QuantStudio-Real Time PCR machine (Life Technologies). A reaction mixture containing 1 μl of 20× Taqman probe, 10 μl of 2× Taqman Master mix (Life Technologies), 5 μl of Rnase free water, 4 μl of cDNA template (total volume 20 μl) was setup for each qPCR reaction.

All qPCR reactions were conducted in duplicate. Results were analyzed using the delta CT method. Actb, Gapdh or 18sRNA were used for internal controls. The percent expression for each gene following (S)-JQ1 or (S)-JQ35 treatment relative to the DMSO control treatment was calculated. (FIGS. 7-12) The duplicates were averaged and a standard deviation was calculated.

Results

Gene expression analysis was conducted in rat insulinoma cell lines on cell proliferation (Myc and Mycn), cell cycle (Cdk4 and Cdk6) and insulin pathway genes (Ins1, Ins2, Gck and Igf2) to determine the effect of BET bromodomain inhibitor treatment. The data for both tested inhibitors ((S)-JQ1 and (S)-JQ35) and cell lines was comparable (FIGS. 7-12). In general, depending on the internal control used (Actb, Gapdh or 18sRNA), seven out of the nine tested genes had decreased expression levels relative to the DMSO control treated cells. For most cases the greatest decrease in expression following BET inhibitor treatment occurred for Gck, followed by Cdk6, Igf2 and Mycn. Ins2, Ins2 and Myc had a more moderate decrease in expression. With few exceptions, BET inhibition did not substantially effect the expression of Cdk4 or Brd4 indicating that there was not a general decrease in transcriptional output. Furthermore, the expression changes that were observed cannot be attributed to altered levels of Brd4. Some variability in results was noted depending on the internal control used.

Overall the data is consistent with BET bromodomain inhibition resulting in a reduction in the expression levels of Myc, Mycn, Cdk6, Ins1, Ins2, Gck and Igf2. These data support the use of BET bromodomain inhibitors to treat insulinomas by potentially inhibiting the expression of cell proliferation genes, cell cycle regulators and components of the insulin pathway. These data also support using BET bromodomain inhibitors to treat disorders associated with hyperinsulinaemia (e.g., insulinomas and congenital hyperinsulism) by reducing insulin gene expression levels.

Example 6

Gene Specific Chromatin Immunoprecipitation Assay (ChIP)

A gene specific chromatin immunoprecipitation assay (ChIP) was performed in RIN-m5F cells to determine if Brd4 is directly regulating the insulin gene (Ins2) and c-Myc oncogene (Myc). Untranscribed region 17 (Untr 17) was used as a negative control.

Approximately 10-20 million RIN-m5F cells were fixed with 1% formaldehyde for 15 minutes and quenched with 0.125 M glycine. Chromatin was isolated by the addition of lysis buffer, followed by disruption with a Dounce homogenizer. Lysates were sonicated and the DNA sheared to an average length of 300-500 bp. Genomic DNA (Input) was prepared by treating aliquots of chromatin with RNase, proteinase K and heat for de-crosslinking, followed by ethanol precipitation. Pellets were resuspended and the resulting DNA was quantified on a NanoDrop spectrophotometer. Extrapolation to the original chromatin volume allowed quantitation of the total chromatin yield.

An aliquot of chromatin (30 ug) was precleared with protein A agarose beads (Invitrogen). Genomic DNA regions of interest were isolated using 4 ug of antibody against BRD4 (Bethyl Laboratories, Cat. #A301-985A100, Lot. #A301-985A100-1) or acetylated lysine 27 of histone H3 (H3K27Ac) (Active Motif, Cat. #39133, Lot. #7). Complexes were washed, eluted from the beads with SDS buffer, and subjected to RNase and proteinase K treatment. Crosslinks were reversed by incubation overnight at 65° C., and ChIP DNA was purified by phenol-chloroform extraction and ethanol precipitation.

Quantitative PCR (qPCR) reactions were carried out in triplicate on specific genomic regions (Ins2 promoter region, Myc promoter region or an untranscribed negative control region) using SYBR Green Supermix (Bio-Rad). The resulting signals were normalized for primer efficiency by carrying out qPCR for each primer pair using Input DNA.

Results

Figure 13:
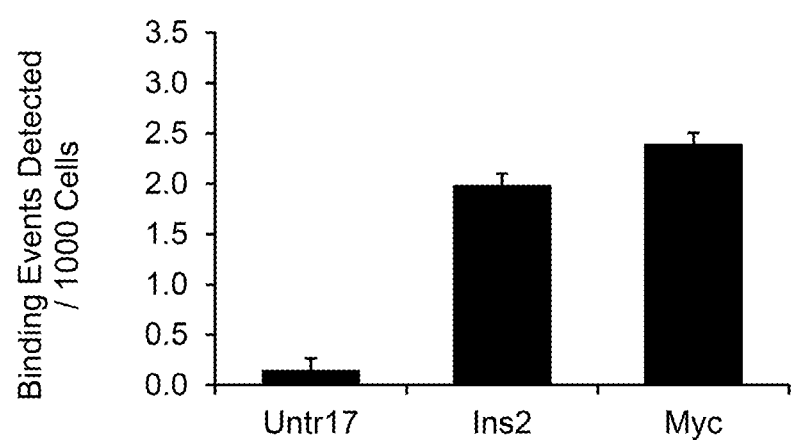
FIG. 13 is a graph showing Brd4 occupancy at the promoter region of the Insulin (Ins2), and c-Myc (Myc) genes and a negative control, untranscribed region Untr17, as determined by qPCR.

The results showed that Brd4 binds to the promoter region of the Ins2 gene (14-fold enrichment of binding over the negative control region) and the promoter region of Myc (17-fold enrichment over the negative control region) indicating that Brd4 directly regulates these genes and that BET bromodomain inhibitors will most likely cause a reduction in Ins2 and Myc expression by disrupting the ability of Brd4 to activate Ins2 and Myc expression (FIG. 13). These results are consistent with the qPCR gene expression analysis data obtained in Example 5.

Example 7

Chromatin Immunoprecipitation Sequencing (ChIP-seq) of BRD4 and Histone H3 Lysine 27 Acetylation (H3K27ac)

Chromatin immunoprecipitation assay followed by massively paralleled sequencing (ChIP-Seq) was performed in an insulinoma cell line, RIN-m5F cells, to determine the genomic wide localization of Brd4 and Histone H3 Lysine 27 Acetylation (H3K27ac).

ChIP and Input DNA was prepared as described above. Illumina sequencing libraries were prepared from the ChIP and Input DNAs using the Apollo 324 system (WaferGen). After a final PCR amplification step, the resulting DNA libraries were quantified and sequenced on HiSeq 2500. Sequences (50 nucleotide reads, single end) were aligned to the rat genome (rn5) using the BWA algorithm (default settings). Only reads that pass Illumina's purity filter, align with no more than 2 mismatches, and map uniquely to the genome are used in the subsequent analysis. In addition duplicate reads were removed. Alignments were extended in silico at their 3'-ends to a length of 200 bp, which is the average genomic fragment length in the size-selected library, and assigned to 32-nucleotide bins along the genome. The resulting histograms (genomic "signal maps") were stored in BAR and bigWig files. Peak locations were determined using the MACS algorithm (v1.4.2) with a cutoff of p-value=1e-7. (MACS: Zhang et al. Model-based Analysis of ChIP-Seq (MACS). Genome Biol (2008) vol. 9 (9) pp. R137; BWA: Li H. and Durbin R. (2009) Fast and accurate short read alignment with Burrows-Wheeler Transform. Bioinformatics, 25:1754-60. [PMID: 19451168]) The input DNA was utilized to remove false positive peaks. Signal maps and peak locations were used as input data to Active Motifs proprietary analysis program, which creates Excel tables containing detailed information on sample comparison, peak metrics, peak locations and gene annotations.

Results

The genome wide localization of Brd4 was determined by chromatin immunoprecipitation followed by massively paralleled sequencing (ChIP-Seq) in an insulinoma cell line. Brd4 was shown to occupy 18,875 regions (p-value cutoff of 1e-7) across the genome (Table C). Of these, 13,009 (68.9%) are found within 10 kb+/− of the beginning or end of a gene and 5,035 (26.7%) of the Brd4 occupied sites occurred within the promoter region of genes (500 bp of the transcriptional start site).

In order to determine if Brd4 is binding to enhancer regions, the genome wide localization of the enhancer mark (H3K27ac) was determined by ChIP-Seq (Table D). 27,756 regions were detected that had H3K27ac (p-value cutoff of 1e-7). Of the Brd4 occupied regions the majority (88.8%) overlapped with H3K27ac indicating that Brd4 occupies enhancers in insulinoma cells.

TABLE C

Brd4 ChIP-Seq Summary Data

| Occupied Regions | Occupied Genes* | Occupied Promoters*[1] | Overlap with H3K27ac |
|---|---|---|---|
| 18,875 | 13,009 (68.9%) | 5,035 (26.7%) | 16,767 (88.8%) |

*A gene was considered occupied if Brd4 binding occurred within +/−10 kb of the gene.

*[1]A promoter was considered occupied if Brd4 binding occurred within 500 bp of the transcriptional start site.

TABLE D

H3K27ac ChIP-Seq Summary Data

| Occupied Regions | Occupied Genes* | Occupied Promoters*[1] | Overlap with Brd4 |
|---|---|---|---|
| 27,756 | 18,832 (67.9%) | 5,798 (20.9%) | 15,495 (55.9%) |

Figure 14:
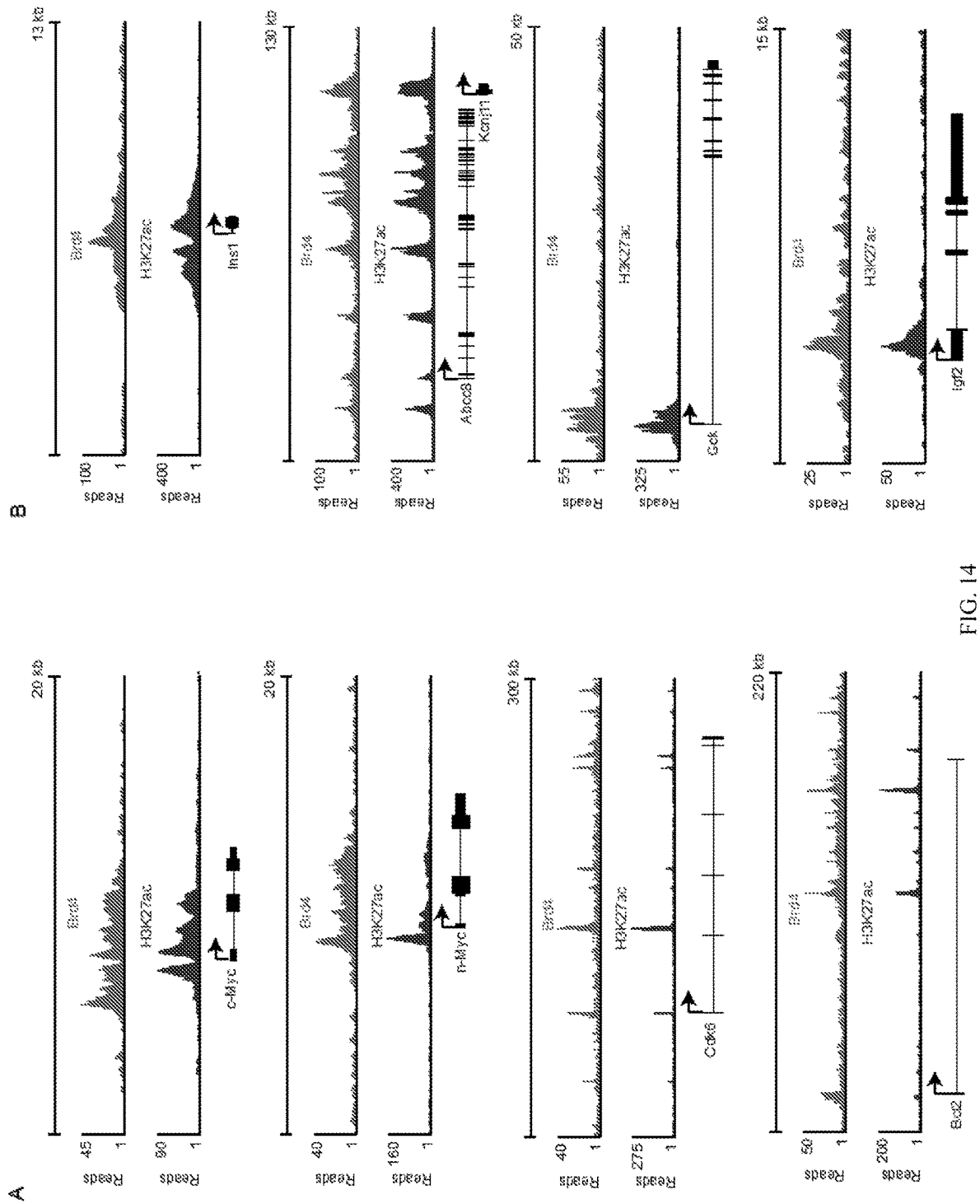
FIGS. 14A and 14B show the genome-wide occupancy of the Brd4 and H3K27ac in RIN-m5F cells determined by chromatin immunoprecipitation followed by massively paralleled sequencing (ChIP-Seq). Brd4 occupies the promoters and enhancers of oncogenes (FIG. 14A) and insulin pathway genes (FIG. 14B) in insulinoma cells.

*A gene was considered occupied if H3K27ac was detected within +/−10 kb of the gene.
*[1]A promoter was considered occupied if H3K27ac was detected within 500 bp of the transcriptional start site.

c-Myc, n-Myc, Cdk6 and Ins1 gene expression has been shown to decrease in rat insulinoma cell lines when Brd4 function is inhibited with BET bromodomain inhibitors. (Example 5) The results of the genome wide localization of Brd4 and H3K27ac indicate that Brd4 occupies both enhancer and promoter regions of oncogenes and insulin pathway genes in insulinoma cells. FIG. 14 shows that Brd4 occupancy occurs at the promoters and enhancer regions (note overlap with H3K27ac) of c-Myc, n-Myc genes, Cdk6, Bcl2, insulin 1 gene (Ins1), Abcc8, Kcnj11, Gck and Igf2. (FIGS. 14A and 14B). Taken together these results indicate that Brd4 occupies the promoters and enhancers of oncogenes and insulin pathway genes in insulinoma cells and provides evidence for why insulinoma cancer cell lines are sensitive to BET bromodomain inhibitors.

As shown in FIG. 14B, Brd4 occupies the promoters and enhancer regions of Abcc8, Kcnj11, Gck and Igf2 genes which have been linked not only to insulinomas but also other congenital hyperinsulinemia disorders. These results indicate that BET bromodomain inhibitors can have a therapeutic benefit for individuals afflicted with insulinomas or congenital hyperinsulinism conditions by mitigating insulin production.

Figure 15:
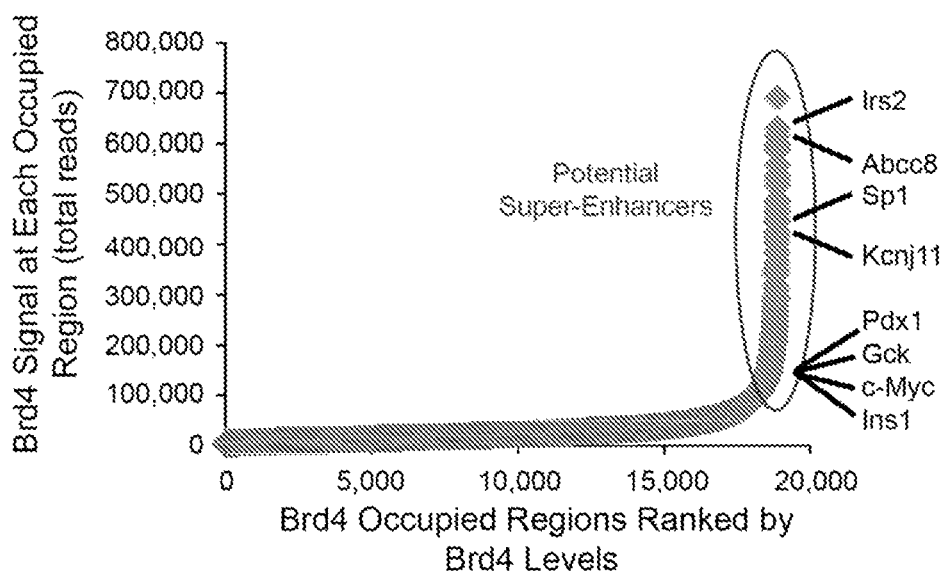
FIG. 15 is a graph showing the Brd4 signals determined by ChIP-Seq at each occupied region ranked by the total number of reads.

Super-enhancers are exceptionally large enhancer regions that are occupied by coactivators such as Brd4. Super-enhancers are found at oncogenes across a range of cancer types and at genes that are important for defining the biology of the cell type. Genes that are the most sensitive to BET bromodomain inhibition tend to be regulated by super-enhancers. Identification of super-enhancers allows for the prediction of genes that will be most sensitive to treatment with a BET bromodomain inhibitor. In order to identify potential super-enhancers in insulinoma all Brd4 bound regions were rank ordered by total number of reads (FIG. 15). A small percentage (top 4%) of Brd4-occupied regions contains a large portion of the Brd4 reads (21%). These regions likely represent super-enhancers. Some of these regions map close to oncogenes (c-Myc, Pax6 and Sp1) and genes that are important for the insulin pathway (Ins1, Abcc8, Kcnj11, Gck and Irs2). These results suggest that Brd4 regulates oncogenic drivers and key insulin pathway genes and that these genes should be the most sensitive to BET bromodomain inhibition.

The genome wide localization of Brd4 and H3K27ac indicates that Brd4 occupies both enhancer and promoter regions in insulinoma. Brd4 is found at the promoters, enhancers and potential super-enhancers of both oncogenes and insulin pathway genes, providing a rational for using BET bromodomain inhibitors to lower the expression levels of these genes in both insulinoma and CHI patients.

Example 8

Rat Insulinoma Cell Assay-Additional Data

A Cell Titer-Glo assay was utilized to test the sensitivity of four rat insulinoma (RIN) cell lines, RIN-14B, RIN-m5F, RIN-m, and RIN-5, to (S)-JQ1 and (S)-JQ35.

Cells were seeded at 5000 cells per well in a 96-well microculture plate in a total volume of 100 µl/well and incubated for 24 hours. 100 µl of 2× testing compounds ((S)-JQ1 or (S)-JQ35), serially diluted 1:4 were added to each well. The concentrations tested for (S)-JQ1 and (S)-JQ35 were, 20 µM, 5 µM, 1.25 µM, 0.313 µM, 0.0781 µM, 0.0195 µM, 0.00488 µM, 0.00122 µM, 0.000305 µM, and 0.0000763 µM. After 168-192 total hours of culture 100 µl of media was removed from each well and 50 µl of Cell Titer-Glo (Promega #G7571) was added to each well. The plate was shaken for 2 minutes and allowed to equilibrate for 10 minutes. Luminescence was measured on a Tecan GENios microplate reader. Percent inhibition of cell viability was calculated relative to untreated control wells. All tests were performed in triplicate or quadruplicates at each concentration level. $IC_{50}$ values were calculated using Prism 6.00 curve-fitting with a four parameter-logistic equation.

Results

All cell lines were sensitive to (S)-JQ1 with $IC_{50}$ values under 100 nM and to (S)-JQ35 under 200 nM. Higher concentrations of (S)-JQ1 and (S)-JQ35 reduced cell viability to virtually 0% indicating that (S)-JQ1 and (S)-JQ35 are both having a cytotoxic effect. These results indicate that BET bromodomain inhibitors are highly effective in decreasing the viability of insulinoma cell lines.

| Cell Line | IC50 Values (nM) | |
|---|---|---|
| | (S)-JQ1 | (S)-JQ35 |
| RIN-14B | 20.7 | 207.3 |
| RIN-m5F | 51.0 | 188.3 |
| RIN-m | 29.3 | 151.4 |
| RIN-5F | 52.0 and 73.1 | 183.2 and 214.7 |

Example 9

Expression Analysis of JQ1 Treated RIN-m5F Insulinoma Cells

Gene expression analysis was conducted on the insulinoma cell line RIN-m5F following JQ1 treatment. As shown below, BET inhibition disrupts both oncogenic and pancreatic islet cell transcriptional profiles.

RIN-m5F rat insulinoma cells were treated with JQ1 (500 nM) or DMSO (control) for 24 hr. Cells were scraped and total RNA was extracted and purified using a Qiagen RNeasy Mini Kit (cat. 74104) as described in the manufacturer's protocol. Residual DNA was removed by treatment with DNase I. The final yield of RNA was 123 µg and 136 µg for the DMSO and JQ1 treated cells, respectively. For each sample, 4 µg of total RNA was then used in Illumina's TruSeq RNA sample preparation V2 kit. The concentrations of the final library preps were 71 ng/µl and 79 ng/µl for the DMSO and JQ1 samples, respectively. Libraries were sequenced on Illumina NextSeq 500 as paired-end 75-nt reads.

Sequence reads were analyzed with the TopHat—Cufflinks software pipeline. Average size of library molecules was 400 bp, therefore the—r parameter was set to 125. (Versions were: TopHat v2.0.9, Bowtie 2.1.0.0, Cufflinks v2.1.1). The rat (rn5) gene reference GTF file was obtained from Illumina iGenomes.

121
Results

Figure 16:
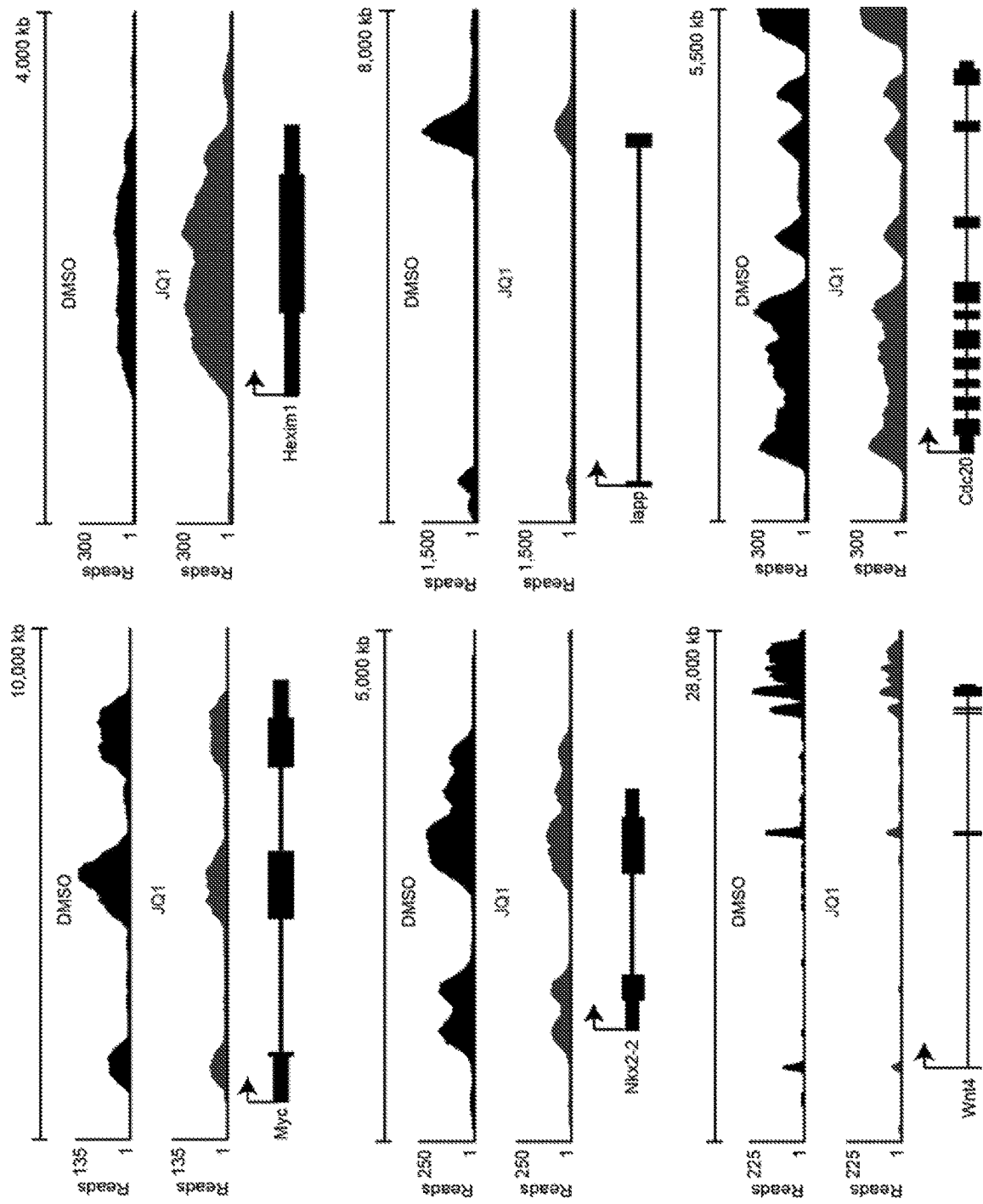
FIG. 16 shows expression changes in exemplary genes following JQ1 treatment of RIN-m5F cells, as determined by sequencing (the RNA-Seq data) and analysis of the library. Arrows denote the transcriptional start site for each gene; thicker lines in the gene models represent exons.

To validate the RNA-Seq dataset, the expression changes of two known control genes, c-Myc and hexamethylene bis-acetamide inducible 1 (Hexim1), were inspected (FIG. 16). Consistent with various pre-clinical cancer models following BET inhibition, an approximate 2-fold decrease in c-Myc levels were observed. Similarly, an approximate 5-fold increase in Hexim1 levels was observed, in keeping with previous studies, thereby validating the RNA-Seq dataset.

JQ1 treatment resulted in a larger number of genes with decreased expression as compared to increased expression (Table E).

TABLE E

Number of Genes With Expression Changes Following JQ1 Treatment

| Expression Change | Number of Genes |
| --- | --- |
| 2-fold decrease | 1234 |
| 2-fold increase | 352 |
| 4-fold decrease | 377 |
| 4-fold increase | 41 |
| 8-fold decrease | 97 |
| 8-fold increase | 6 |

Inspection of individual genes demonstrated that oncogenes in addition to c-Myc, such as cell-division cycle protein 20 (cdc20) were also downregulated (FIG. 16 and Table F). Genes important for pancreatic islet cell function also decreased in expression, such as NK2 homeobox 2 (Nkx2-2), islet amyloid polypeptide (Iapp) and Wingless-type MMTV integration site family, member 4 (Wnt4) (FIG. 16 and Table F).

TABLE F

Examples of Genes With Expression Changes Following JQ1 Treatment

| Gene | Function | Fold Change |
| --- | --- | --- |
| c-Myc | Proliferation, cell cycle, anti-apoptotic | 2.4 (decrease) |
| Hexim1 | Negative regulator of transcriptional elongation | 4.6 (increase) |
| Cdc20 | Cell division, up regulated in pancreatic cancer | 2.1 (decrease) |
| Nkx2-2 | Pancreatic development | 2.7 (decrease) |
| Iapp | Pancreatic glycemic regulation | 3.4 (decrease) |
| Wnt4 | β-cell proliferation | 4.3 (decrease) |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for treating hyperinsulinaemia in a subject suffering from insulinoma in need thereof, comprising administering to the subject an effective amount of a compound represented by Structural Formula VI:

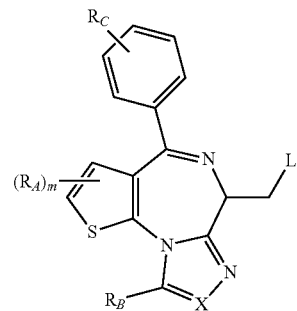

(VI)

or a pharmaceutically acceptable salt thereof, wherein:

X is N;

$R_B$ is methyl, ethyl, hydroxy methyl, methoxymethyl, or trifluoromethyl;

each $R_A$ is methyl;

L is —CO—N($R_9R_{10}$), $R_9$ is —($C_0$-$C_6$)alkylene-heterocycloalkyl, —($C_0$-$C_6$) alkylene-aryl, or —($C_0$-$C_6$)alkylene-heteroaryl and each -heterocycloalkyl, -aryl, and -heteroaryl is optionally and independently substituted with 1 to 4 ($C_1$-$C_4$)alkyl, and $R_{10}$ is H or —($C_1$-$C_6$)alkyl; or L is —COO—R'$_9$, and R'$_9$ is independently selected from the group consisting of —($C_1$-$C_6$)alkyl, —($C_0$-$C_6$)alkylene-heterocycloalkyl, —($C_0$-$C_6$)alkylene-aryl, and —($C_0$-$C_6$)alkylene-heteroaryl and each —($C_1$-$C_6$)alkyl, -heterocycloalkyl, -aryl, and -heteroaryl is optionally substituted with 1 to 4 substituents independently selected from the group consisting of —F, —Cl, —Br, and —($C_1$-$C_6$)alkyl;

$R_C$ is selected from the group consisting of: —F, —Cl, —Br, —OH, and —O—($C_1$-$C_4$)alkyl;

and m is 2.

2. The method of claim 1, wherein L is —COO—R'$_9$, and R'$_9$ is selected from the group consisting of: methyl, ethyl, propyl, i-propyl, butyl, sec-butyl, t-butyl, and trifluoromethyl.

3. The method of claim 1, wherein the compound is represented by the following structural formula:

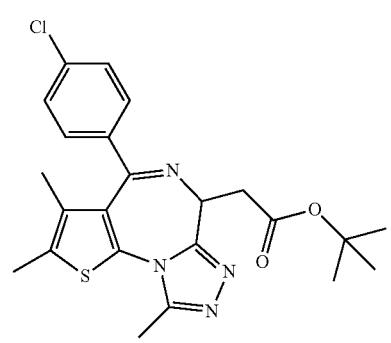 [SMILES: Cc1sc2c(c1C)C(c1ccc(Cl)cc1)=NC(CC(=O)OC(C)(C)C)c1nnc(C)n1-2]

or a pharmaceutically acceptable salt thereof.

4. The method of claim 3, wherein the compound is represented by the following structural formula:

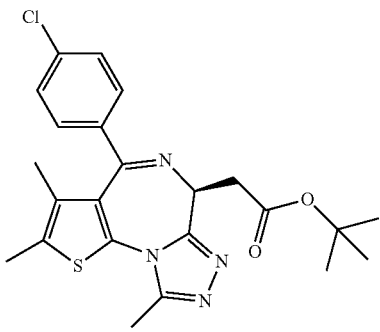 [SMILES: Cc1sc2c(c1C)C(c1ccc(Cl)cc1)=N[C@@H](CC(=O)OC(C)(C)C)c1nnc(C)n1-2]

or a pharmaceutically acceptable salt thereof.

5. A method for treating hyperinsulinaemia in a subject suffering from insulinoma in need thereof, comprising administering to the subject an effective amount of a compound represented by the following structural formulas:

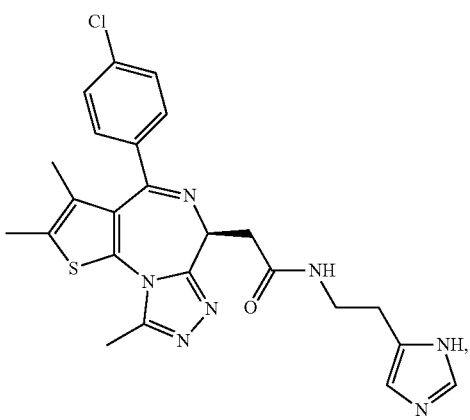

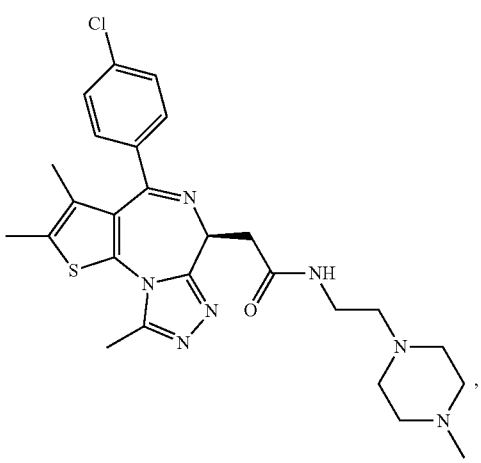

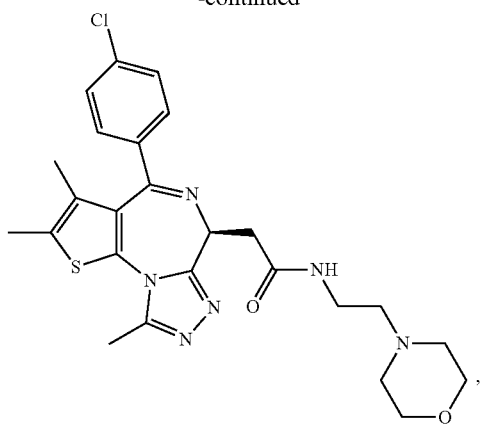

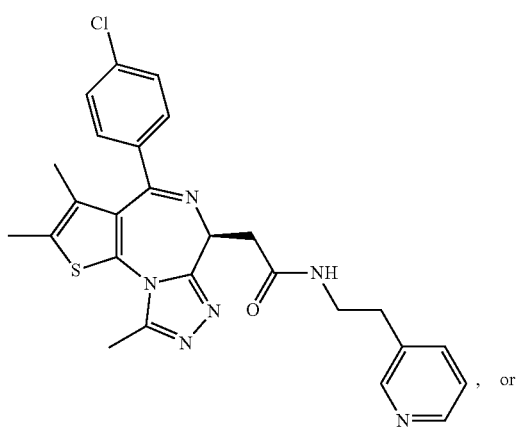

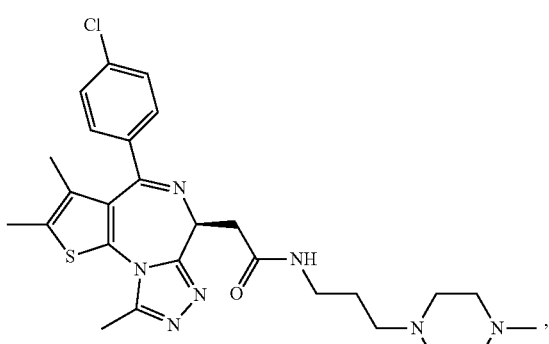

or a pharmaceutically acceptable salt thereof.

6. A method for treating hyperinsulinaemia in a subject suffering from insulinoma in need thereof, comprising administering to the subject an effective amount of a compound represented by the following structural formulas:

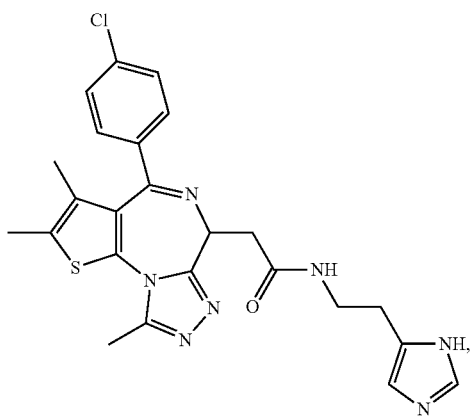
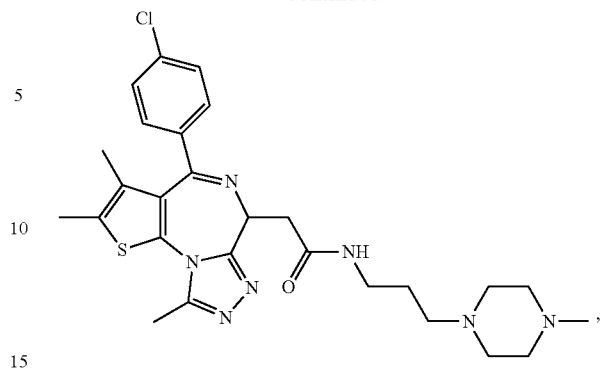
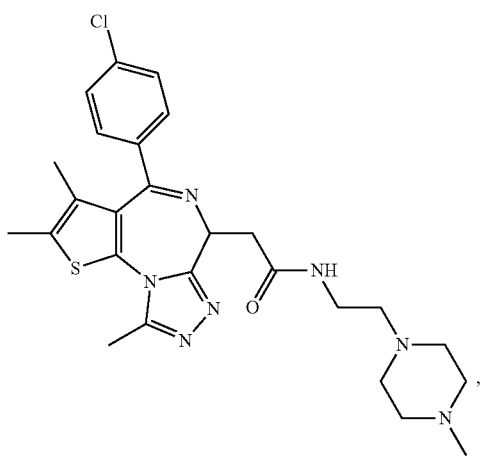
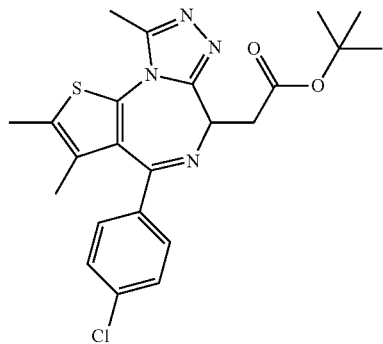
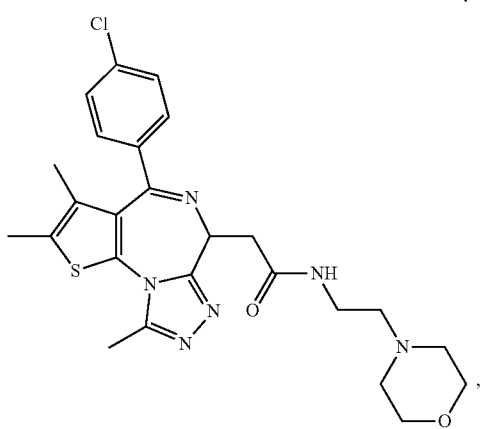
or a pharmaceutically acceptable salt thereof.
7. The method of claim 1, wherein the compound is represented by the following structural formulas:
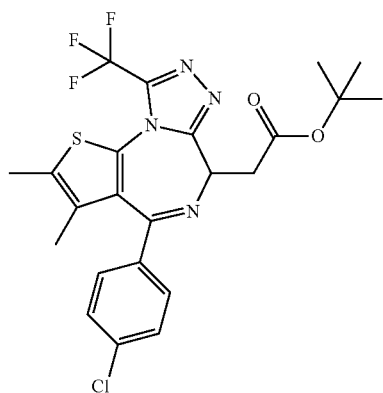
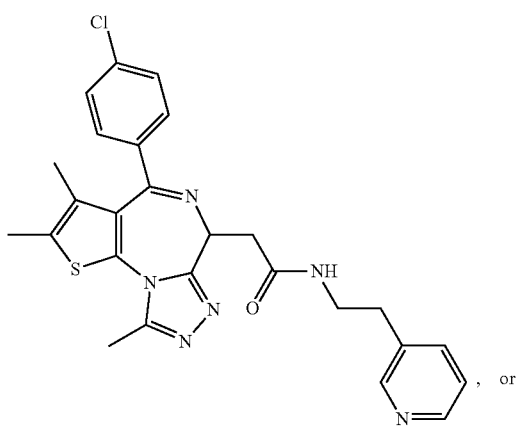, or
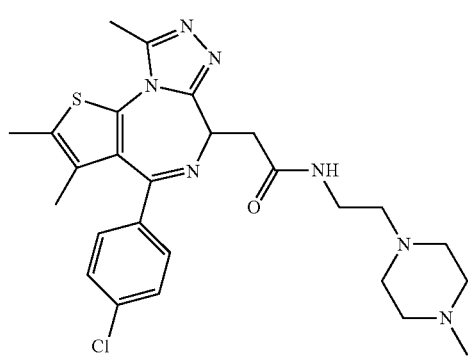

127
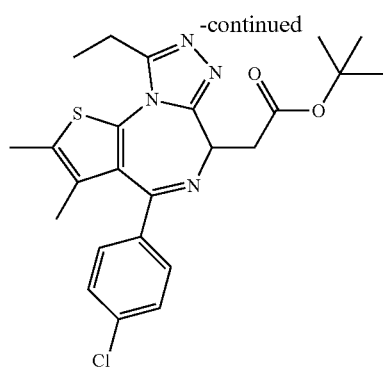
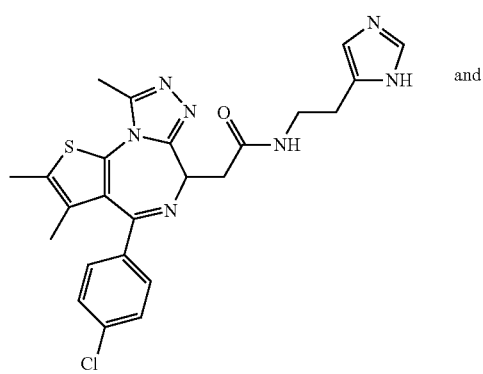
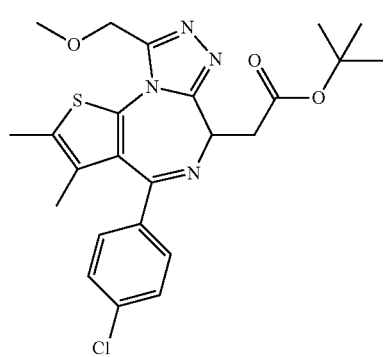
or a pharmaceutically acceptable salt thereof.
8. The method of claim 7, wherein the compound represented by the following structural formulas:
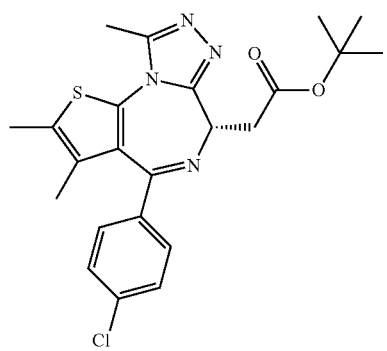
128
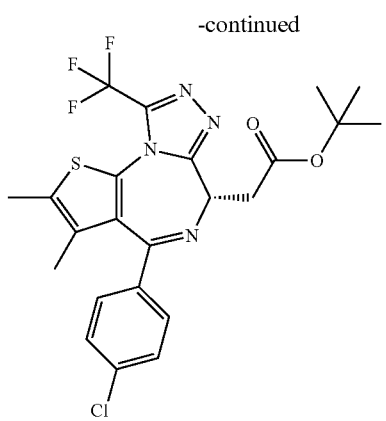
and
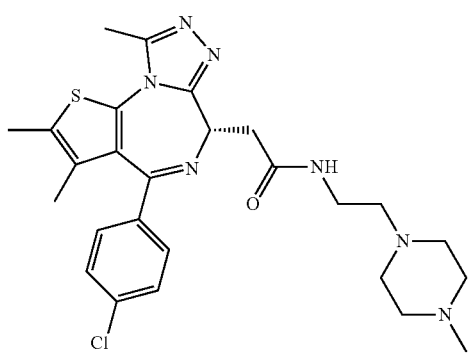
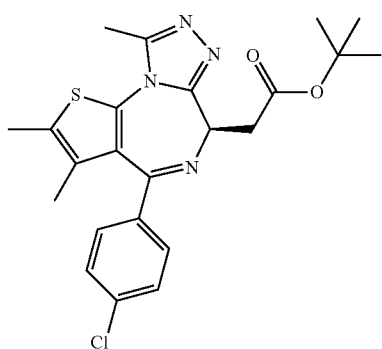
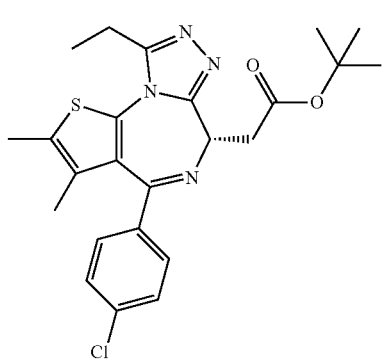

-continued

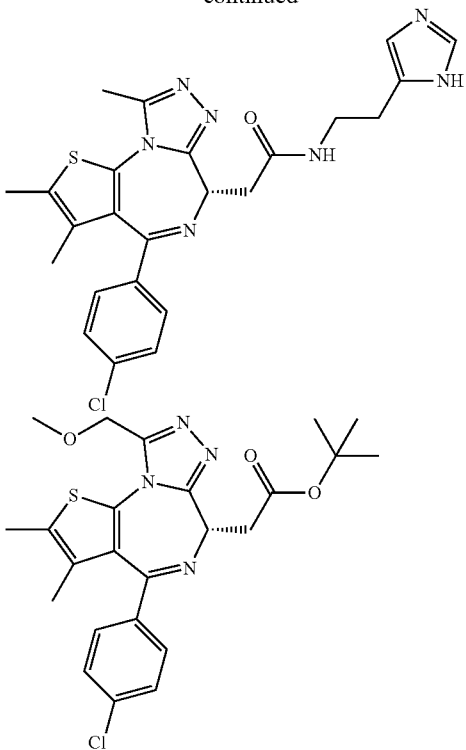

and or a pharmaceutically acceptable salt thereof.

9. The method of claim 1, wherein the subject is a mammal.

10. The method of claim 9, wherein the subject is a human.

11. The method of claim 5, wherein the subject is a mammal.

12. The method of claim 11, wherein the subject is a human.

13. The method of claim 6, wherein the subject is a mammal.

14. The method of claim 13, wherein the subject is a human.

15. The method of claim 1, wherein the compound is represented by the following structural formula:

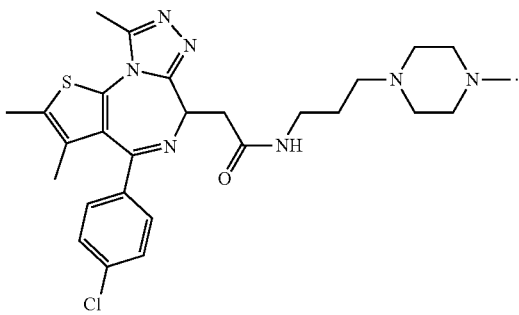

16. The method of claim 5, wherein the compound is represented by the following structural formula:

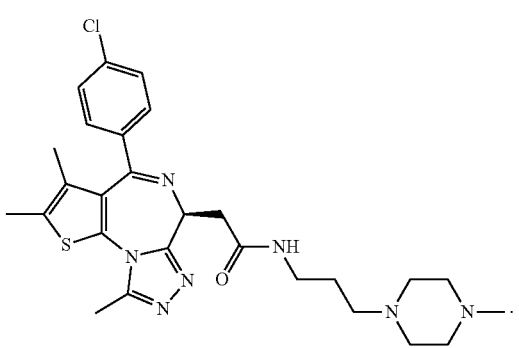

* * * * *